United States Patent [19]

Nishi et al.

[11] Patent Number: 5,401,740

[45] Date of Patent: * Mar. 28, 1995

[54] CARBOSTYRIL DERIVATIVE

[75] Inventors: Takao Nishi; Makoto Komatsu; Yasuo Koga; Yoshio Shu; Katsumi Tamura, all of Tokyo, Japan

[73] Assignee: Otsuka Pharmaceutical Co., Tokyo, Japan

[*] Notice: The portion of the term of this patent subsequent to Jul. 13, 2010 has been disclaimed.

[21] Appl. No.: 273,624

[22] Filed: Jul. 12, 1994

Related U.S. Application Data

[60] Continuation of Ser. No. 44,663, Apr. 9, 1993, abandoned, which is a division of Ser. No. 928,097, Aug. 13, 1992, Pat. No. 5,227,381, which is a continuation of Ser. No. 449,849, Dec. 27, 1989, abandoned.

[30] Foreign Application Priority Data

May 2, 1988 [JP] Japan ................. 63-109534

[51] Int. Cl.[6] ............ A61K 31/47; A61K 31/505; C07D 401/12; C07D 403/12
[52] U.S. Cl. ............... 514/228.2; 514/235.2; 514/312; 544/58.6; 544/128; 544/331; 544/332; 546/153; 546/157; 546/158
[58] Field of Search ............... 544/58.6, 128; 546/153, 546/157, 158; 514/228.2, 235.2, 312

[56] References Cited

U.S. PATENT DOCUMENTS

| | | | |
|---|---|---|---|
| 4,070,470 | 1/1978 | Nakagawa et al. | 514/312 |
| 4,298,739 | 11/1981 | Nishi et al. | 546/158 |
| 4,435,404 | 3/1984 | Nishi et al. | 514/312 |
| 4,482,560 | 11/1984 | Banno et al. | 514/312 |
| 5,008,274 | 4/1991 | Nishi et al. | 514/312 |

*Primary Examiner*—Mukund J. Shah
*Assistant Examiner*—Matthew V. Grumbling
*Attorney, Agent, or Firm*—Finnegan, Henderson, Farabow, Garrett & Dunner

[57] ABSTRACT

The novel carbostyril derivative represented by the general formula (1)

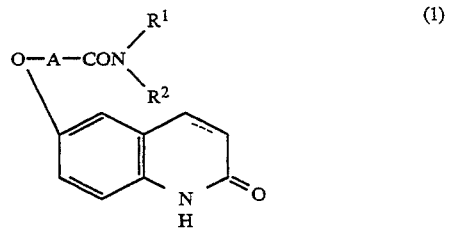

[in the formula, A, $R^1$, $R^2$ and the carbon-carbon bond between 3- and 4-positions in the carbostyril skeleton have the same definitions as above] has an excellent platelet aggregation inhibitory activity, a phosphodiesterase inhibitory activity, a venticular contraction activity (a positive contraction activity), an anti-ulcer activity, an anti-inflammatory activity, a cerebral blood flow increasing activity, a thrombus dissociation activity, a thromboxane $A_2$ antagonism activity, etc. The carbostyril derivative of the present invention is characterized in that it exhibits the above activities for a long time, is low in toxicity (particularly low in toxicity to hearts of cardiovascular hyperplasia, myocardipathy, etc.), and is low in circulation activities such as heart rate increasing activity, blood pressure decreasing activity and the like. Also, the carbostyril derivative of the present invention has advantages in that it is easily absorbed by the intestinal tract and easily migrates into blood. Therefore, the carbostyril derivative of the present invention can be used most suitably as a preventive and remedy for thrombi such as apoplexia, cerebral infarction, myocardial infarction and the like, a cerebral circulation improving agent, an anti-inflammatory agent, an antiasthmatic agent, a cardiotonic agent and a phosphodiesterase inhibitory agent.

23 Claims, No Drawings

CARBOSTYRIL DERIVATIVE

This application is a continuation of application Ser. No. 08/044,663, filed Apr. 9, 1993, now abandoned, which is a divisional of application Ser. No. 07/928,097, filed Aug. 13, 1992 (U.S. Pat. No. 5,227,381), which is a continuation of application Ser. No. 07/449,849, filed Dec. 27, 1989, now abandoned.

TECHNICAL FIELD

The present invention relates to a novel carbostyril derivative, a salt thereof, a process for producing said derivative, and a pharmaceutical composition for inhibiting platelet aggregation which contains said novel carbostyril derivative as an active ingredient.

BACKGROUND OF THE INVENTION

Of carbostyril derivatives, many of them have hitherto been known to have useful pharmacological activities. For example, those carbostyril derivatives having a side chain similar to the side chain of the carbostyril derivative of the present application, represented by the formula

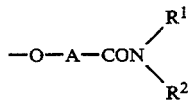

and having a platelet aggregation inhibitory activity as the pharmacological activity, are disclosed in U.S. Pat. No. 4,070,470, U.S. Pat. No. 4,216,220, U.S. Pat. No. 4,313,947, U.S. Pat. No. 4,298,739, U.S. Pat. No. 4,435,404; British Patent No. 1,505,305, British Patent No. 2,002,745, British Patent No. 2,070,588; German Patent No. 2,527,937, German Patent No. 2,825,048, German Patent Laid-Open No. 3049959.3; Japanese Patent Kokai (Laid-Open) No. 51-23271 (1976), Japanese Patent Kokai (Laid-Open) No. 51-23272 (1976), Japanese Patent Kokai (Laid-Open) No. 51-136676 (1976), Japanese Patent Kokai (Laid-Open) No. 54-5981 (1979), Japanese Patent Kokai (Laid-Open) No. 54-12385 (1979), Japanese Patent Kokai (Laid-Open) No. 54-115383 (1979), Japanese Patent Kokai (Laid-Open) No. 58-23622 (1983), Japanese Patent Kokai (Laid-Open) No. 54-163825 (1979), Japanese Patent Kokai (Laid-Open) No. 55-35018 (1980), Japanese Patent Kokai (Laid-Open) No. 55-76864 (1980), Japanese Patent Kokai (Laid-Open) No. 55-79370 (1980), Japanese Patent Kokai (Laid-Open) No. 55-79371 (1980), Japanese Patent Kokai (Laid-Open) No. 55-79372 (1980), Japanese Patent Kokai (Laid-Open) No. 56-122356 (1981), Japanese Patent Kokai (Laid-Open) No. 57-2274 (1982), Japanese Patent Kokai (Laid-Open) No. 57-93962 (1982), Japanese Patent Kokai (Laid-Open) No. 57-175168 (1982), Japanese Patent Kokai (Laid-Open) No. 57-183761 (1982), Japanese Patent Kokai (Laid-Open) No. 59-46202 (1984), etc.

Also, those compounds which have a side chain similar to the side chain of the carbostyril derivative of the present application, represented by the formula

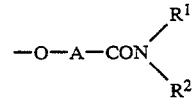

and have a platelet aggregation inhibitory activity as the pharmacological activity but are not carbostyril derivatives, are disclosed in Japanese Patent Kokai (Laid-Open) No. 55-2655 (1980) (quinoline type compounds), Japanese Patent Kokai (Laid-Open) No. 54-115370 (1979) (oxyindole type compounds), Japanese Patent Kokai (Laid-Open) No. 57-14578 (1982) (benzimidazole-2-one type compounds), Japanese Patent Kokai (Laid-Open) No. 57-209281 (1982) (benzoxazine type compounds), Japanese Patent Kokai (Laid-Open) No. 55-36444 (1980) (thiocarbostyril type compounds), etc.

Further, those carbostyril derivatives having no side chain similar to the side chain of the carbostyril derivative of the present application, represented by the formula

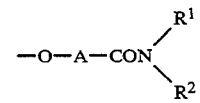

but having a platelet aggregation inhibitory activity as the pharmacological activity, for example, tetrazole-substituted alkoxycarbostyril derivatives are disclosed in U.S. Pat. No. 4,277,479, British Patent No. 2,033,893 and German Patent No. 2934747, and heterocycle-substituted alkoxycarbostyril derivatives are disclosed in European Patent Publication No. 0240015. Besides, those carbostyril derivatives having a side chain represented by the formula

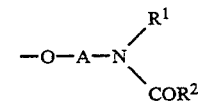

and having a platelet aggregation inhibitory activity, are disclosed in Japanese Patent Kokai (Laid-Open) No. 57-14574 (1982).

Further, U.S. Pat. No. 3,682,920 discloses 3,4-dihydrocarbostyril derivatives having a substituent at the 1-position which are useful as an analgesic.

However, the known carbostyril derivatives having a side chain represented by the formula

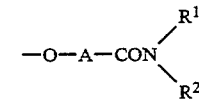

have had a drawback in that they increase circulation activities such as heart rate increasing activity and the like.

DISCLOSURE OF THE INVENTION

The present inventors made extensive research in order to develop a novel carbostyril derivative which is low in the side effects exhibited by the above known carbostyril derivatives, particularly the side effects of circulation activities. As a result, the novel carbostyril compounds of the present invention have excellent platelet aggregation inhibitory activity, a phosphodiesterase inhibitory activity, a venticular contraction activity (a positive contraction activity), an anti-ulcer activity, an anti-inflammatory activity, a cerebral blood flow increasing activity, a thrombus dissociation activity, a thromboxane $A_2$ antagonism activity, etc. The compound of the present invention is characterized in that it exhibits the above activities for a long time, is low in toxicity (particularly low in toxicity to hearts of cardiovascular hyperplasia, myocardiopathy, etc.), and is low in circulation activities such as heart rate increasing activity, blood pressure decreasing activity and the like. Also, the compound of the present invention has the advantage that it is easily absorbed by the intestinal tract and easily migrates into blood. Therefore, the carbostyril compounds of the present invention can be used most suitably as a preventive and remedy for thrombi such as apoplexia, cerebral infarction, myocardial infarction and the like, a cerebral circulation improving agent, an antiinflammatory agent, an antiasthmatic agent, a cardiotonic agent and a phosphodiesterase inhibitory agent.

According to the present invention, there are provided novel carbostyril compounds or salt thereof represented by the following general formula (1)

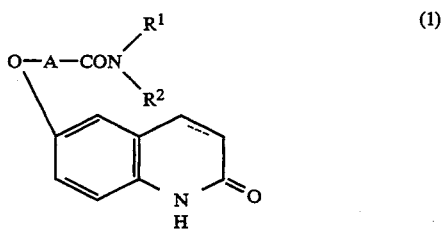

[In the formula, A represents a lower alkylene group; $R^1$ represents a cycloalkyl-lower alkyl group which may have, as a substituent, a group selected from the group consisting of lower alkoxycarbonyl groups, a carboxy group, lower alkanoyloxy-lower alkyl groups, amino-lower alkyl groups, lower alkylamino-lower alkyl groups and hydroxy-lower alkyl groups, a cycloalkyl group, a tetrahydropyranyl-lower alkyl group, a lower alkylene-dioxy group-substituted lower alkyl group, a phenyl-lower alkyl group having, as substituent(s) on the phenyl ring, 1-3 groups selected from the group consisting of lower alkyl groups and a hydroxyl group, or a piperidinyl-lower alkyl group having a lower alkyl group as a substituent; $R^2$ is a 5-membered or 6-membered saturated or unsaturated heterocycle-lower alkyl group which may have, as substituent(s) on the heterocycle, 1-3 groups selected from the group consisting of hydroxy-lower alkyl groups, lower alkanoyloxy-lower alkyl groups, a hydroxyl group, lower alkyl groups, amino-lower alkyl groups, lower alkylamino-lower alkyl groups, lower alkoxy groups, lower alkoxy-lower alkoxy groups, lower alkoxy-lower alkyl groups, a thio group and lower alkylamido groups, a tetrahydropyranyltho-lower alkyl group, a pyridylthio-lower alkyl group, a lower alkylene-dioxy group-substituted lower alkyl group, or a lower alkyl group which may have, as substituent(s), 1-2 groups selected from the group consisting of an amino group, a hydroxyl group, lower alkylthio groups, lower alkanoyloxy groups, a tetrahydropyranyloxy group, halogen atoms, lower alkanoyl groups, a mercapto group, lower alkoxycarbonyl groups, a carboxy group, lower alkoxy groups, an amide group and lower alkylamido groups, wherein the amino group as a substituent for the lower alkyl group may have, as a substituent, a lower alkanoyl group, a phenyl-lower alkyl group which may have a lower alkoxy group as a substituent on the phenyl ring, a lower alkenyl group, a hydroxy-lower alkyl group or a lower alkyl group; where $R^2$ represents a lower alkyl group which may have 1-2 hydroxyl groups, a lower alkyl group having a lower alkanoyloxy group, or a lower alkyl group having a lower alkoxy group, $R^1$ should not be any of a cycloalkyl-lower alkyl group, a cycloalkyl group and a tetrahydropyranyl-lower alkyl group and the carbon-carbon bond between 3- and 4-positions in the carbostyril skeleton represents a single bond or a double bond. There is also provided, a process for producing said compound, and a pharmaceutical composition for inhibiting platelet aggregation which contains, as an active ingredient, a carbostyril compound represented by the above general formula (1).

BEST MODE FOR CARRYING OUT THE INVENTION

In the present specification, each of the groups represented by $R^1$, $R^2$ and A in the general formula (1) is specifically as follows.

As to the lower alkylene group, there can be mentioned straight chain or branched chain alkylene groups of 1-6 carbon atoms, such as methylene, ethylene, methylmethylene, trimethylene, 2-methyltrimethylene, 2,2-dimethyltrimethylene, tetramethylene, pentamethylene, hexamethylene, 2-ethyltrimethylene, 1-methyltrimethylene and the like.

As to the lower alkoxycarbonyl group, there can be mentioned alkoxycarbonyl groups whose alkoxy portions are each a straight chain or branched chain alkoxy group of 1-6 carbon atoms, such as methoxycarbonyl, ethoxycarbonyl, propoxycarbonyl, isopropoxycarbonyl, butoxycarbonyl, pentyloxycarbonyl, hexyloxycarbonyl and the like.

As to the lower alkanoyloxy-lower alkyl group, there can be mentioned alkanoyloxyalkyl groups whose alkanoyl portions are each a straight chain or branched chain alkanoyl group of 2-6 carbon atoms and whose alkyl portions are each a straight chain or branched chain alkyl group of 1-6 carbon atoms, such as acetyloxymethyl, 2-acetyloxyethyl, 3-acetyloxypropyl, 4-acetyloxybutyl, 5-acetyloxypentyl, 6-acetyloxyhexyl, 1-methyl-2-acetyloxyethyl, 2-acetyloxypropyl, 1,1-dimethyl-2-acetyloxyethyl, 2-propionyloxyethyl, 3-propionyloxypropyl, 4-propionyloxybutyl, 5-propionyloxypentyl, 6-propionyloxyhexyl, 2-propionyloxypropyl, 2-butyryloxyethyl, 3-butyryloxypropyl, 4-butyryloxybutyl, 2-butyryloxypropyl, 2-diobutyryloxyethyl, 4-isobutyryloxybutyl, 2-pentanoyloxyethyl, 5-pentanoyloxypentyl, 2-tert-butylcarbonyloxyethyl, 2-hexanoyloxyethyl, 6-hexanoyloxyhexyl and the like.

As to the amino-lower alkyl group, there can be mentioned straight chain or branched chain alkyl groups of 1-6 carbon atoms having an amino group as a substituent, such as aminomethyl, 1-aminoethyl, 2-aminoethyl, 3-aminopropyl, 4-aminobutyl, 5-aminopentyl, 6-aminohexyl, 1,1-dimethyl-2-aminoethyl, 2-methyl-3-aminopropyl and the like.

As to the lower alkylamino-lower alkyl group, there can be mentioned straight chain or branched chain alkyl groups of 1-6 carbon atoms having, as an substituent, an amino group substituted by 1-2 straight chain or branched chain alkyl groups of 1-6 carbon atoms, such as methylaminomethyl, ethylaminomethyl, propylaminomethyl, isopropylaminomethyl, butylaminomethyl, tert-butylaminomethyl, pentylaminomethyl, hexylaminomethyl, dimethylaminomethyl, diethylaminomethyl, dipropylaminomethyl, dibutylaminomethyl, dipentylaminomethyl, dihexylaminomethyl, N-methyl-N-ethylaminomethyl, N-methyl-N-butylaminomethyl, N-ethyl-N-propylaminomethyl, N-methyl-N-hexylaminomethyl, 2-methylaminoethyl, 1-ethylaminoethyl, 3-propylaminopropyl, 4-butylaminobutyl, 1,1-dimethyl-2-pentylaminoethyl, 5-hexylaminopentyl, 6-dimethylaminohexyl, 2-diethylaminoethyl, 1-(N-methyl-N-hexylamino)ethyl, 3-dihexylaminopropyl, 4-dibutylaminobutyl, 2-(N-methyl-N-pentylamino)ethyl and the like.

As to the hydroxy-lower alkyl group, there can be mentioned hydroxyalkyl groups whose alkyl portions are each a straight chain or branched chain alkyl group of 1-6 carbon atoms; for example, hydroxymethyl, 2-hydroxyethyl, 1-hydroxyethyl, 3-hydroxypropyl, 4-hydroxybutyl, 1,1-dimethyl-2-hydroxyethyl, 5-hydroxypentyl, 6-hydroxyhexyl, 2-methyl-3-hydroxypropyl and the like.

As to the cycloalkyl group, there can be mentioned cycloalkyl groups of 3-8 carbon atoms, such as cyclopropyl, cyclobutyl, cyclopentyl, cyclohexyl, cycloheptyl, cyclooctyl, cyclononanyl, cyclodecanyl and the like.

As to the tetrahydropyranyl-lower alkyl group, there can be mentioned tetrahydropyranylalkyl groups whose alkyl portions are each a straight chain or branched chain alkyl group of 1-6 carbon atoms; for example, (2-tetrahydropyranyl)methyl, (3-tetrahydropyranyl)methyl, (4-tetrahydropyranyl)methyl, 2-(2-tetrahydropyranyl)ethyl, 2-(3-tetrahydropyranyl)ethyl, 2-(4-tetrahydropyranyl)ethyl, 1-(2-tetrahydropyranyl)ethyl, 1-(3-tetrahydropyranyl)ethyl, 1-(4-tetrahydropyranyl)ethyl, 3-(2tetrahydropyranyl)propyl, 3-(3-tetrahydropyranyl)propyl, 3-(4-tetrahydropyranyl)propyl, 4-(2-tetrahydropyranyl)butyl, 4-(3-tetrahydropyranyl)butyl, 4-(4-tetrahydropyranyl)butyl, 1,1-dibutyl-2-(2-tetrahydropyranyl)ethyl, 1,1-dimethyl-2-(3-tetrahydropyranyl)ethyl, 1,1-dimethyl-2-(4-tetrahydropyranyl)ethyl, 5-(2-tetrahydropyranyl)pentyl, 5-(3-tetrahydropyranyl)pentyl, 5-(4-tetrahydropyranyl)pentyl, 6-(2-tetrahydropyranyl)hexyl, 6-(3-tetrahydropyranyl)hexyl, 6-(4-tetrahydropyranyl)hexyl, 2-methyl-3-(2-tetrahydropyranyl)propyl, 2-methyl-3-(3-tetrahydropyranyl)propyl, 2-methyl-3-(4-tetrahydropyranyl)propyl and the like.

As to the lower alkylenedioxy group, there can be mentioned straight chain or branched chain alkylenedioxy groups of 1-4 carbon atoms, such as methylenedioxy, ethylenedioxy, trimethylenedioxy, tetramethylenedioxy and the like.

As to the lower alkylenedioxy group-substituted lower alkyl group, there can be mentioned alkylenedioxy group-substituted alkyl groups whose alkylenedioxy portions are each a straight chain or branched chain alkylenedioxy group of 1-3 carbon atoms and whose alkyl portions are each a straight chain or branched chain alkyl group of 1-6 carbon atoms; for example, 2,3-dimethylmethylenedioxy-1-propyl, 2,4-methylenedioxy-1-butyl, 1,3-dimethylmethylenedioxy-2-propyl, 1,1-ethylenedioxymethyl, 1,2-methylenedioxy-1-ethyl, 4,5-trimethylenedioxy-1-pentyl, 2,3-ethylenedioxy-1-hexyl and the like.

As to the lower alkyl group, there can be mentioned straight chain or branched chain alkyl groups of 1-6 carbon atoms, such as methyl, ethyl, propyl, isopropyl, butyl, tert-butyl, pentyl, hexyl and the like.

As to the phenyl-lower alkyl group having, as substitutent(s) on the phenyl ring, 1-3 groups selected from the group consisting of lower alkyl groups and a hydroxyl group, there can be mentioned phenylalkyl groups whose alkyl portions are each a straight chain or branched chain alkyl group of 1-6 carbon atoms and which have on each phenyl ring 1-3 groups selected from the group consisting of straight chain or branched chain alkyl groups of 1-6 carbon atoms and a hydroxyl group; for exmaple, 2-(3-methylphenyl) ethyl, 1-(4-methylphenyl)ethyl, 2-methylbenzyl, 3-(2-ethylphenyl) propyl, 4-(3-ethylphenyl)butyl, 1,1-dimethyl-2-(4-ethylphenyl)ethyl, 5-(4-isopropylphenyl)pentyl, 6-(4-hexylphenyl)hexyl, 3,4-dimethylbenzyl, 3,4,5-trimethylbenzyl, 2,5-dimethylbenzyl, 2-hydroxybenzyl, 2-(3-hydroxyphenyl)ethyl, 3-(2-hydroxyphenyl)propyl, 4-(3-(hydroxyphenyl)butyl, 5-(4-hydroxyphenyl)pentyl, 6-(4-hydroxyphenyl)hexyl, 3,5-di-tert-butyl-4-hydroxybenzyl, 2,4-dihydroxybenzyl, 2,4,6-trihydroxybenzyl, 2,6-dimethyl-4-hydroxybenzyl and the like.

As to the piperidinyl-lower alkyl group having a lower alkyl group as a substituent, there can be mentioned piperidinylalkyl groups which each have 1-3 straight chain or branched chain alkyl groups of 1-6 carbon atoms as substituent(s) and whose alkyl portions are each a straight chain or branched chain alkyl group of 1-6 carbon atoms; for example, (1-methyl-3-piperidinyl)methyl, 2-(1-ethyl-4-piperidinyl)ethyl, 1-(1-propyl-2-piperidinyl)ethyl, 3-(1-isopropyl-3-piperidinyl)propyl, 4-(1-isopropyl-4-piperidinyl)butyl, 5-(1-butyl-3-piperidinyl)pentyl, 6-(1-pentyl-2-piperidinyl)hexyl, 1,1-dimethyl-2-(1-hexyl-2-piperidinyl)ethyl, 2-methyl-3-(1-methyl-3-piperidinyl)-propyl, 2-(2,6-dimethyl-1-piperidinyl)ethyl, 3-(4-methyl-1-piperidinyl)propyl, (2,4,6-trimethyl-1-piperidinyl)-methyl, 1-(2-ethyl-1-piperidinyl)ethyl, 4-(4-tert-butyl-1-piperidinyl)butyl, 5-(3-pentyl- 1-piperdinyl)pentyl, 6-(4-hexyl-1-piperidinyl)hexyl and the like.

As to the lower alkoxy group, there can be mentioned straight chain or branched chain alkoxy groups of 1-6 carbon atoms, such as methoxy, ethoxy, propoxy, isopropoxy, butoxy, tert-butoxy, pentyloxy, hexyloxy and the like.

As to the lower alkoxy-lower alkoxy group, there can be mentioned alkoxyalkoxy groups whose alkoxy portions are each a straight chain or branched chain alkoxy group of 1-6 carbon atoms, such as methoxymethoxy, 3-methoxypropoxy, 4-ethoxybutoxy, 6-propoxyhexyloxy, 5-isoporpoxypentyloxy, 1,1-dimethyl-2-butoxyethoxy, 2-mthyl-tert-butoxypropoxy, 2-pentyloxyethoxy, hexyloxymethoxy and the like.

As to the lower alkoxy-lower alkyl group, there can be mentioned alkoxyalkyl groups whose alkoxy portions are each a straight chain or branched chain alkoxy group of 1-6 carbon atoms and whose alkyl portions are each a straight chain or branched chain alkoxy group of 1-6 carbon atoms; for example, methoxymethyl, hexyloxymethyl, 2-pentyloxyethyl, 3-methoxypropyl, 4-ethoxybutyl, 5-isopropoxypentyl, 6-propoxyhexyl, 1,1-dimethyl-2-butoxyethyl, 2-methyl-tert-butoxypropyl and the like.

As to the lower alkylamideo group, there can be mentioned amido groups each having 1-2 straight chain or branched chain alkyl groups of 1-6 carbon atoms, such as methylamido, ethylamido, propylamido, isopropylamido, butylamido, tertbutylamido, pentylamido, hexylamido, N-ethyl-N-hexylamido, N-methyl-N-ethylamido, N-methyl-N-propylamido, N-methyl-N-butylamido and the like.

As to the tetrahydropyranylthio-lower alkyl group, there can be mentioned tetrahydropyranylthioalkyl groups whose alkyl portions are each a straight chain or branched chain alkyl group of 1-6 carbon atoms; for example, (2-tetrahydropyranylthio)methyl, (3-tetrahydropyranylthio)methyl, (4-tetrahydropyranylthio)methyl, 2-(2-tetrahydropyranylthio)ethyl, 2-(3-tetrahydropyranylthio)ethyl, 2-(4-tetrahydropyranylthio)ethyl, 1-(2-tetrahydropyranylthio)ethyl, 1-(3-tetrahydropyranylthio)ethyl, 1-(4-tetrahydropyranylthio)ethyl, 3-(2-tetrahydropyranylthio)propyl, 3-(3-tetrahydropyranylthio)propyl, 3-(4-tetrahydropyranylthio)propyl, 4-(2-tetrahydroipyranylthio)butyl, 4-(3-tetrahydropyranylthio)butyl, 4-(4-tetrahydropyranylthio)butyl, 1,1-dimethyl-2-(2-tetrahydropyranylthio)ethyl, 1,1-dimethyl-2-(3-tetrahydropyranylthio)ethyl, 1,1-dimethyl-2-(4-tetrahydropyranylthio)ethyl, 5-(2-tetrahydropyranylthio)pentyl, 5-(3-tetrahydropyranylthio)pentyl, 5-(4-tetrahydropyranylthio)pentyl, 6-(2-tetrahydropyranylthio)hexyl, 6-(3-tetrahydropyranylthio)hexyl, 6-(4-tetrahydropyranylthio)hexyl, 2-methyl-3-(2-tetrahydropyranylthio)propyl, 2-methyl-3-(3-tetrahydropyranylthio)propyl, 2-methyl-3-(4-tetrahydropyranylthio)propyl and the like.

As to the pyridylthio-lower alkyl group, there can be mentioned pyridylthioalkyl groups whose alkyl portions are each a straigh chain or branched chain alkyl group of 1-6 carbon atoms; for example, (2-pyridylthio)methyl, (3-pyridylthio)methyl, (4-pyridylthio)methyl, 2-(2-pyridylthio)ethyl, 2-(3-pyridylthio)ethyl, 2-(4-pyridylthio)ethyl, 1-(2-pyridylthio)ethyl, 1-(3-pyridylthio)ethyl, 1-(4-pyridylthio)ethyl, 3-(2-pyridykthio)propyl, 3-(3-pyridylthio)propyl, 3-(4-pyridylthio)propyl, 4-(2-pyrdidylthio)butyl, 4-(3-pyridylthio)butyl, 4-(4-pyridylthio)butyl, 1,1-dimethyl-2-(2-pyridylthio)ethyl, 1,1-dimethyl-2-(3-pyridylthio)ethyl, 1,1-dimethyl-2-(4-pyridylthio)ethyl, 5-(2-pyridylthio)pentyl, 5-(3-pyridylthio)pentyl, 5-(4-pyrdidylthio)pentyl, 6-(2-pyridylthio)hexyl, 6-(3-pyridylthio)hexyl, 6-(4-pyridylthio)hexyl, 2-methyl-3-(2-pyridylthio)propyl, 2-methyl-3-(3-pyridylthio)propyl, 2-methyl-3-(4-pyridylthio)propyl and the like.

As to the lower alkylthio group, there can be mentioned straight chain or branched chain alkylthio groups of 1-6 carbon atoms, such as methylthio, ethylthio, propylthio, isopropylthio, butylthio, tert-butylthio, pentylthio, hexylthio and the like.

As to the lower alkanoyloxy group, there can be mentioned straight chain or branched chain alkanoyloxy groups of 2-6 carbon atoms, such as acetyloxy, proipionyloxy, butyryloxy, isobutyryloxy, pentanoyloxy, tert-butylcarbonyloxy, hexanoyloxy and the like.

As to the halogen atom, there can be mentioned, for example, a fluorine atom, a chlorine atom, a bromine atom and an iodine atom.

As to the lower alkanoyl group, there can be mentioned straight chain or branched chain alkanoyl groups of 1-6 carbon atoms, such as formyl, acetyl, propionyl, butyryl, iosbutyryl, pentanoyl, tert-butylcarbonyl, hexanoyl and the like.

As to the phenyl-lower alkyl group which may have a lower alkoxy group as a substituent on the phenyl ring, there can be mentioned phenylalkyl groups whose alkyl portions are each a straight chain or branched chain alkyl group of 1-6 carbon atoms and which may have 1-3 straight chain or branched chain alkoxy groups of 1-6 carbon atoms on each phenyl ring; for example, benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-(3-methoxyphenyl)ethyl, 1-(4-methoxyphenyl)ethyl, 2-methoxybenzyl, 3-(2-ethoxyphenyl)propyl, 4-(3-ethoxyphenyl)butyl, 1,1-dimethyl-2-(4-ethoxyphenyl)ethyl, 5-(4-isopropoxyphenyl)pentyl, 6-(4-hexyloxyphenyl)hexyl, 3,4-dimethoxybenzyl, 3,4,5-trimethoxybenzyl, 2,5-dimethoxybenzyl and the like.

As to the lower alkenyl group, there can be mentioned straight chain or branched chain alkenyl groups of 2-6 carbon atoms, such as vinyl, allyl, 2-butenyl, 3-butenyl, 1-methylallyl, 2-pentenyl, 2-hexenyl and the like.

As to the cycloalkyl-lower alkyl group which may have, as a substituent, a group selected from the group consisting of lower alkoxycarbonyl groups, a carboxy group, lower alkanoyloxy-lower alkyl groups, amino-lower alkyl groups, lower alkylamino-lower alkyl groups and hydroxy-lower alkyl groups, there can be mentioned cycloalkylalkyl groups whose cycloalkyl portions are each a cycloalkyl group of 3-8 carbon atoms and whose alkyl portions are each a straight chain or branched chain alkyl group of 1-6 carbon atoms and which may each have, as a substituent, a group selected from the group consisting of alkoxycarbonyl groups whose alkoxy portions are each a straight chain or branched chain alkoxy group of 1-6 carbon atoms, a carbonyl group, alkanoyloxyalkyl groups whose alkanoyl portions are each a straight chain or branched chain alkanoyl group of 2-6 carbon atoms and whose alkyl portions are each a straight chain or branched chain alkyl group of 1-6 carbon atoms, stright chain or branched chain alkyl groups of 1-6 carbon atoms each having an amino group as a substituent, straight chain or branched chain alkyl groups of 1-6 carbon atoms having, as a substituent, an amino group substituted by 1-2 straight chain or branched chain alkyl groups of 1-6 carbon atoms, and hydroxyalkyl groups whose alkyl portions are each a straight chain or branched chain alkyl group of 1-6 carbon atoms; for example, 4-cyclohexylbutyl, cyclopropylmethyl, 2-cyclopentylethyl, cyclohexylmethyl, 2-cyclopentylpropyl, 3-cyclohexylpropyl, cyclopentylmethyl, 2-cyclohexylethyl, 2-cyclohexylpropyl, 2-cycloheptylethyl, 3-cyclobutylpropyl, 1,1-dimethyl-2-cyclohexylethyl, 1-methyl-2-cyclopentylethyl, 2-cyclooctylethyl, 5-cyclohexylpentyl, 6-cyclohexylhexyl, 4-(3-methoxycarbonylcyclohexyl)butyl, (4-ethoxycarbonylcyclohexyl)methyl, (2-propoxycarbonylcyclopropyl)methyl, 2-(2-isopropoxycarbonylcyclopentyl)ethyl, 2-(3-butoxycarbonylcyclopentyl)propyl, 3-(2-pentyloxycarbonylcyclohexyl)propyl, 2-(4-hexyloxycarbonylcycloheptyl)ethyl, 3-(2-methoxycarbonylcyclobutyl)propyl, 1,1-dimethyl-2-(3-ethoxycarbonylcyclohexyl)ethyl, 1-methyl-2-(3-propoxycarbonylcyclopentyl)ethyl, 2-(3-isopropoxycarbonylcyclooctyl)ethyl, 5-(4-ethoxycarbonylcyclohexyl)pentyl, 6-(3-ethoxycarbonylcyclohexyl)hexyl, 4-(4-carboxycyclohexyl)butyl, (2-carboxycyclopentyl)methyl, 2-(2-carboxycyclopentyl)ethyl, (4-carboxycyclohexyl)methyl, 3-(2-carboxycyclohexyl)propyl, 2-(3-carboxycyclohexyl)ethyl, 2-(4-carboxycyclohexyl)ethyl, 2-(4-carboxycycloheptyl)ethyl, 3-(2-carboxycyclobutyl)propyl, 1,1-dimethyl-2-(4-carboxycyclohexyl)ethyl, 1-methyl-2-(3-carboxycyclopentyl)ethyl, 2-(3-carboxycyclooctyl)ethyl, 5-(4-carboxycyclohexyl)pentyl, 6-(2-carboxycyclohexyl)hexyl, (4-acetyloxycyclohexyl)methyl, 4-[3-(2-propionyloxyethyl)cyclohexyl]butyl, 2-[3-(3-butyryloxypropyl)cyclopentyl]ethyl, 3-[3-(4-isobutyryloxybutyl)cyclobutyl]propyl, 2-[4-(5-pentanoyloxypentyl)cycloheptyl]ethyl, 2-[3-(6hexanoyloxyhexyl)cyclooctyl]ethyl, (4-dimethylaminomethylcyclohexyl)methyl, 4-(4-aminomethylcyclohexyl)butyl, (2-methylaminomethylcyclopropyl)methyl, 5-[3-(3-propylaminopropyl)cyclopentyl]pentyl, 6-[4-(4-butylaminobutyl)cyclopentyl]hexyl, 3-[4-(1,1-dimethyl-2-pentylaminoethyl)cyclopentyl]propyl, [3-(5-hexylaminopentyl)cyclopentyl]methyl, 2-[4-(6-dimethylaminohexyl)cyclohexyl]ethyl, 2-[3-(2-diethylaminoethyl)cyclohexyl]propyl, 1,1-dimethyl-2-{4-[1-(N-methyl-N-hexylamino)ethyl]cyclohexyl}etyl, 1-methyl-2-[4-(3-dihexylaminopropyl)cyclopentyl]ethyl, 2-[3-(4-dibutylaminobutyl)cyclooctyl]ethyl, 2- {3-[2-(N-methyl-N-pentylamino)ethyl]bycloheptyl}ethyl, 3-[2-(1-ethylaminoethyl)cyclobutyl]propyl, (4-hydroxymethylcyclohexyl)methyl, 4-[3-(2-hydroxyethyl)cyclohexyl]butyl, [2-(1-hydroxyethyl)cyclopropyl]methyl, 2-[3-(3-hydroxypropyl)cyclopentyl]ethyl, 3-[4-(4-hdyroxybutyl)cyclopentyl]propyl, 3-[2-(1,1-dimethyl-2-hdyroxyethyl)cyclobutyl]propyl, 2-[3-(5-hydroxypentyl)cycloheptyl]ethyl, 2-[3-(6-hydroxyhexyl)cyclooctyl]ethyl, 6-[4-(2-methyl-3-hydroxypropyl)cyclohexyl]hexyl, 5-(2-hydroxymethylcyclopentyl)pentyl and the like.

As to the amino group which may have, as a substituent, a lwoer alkanoyl group, a phenyl-lower alkyl group which may have a lower alkoxy group as a substituent on the phenyl ring, a lower alkenyl group, a hydroxy-lower alkyl group or a lower alkyl group, there can be mentioned amino group which may each have, as substituent(s), 1-2 groups selected from straight chain or branched chain alkanoyl groups of 1-6 carbon atoms, phenylalkyl groups which may each have 1-3 straight chain or branched chain alkoxy groups of 1-6 carbon atoms on the phenyl ring and whose alkyl portions are each straight chain or branched chain alkyl groups of 1-6 carbon atoms, straight chain or branched chain alkenyl groups of 2-6 carbon atoms, hydroxyalkyl groups whose alkyl portions are each a straight chain or branched chain alkyl group of 1-6 carbon atoms and straight chain or branched chain alkyl groups of 1-6 carbon atoms; for example, amino, formylamino, acetylamino, propionylamino, butyrylamino, isobutyrylamino, pentanoylamino, tert-butylcarbonylamino, hexanoylamino, [2-(3,4-dimethoxyphenyl)ethyl]amino, benzylamino, N-ethyl-N-benzylamino, N-ethyl-N-[2-(3,4-dimethoxyphenyl)ethyl]amino, (1-phenylethyl)amino, [3-(2-ethoxyphenyl)propyl]amino, (4-phenylbutyl)amino, [5-(4-isopropoxyphenyl)pentyl]amino, [6-(4-hexyloxyphenyl)hexyl]amino, (3,4,5-trimethoxybenzyl)amino, N-methyl-N-benzylamino, N-propyl-N-[2-(3,4-dimethoxyphenyl)ethyl]amino, N-butyl-N-(2-phenylethyl)amino, N-pentyl-N-(3-phenylpropyl)amino, N-hexyl-N-(5-phenylpentyl)amino, allylamino, N-ethyl-N-allylamino, N(2-butenyl)amino, N-methyl-N-(3-butenyl)amino, N-(1-methylallyl)amino, N-(2-pentenyl)-N-propylamino, N-butyl-N-(2-hexenyl)amino, hydroxyemthylamino, N-(2-hydroxyethyl)-N-ethylamino, (1-hydroxyethyl)amino, N-methyl-N-(3-hydroxypropyl)amino, N-propyl-N-(4-hydroxybutyl)amino, (1,1-dimethyl-2-hydroxyethyl)amino, N-butyl-N-(5-hydroxypentyl)amino, (6-hydroxyhexyl)amino, N-pentyl-N-(2-methyl-3-hydroxypropyl)amino, N-hexyl-N-(2-hydroxyethyl)amino, methylamino, ethylamino, propylamino, isopropylamino, butylamino, tert-butylamino, pentylamino, hexylamino, dimethylamino, diethylamino, diproipylamino, dibutylamino, dipentylamino, dihexylamino, N-methyl-N-ethylamino, N-ethyl-N-propylamino, N-methyl-N-butylamino, N-methyl-N-hexylamino and the like.

As to the 5-membered or 6-membered saturated or unsaturated heterocycle-lower alkyl group which may have, as a substituent on the heterocycle, 1-3 groups selected from the group consisting of hydroxy-lower alkyl groups, lower alkanoyloxy-lower alkyl groups, a hydroxyl group, lower alkyl groups, amino-lower alkyl groups, lower alkylamino-lower alkyl groups, lower alkoxy groups, lower alkoxy-lower alkoxy groups, lower alkoxy-lower alkyl groups, a thio group and lower alkylamide groups, there can be mentioned 5-membered or 6-membered saturated or unsaturated heterocycle-alkyl groups which may each have, as substituent(s(on the heterocycle, 1-3 groups selected from the group consisting of hydroxyalkyl groups whose alkyl portions are each a straight chain or branched chain alkyl group of 1-6 carbon atoms, alkanoyloxyalkyl groups whose alkanoyl portions are each a straight chain or branched chain alkanoyl group of of 2-6 carbon atoms and whose alkyl portions are each a straight chain or branched chain alkyl groups of 1-6 carbon atoms, a hydroxyl group, straight chain or branched chain alkyl groups of 1-6 carbon atoms, straight chain or branched chain alkyl groups of 1-6 carbon atoms having an amino group as a substituent, straight chain or branched chain alkyl groups of 1-6 carbon atoms substituted by an amino group having 1-2 straight chain or branched chain alkyl groups of 1-6 carbon atoms, straight chain or branched chain alkoxy groups of 1-6 carbon atoms, alkoxyalkoxy groups whose alkoxy portions are each a straight chain or branched chain alkoxy group of 1-6 carbon atoms, alkoxyalkyl groups whose alkoxy portions are each a straight chain or branched chain alkoxy group of 1-6 carbon atoms and whose alkyl portions are each a straight chain or branched chain alkyl group of 1-6 carbon atoms, a thio group and alkylamido groups whose alkyl portions are each a straight chain or branched alkyl group of 1-6 carbon atoms; for example, (1-pyrrolidinyl)methyl, 2-(1-pyrrolidinyl)ethyl, 1-(1-pyrrolidinyl)ethyl, 3-(2-pyrrolidinyl)propyl, 4-(3-pyrrolidinyl)butyl, 1,1-dimethyl-2-(1-pyrrolidinyl)ethyl, 5-(2-pyrrolidinyl)pentyl, 6-(3-pyrrolidinyl)hexyl, 2-methyl-3-(1-pyrrolidinyl)propyl, 2-(2-hydroxyemthyl-1-pyrrolidinyl)ethyl, 2-(2-acetyloxymethyl-1-pyrrolidinyl)ethyl, 2-(3-hdyroxy-1-pyrrolidinyl)ethyl, morpholinomethyl, 2-morpholinoethyl, 1-morpholinoethyl, 3-morpholinopropyl, 4-morpholinobutyl, 1,1-dimethyl-2-morpholinoethyl, 5-morpholinopentyl, 6-morpholinohexyl, 2-methyl-3-morpholinopropyl, (1-piperidinyl)methyl, 2-(1-piperidinyl)ethyl, 1-(2-piperidinyl)ethyl, 3-(3-piperidinyl)propyl, 4-(1-piperidinyl)butyl, 1,1-dimethyl-2-(2-piperidinyl)ethyl, 5-(3-piperidinyl)pentyl, 6-(4-piperidinyl)hexyl, 2-methyl-3-(1-piperidinyl)propyl, 2-(4-hydroxy-1-piperidinyl)ethyl, 2-(2,6-dimethyl-1-piperidinyl)ethyl, 2-(2-dimethylaminomethyl-1-pyrrolidinyl)ethyl, 2-(4-methoxy-1-piperidinyl)ethyl, 2-(2-hydroxyemthyl-4-hdyroxy-1-pyrrolidinyl)ethyl, 2-(1-ethyl-4-hydroxy-2-pyrrolidinyl)ethyl, 2-(2-methoxymethyl-1-pyrrolidinyl)ethyl, 2-(4-methoxymethoxy-1-piperidinyl)ethyl, (1-thiomorpholino)methyl, 2-(2-thiomorpholino)ethyl, 1-(3-thiomorpholino)ethyl, 3-(1-thiomorpholino)propyl, 4-(2-thiomorpholino)butyl, 1,1-dimethyl-2-(1-thiomorpholino)ethyl, 5-(2-thiomorpholino)pentyl, 6-(3-thiomorpholino)hexyl, 2-methyl-3-(2-thiomorpholino)propyl, (1-imidazolyl)methyl, 2-(1-imidazolyl)ethyl, 1-(1-imidazolyl)ethyl, 3-(1-imidazolyl)propyl, 4-(1-imidazolyl)butyl, 1,1-dimethyl-2-(1-imidazolyl)ethyl, 5-(1-imidazolyl)pentyl, 6-(1-imidazolyl)hexyl, 2-methyl-3-(1-imidazolyl)propyl, (1,2,4-triazol-1-yl)methyl, 2-(1,2,4-triazol-1-yl)ethyl, 1-(1,2,4-triazol-1-yl)ethyl, 3-(1,2,4-triazol-1-yl)propyl, 4-(1,2,4-triazol-1-yl)butyl, 1,1-dimethyl-2-(1,2,4-triazol-1-yl)ethyl, 5-(1,2,4-triazol-1-yl)pentyl, 6-(1,2,4-triazol-1-yl)hexyl, 2-methyl-3-(1,2,4-triazol-1-yl)propyl, (1,6-dimethyl-2-thiomorpholino)methyl, (2-furyl)methyl, 2-(2-furyl)ethyl, 1-(2-furyl)ethyl, 3-(3-furyl)propyl, 4-(2-furyl)butyl, 1,1-dimethyl-2-(3-furyl)ethyl, 5-(2-furyl)pentyl, 6-(3-furyl)hexyl, 2-methyl-3-(2-furyl)propyl, 2-(2-diethylamido-1-pyrrolidinyl)ethyl, (1-methyl-3-piperidinyl)methyl, (1-methyl-2-piperidinyl)methyl, (1-piperazinyl)methyl, 2-(1-piperazinyl)ethyl, 1-(1-piperazinyl)ethyl, 3-(1-piperazinyl)propyl, 4-(1-piperazinyl)butyl, 1,1-dimethyl-2-(1-piperazinyl)ethyl, 5-(1-piperazinyl)pentyl, 6-(1-piperazinyl)hexyl, 2-methyl-3-(1-piperazinyl)propyl, 2-[4-(2-hydroxyethyl)-1-piperazinyl]ethyl, 2-(4-methyl-1-piperazinyl)ethyl, 2-[4-(2-acetyloxyethyl)-1-piperazinyl]ethyl, (1,2,3,4-tetrazol-1-yl)methyl, 2-(1,2,3,4-tetrazol-1-yl)ethyl, 1-(1,2,3,4-tetrazol-1-yl)ethyl, 3-(1,2,3,4-tetrazol-1-yl)propyl, 4-(1,2,3,4-tetrazol-1-yl)butyl, 5-(1,2,3,4-tetrazol-1-yl)pentyl, 6-(1,2,3,4-tetrazol-1-yl)hexyl, (2-pyridyl)methyl, 2-(2-pyridyl)ethyl, 1-(2-pyridyl)ethyl, 3-(2-pyridyl)propyl, 4-(2-pyridyl)butyl, 1,1-dimethyl-2-(2-pyridyl)ethyl, 5-(2-pyridyl)pentyl, 6-(2-pyridyl)hexyl, 2-methyl-3-(2-pyridyl)propyl, (3-pyridyl)methyl, 2-(3-pyridyl)ethyl, 1-(3-pyridyl)ethyl, 3-(3-pyridyl)propyl, 4-(3-pyridyl)butyl, 1,1-dimethyl-2-(3-pyridyl)ethyl, 5-(3-pyridyl)pentyl, 6-(3-pyridyl)hexyl, 2-methyl-3-(3-pyridyl)propyl, (4-pyridyl)methyl, 2-(4-pyridyl)ethyl, 1-(4-pyridyl)ethyl, 3-(4-pyridyl)propyl, 4-(4-pyridyl)butyl, 1,1-dimethyl-2-(4-pyridyl)ethyl, 5-(4-pyridyl)pentyl, 6-(4-pyridyl)hexyl, 2-methyl-3-(4-pyridyl)propyl, (3-pyrazyl)methyl, 2-(4-pyridazyl)ethyl, 1-(2-pyrimidyl)ethyl, 3-(2-pyrazyl)propyl, 4-(3-pyridazyl)butyl, 5-(4-pyrimidyl)pentyl, 6-(3-pyrazyl)hexyl, 2-methyl-3-(2-pyrimidyl)propyl, (2-tetrahydropyranyl)methyl, 2-(2-tetrahydropyranyl)ethyl, 1-(2-tetrahydropyranyl)ethyl, 3-(2-tetrahydropyranyl)propyl, 4-(2-tetrahydropyranyl)butyl, 1,1-dimethyl-2-(2-tetrahydropyranyl)ethyl, 5-(2-tetrahydropyranyl)pentyl, 6-(2-tetrahydropyranyl)hexyl, 2-methyl-3-(2-tetrahydropyranyl)propyl, (3-tetrahydropyranyl)methyl, 2-(3-tetrahydropyranyl)ethyl, 1-(3-tetrahydropyranyl)ethyl, 3-(3-tetrahydropyranyl)propyl, 4-(3-tetrahydropyranyl)butyl, 1,1-dimethyl-2-(3-tetrahydropyranyl)ethyl, 5-(3-tetrahydropyranyl)pentyl, 6-(3-tetrahydropyranyl)hexyl, 2-methyl-3-(3-tetrahydropyranyl)propyl, (4-tetrahydropyranyl)methyl, 2-(4-tetrahydropyranyl)ethyl, 1-(4-tetrahydropyranyl)ethyl, 3-(4-tetrahydropyranyl)propyl, 4-(4-tetrahydropyranyl)butyl, 1,1-dimethyl-2-(4-tetrahydropyranyl)ethyl, 5-(4-tetrahydropyranyl)pentyl, 6-(4-tetrahydropyranyl)hexyl, 2-methyl-3-(4-tetrahydropyranyl)propyl, (pyrrol-1-yl)methyl, 2-(pyrrol-2-yl)ethyl, 1-(pyrrol-3-yl)ethyl, 3-(pyrrol-1-yl)propyl, 1,1-dimethyl-2-(pyrrol-1-yl)ethyl, 6-(pyrrol-1-yl)hexyl, (2-thienyl)mehyl, 2-(3-thienyl)ethyl, 1-(2-thienyl)ethyl, 4-(2-thienyl)butyl, 5-(3-thienyl)pentyl, 2-methyl-3-(2-thienyl)propyl, [2-(2-hydroxyethyl)-1-pyrrolidinyl]methyl, 3-[3-(1-hydroxyethyl)morpholino]propyl, 4-[4-(3-hydroxypropyl)-1-piperidinyl]butyl, 5-[3-(4-hydroxybutyl)-2-thiomorpholino]pentyl, 6-[2-(5-hydroxypentyl)-1-imidazolyl]hexyl, 1,1-dimethyl-2-[2-(6-hydroxyhexyl)-1,2,4-triazol-1-yl]ethyl, 2-methyl-3-(3-hydroxymethyl-2-furyl)propyl, 1-(4-hydroxymethyl-1-piperazinyl)ethyl, (4-hydroxymethyl-2-pyridyl)methyl, (3-hydroxy-1-pyrrolidinyl)methyl, 3-(3-hydroxymorpholino)propyl, 4-(4-hydroxy-1-piperidinyl)butyl, 5-(3-hydroxy-2-thiomorpholino)pentyl, 6-(4-hydroxy-1-imidazolyl)hexyl, 1,1-dimethyl-2-(3-hydroxy-2-thienyl)ethyl, 2-methyl-3-(4-hydroxy-2-pyrimidyl)propyl, 4-(5-hydroxy-3-pyridazyl)butyl, (2-hydroxy-3-pyrazyl)methyl, 3-[3-(2-propionyloxyethyl)-1-pyrrolidinyl]propyl, 4-[3-(3-butyryloxypropyl)mropholino]butyl, 5-[4-(4-pentanoyloxtybutyl)-1-piperidinyl]pentyl, 6-[3-(5-hexanoyloxypentyl)-1-piperazinyl]hexyl, (4-acetyloxymethyl-2-pyridyl)methyl, 2-(3-propionyloxymethyl-2-furyl)ethyl, 1-(2-acetyloxymethylpyrrol-1-yl)ethyl, 3-(4-acetyloxymethyl-1-imidazolyl)propyl, (2,4,6-trimethyl-1-piperidinyl)methyl, 2-(3-ethyl-1-pyrrolidinyl)ethyl, 1-(3-propyl-1-piperazinyl)ethyl, 3-(3-methylmorpholino)propyl, 4-(5-butyl-2-thiomorpholino)butyl, 5-(5-methyl-2-imidazolyl)pentyl, 6-(3-pentyl-1,2,4-triazol-1-yl)hexyl, (3-methyl-2-tetrahydropyranyl)methyl, 2-(4-hexyl-3-pyridyl)ethyl, 2-(2-aminomethyl-1-pyrrolidinyl)ethyl, [3-(2-aminoethyl)-4-pyridazyl]methyl, 1-[4-(3-diethylaminoproipyl)-2-pyrimidyl]ethyl, 3-{3-[4-(N-methyl-N-propylaminobutyl]-2-pyrazyl}propyl, 4-[3-(5-dibutylaminopentyl)-2-furyl]butyl, 5-{3-[6-(N-ethyl-N-pentylamino(hexyl]-2-thienyl}pentyl, 6-(3-dihexylaminomethyl-1-piperazinyl)hexyl, (4-methylamino-1-imidazolyl)methyl, 2-(3-ethylamino-1,2,4-triazol-1-yl)ethyl, (4-ethoxy-1-piperidinyl)methyl, 3-(4-propoxy-2-pyridyl)propyl, 4-(3-butoxy-4-pyridazyl)butyl, 5-(4-pentyloxy-2-pyrimidyl)pentyl, 6-(2-hexyloxy-3-pyrazyl)hexyl, (3-methoxy-2-thienyl)methyl, 2-(2-methoxypyrrol-1-yl)ethyl, 1-(3-methoxy-2-furyl)ethyl, 3-(2-methoxy-1-imidazolyl)propyl, 4-(3-methoxy-1,2,4-triazol-1-yl)butyl, [4-(2-ethoxyethoxy(1-piperidinyl]methyl, 3-(3-propoxypropoxy-1-pyrrolidinyl)propyl, 4-(4-butoxybutoxy-2-pyridyl)butyl, 5-[3-(5pentyloxypentyloxy)-2-furyl]pentyl, 6-[2-(6-hexyloxyhexyloxy)-1-imidazolyl]hexyl, (3-methoxymethoxy-1,2,4-triazol-1-yl)methyl, (3-methoxymethoxy-2-tetrahydropyranyl)methyl, [2-(2-ethoxyethyl)-1-pyrrolidinyl]methyl, 3-[4-(3-propoxypropyl)-1-piperidinyl]propyl, 4-[4-(4-butoxybutyl)-1-piperazinyl]butyl, 5-[4-(5-pentyloxypentyl)-2-thiomorpholino]pentyl, 6-[1-(6-hexyloxyhexyl)-3-morpholino]hexyl, (2-methoxymethyl-1-imidazolyl)methyl, (3-ethxoymethyl-1,2,4-tetrazolyl)methyl, (4-methoxymethyl-2-tetrahydropyranyl)methyl, 2-(4-propoxymethyl-3-pyridyl)ethyl, 3-(3-butoxymethyl-2-furyl)propyl (3-dimethylamido-1-pyrrolidinyl)methyl, 3-(3-methylamido-1-piperidinyl)propyl, 4-(2-ethylamidomorpholino)butyl, 5-(3-propylamido-1-piperazinyl)pentyl, 6-(3-butylamido-2-thiomorpholino)hexyl, (3-pentylamido-2-pyridyl)methyl, 2-(4-hexylamido-1-imidazolyl)ethyl, 1-(3-dibutylamido-1,2,4-tetrazol-1-yl)ethyl, [3-(N-methyl-N-ethylamido-2-furyl]methyl, (4-hydroxy-2,6-dimethyl-1-piperidnyl)methyl, 1,3-oxathiolran-4- ylmethyl, 1,3-oxathiolane-2-thion-4-ylmethyl, 2-(1,3-oxathiolane-2-thion-4-yl)ethyl, 3-(1,3-oxathiolane-2-thion-4-yl)propyl and the like.

As to the lower alkyl group which may have, as substituent(s), 1–2 groups selected from the group consisting of an amino group (this amino group may be substituted by a lower alkanoyl group, a phenyl-lower alkyl group which may have a lower alkoxy group as a substituent on the phenyl ring, a lower alkenyl group, a hydroxy-lower alkyl group or a lower alkyl group), a hydroxyl group, lower alkylthio groups, lower alkanoyloxy groups, a tetrahydropyranyloxy group, halogen atoms, lower alkanoyl groups, a mercapto group, lower alkoxycarbonyl groups, a carboxy group, lower alkoxy groups, an amido group and lower alkylamido groups, there can be mentioned, in addition to the above-mentioned lower alkyl groups, hydroxy-lower alkyl groups, lower alkanoyloxy-lower alkyl groups and lower alkoxy-lower alkyl groups, straight chain or branched chain alkyl groups of 1–6 carbon atoms which may have, as substituent(s), 1–2 groups selected from the group consisting of an amino group [this amino group may be substituted by a straight chain or branched chain alkanoyl group of 1–6 carbon atoms, a phenylalkyl group which may have 1–3 straight chain or branched chain alkoxy groups of 1–6 carbon atoms as substituent(s(on the phenyl ring and whose alkyl portion is a straight chain or branched chain alkyl group of 1–6 carbon atoms, a straight chain or branched chain alkenyl group of 2–6 carbon atoms, a hydroxyalkyl group whose alkyl portion is a straight chain or branched chain alkyl group of 1–6 carbon atoms, or a straight chain or branched chain alkyl group of 1–6 carbon atoms], a hydroxyl group, straight chain or branched chain alkylthio groups of 1–6 carbon atoms, straight chain or branched chain alkanoyloxy groups of 2–6 carbon atoms, a tetrahydropyranyloxy group, halogen atoms, straight chain or branched chain alkanoyl groups of 1–6 carbon atoms, a mercapto group, alkoxycarbonyl groups whose alkoxy portions are each a straight chain or branched chain alkoxy group of 1–6 carbon atoms, a carboxy group, straight chain or branched chain alkoxy groups of 1–6 carbon atoms, an amido group and amido groups having 1–2 straight chain or branched chain alkyl groups of 1–6 carbon atoms; for example, aminomethyl, 2-formylaminoethyl, 1-acetylaminoethyl, 3-propionylaminopropyl, 4-butyrylaminobutyl, 1,1-dimethyl-2-pentanoylaminoethyl, 5-hexanoylaminopentyl, 6-[2-(3,4-dimethoxyphenyl)ethyl]aminohexyl, 2-methyl-3-benzylaminopropyl, (N-ethyl-N-benzylamino)methyl, 2-{N-ethyl-N-[2-(3,4-dimethoxyphenyl)ethyl]amino}ethyl, 3-(1-phenylethyl)aminopropyl, 4-[3-(2-ethoxyphenyl)propyl]aminobutyl, 1,1-dimethyl-2-(4-phenylbutyl)aminoethyl, 5-[5-(4-isopropoxyphenyl)pentyl]aminopentyl, 6-[6-(4-hexyloxyphenyl)hexyl]aminohexyl, (3,4,5-trimethoxybenzyl)aminomethyl, 2-(N-methyl-N-benzylamino)ethyl, 1-{N-propyl-N-3-[2-(3,4-dimethoxyphenyl)ethyl]amino}propyl, 4-(N-methyl-N-hexylamino)butyl, 1,1-dimethyl-2-[N-butyl-N-(2-phenylethyl)amino]ethyl, 5-[N-pentyl-N-(3-phenylpropyl)amino]pentyl, 6-[N-hexyl-N-(5-phenylpentyl)amino]hexyl, 2-methyl-3-allylaminopropyl, (N-ethyl-N-allylamino)methyl, 2-[N-(2-butenyl)amino]ethyl, 1-[N-methyl-N-(3-butenyl)amino]ethyl, 3-[N-(1-methylallyl)amino]propyl, 4-[N-(2-pentenyl)-N-propylamino]butyl, 1,1-dimethyl-2-[N-butyl-N-(2-hexenylamino]ethyl, 5-(hydroxymethylamino)pentyl, 6-[N-(2-hydroxyethyl)-N-ethylamino]hexyl, 2-methyl-3-[(1-hydroxyethyl)amino]propyl, [N-methyl-N-(3-hydroxypropyl)amino]methyl, 2-[N-propyl-N-(4-hydroxybutyl)amino]ethyl, 1-[(1,1-dimethyl-2-hydroxyethyl)amino]ethyl, 3-[N-butyl-N-(5-hydroxypentyl)amino]propyl, 4-[(6-hydroxyhexyl)amino]butyl, 1,1-dimethyl-2-[N-pentyl-N-(2-methyl-3-hydroxypropyl)amino]ethyl, 5-[N-hexyl-N-(2-hydroxyethyl)amino]pentyl, 6-methylaminohexyl, ethylaminomethyl, 2-propylaminoethyl, 1-isopropylaminoethyl, 3-butylaminopropyl, 4-pentylaminobutyl, 1,1-dimethyl-2-hexylaminoethyl, 5-dimethylaminopentyl, 6-diethlaminohexyl, 2-methyl-3-dipropylaminopropyl, dibutylaminomethyl, 2-dipentylaminoethyl, 1-dihexylaminoethyl, 3-(N-methyl-N-ethylamino)propyl, 4-(N-ethyl-N-propylamino)butyl, 5-(N-methyl-N-butylamino)pentyl, methylthiomethyl, 2-ethylthioethyl, 1-propylthioethyl, 3-butylthiopropyl, 4-pentylthiobutyl, 5-hexylthiopentyl, 6-isopropylthiohexyl, (2-tetrahydropyranyloxy)methyl, (3-tetrahydropyranyloxy)methyl, (4-tetrahydropyranyloxy)methyl, 2-(2-tetrahydropyranyloxy)ethyl, 2-(3-tetrahydropyranyloxy)ethyl, 2-(4-tetrahydropyranyloxy)ethyl, 1-(2-tetrahydropyranyloxy)ethyl, 1-(3-tetrahydropyranyloxy)ethyl, 1-(4-tetrahydropyranyloxy)ethyl, 3-(2-tetrahydropyranyloxy)propyl, 3-(3-tetrahydropyranyloxy)propyl, 3-(4-tetrahydropyranyloxy)propyl, 4-(2-tetrahydropyranyloxy)butyl, 4-(3-tetrahydropyranyloxy)butyl, 4-(4-tetrahydropyranyloxy)butyl, 5-(2-tetrahydropyranyloxy)pentyl, 5-(3-tetrahydropyranyloxy)pentyl, 5-(4-tetrahydropyranyloxy)pentyl, 6-(2-tetrahydropyranyloxy)hexyl, 6-(3-tetrahydropyranyloxy)hexyl, 6-(4-tetrahydropyranyloxy)hexyl, fluoromethyl, 2-chloroethyl, 1-bromoethyl, 3-iodopropyl, 3,3-dichloropropyl, 3,4-dibromobutyl, 5-chloropentyl, 3-bromohexyl, formylmethyl, acetylmethyl, 2-proipionylethyl, 3-butyrylpropyl, 4-isobutyrylbutyl, 1,1-dimethyl-2-pentanoylethyl, 5-tert-butylcarbonylpentyl, 6-hexanoylhexyl, mercaptomethyl, 2-mercaptoethyl, 1-mecaptoethyl, 3-mercaptopropyl, 4-mercaptobutyl, 5-mercaptopentyl, 6-mercaptohexyl, methoxycarbonylmethyl, 2-ethoxycarbonylethyl, 1-propoxycarbonylethyl, 3-tert-butoxycarbonylpropyl, 4-pentyloxycarbonylbutyl, 5-hexyloxycarbonylpentyl, carboxymethyl, 2-carboxyethyl, 1-carboxyethyl, 3-carboxypropyl, 4-carboxybutyl, 5-carboxypentyl, 6-carboxyhexyl, amidomethyl, methylamidomethyl, 2-ethylamidoethyl, 1-propylamidoethyl, 3-butylamidopropyl, 4-(N-ethyl-N-hexylamido)butyl, 1,1-dimethyl-2-(N-methyl-N-ethylamido)ethyl, 5-(N-methyl-N-propylamido)pentyl, 6-(N-methyl-N-butylamido)hexyl, 2-methyl-3-pentylamidopropyl, hexylamidomethyl, 2-diethylaminoethyl, 1-hydroxy-3-diethylamino-2-propyl, 3-diethylaminopropyl, 4-diethylaminobutyl, diethylamidomethyl, 2-diethylaminoisopropyl, 1-diethylamidoethyl, 2-hydroxy-1-diethlamido-1-ethyl, 4-methylthio-1-diethylamino-2-butyl, 3-methylthio-1-diethylamido-1-propyl, 2-acetylaminoethyl, 2-[N-(2-hydroxyethyl)-N-ethylamino]ethyl, 2-(N-allyl-N-ethylamino]ethyl, 3-diethtylamino-2-hydroxypropyl, 3-ethylamino-2-hydroxypropyl, 3-amino-2-hydroxypropyl, 2-(N-ethyl-N-benzylamino)ethyl, 2-diethylamino-3-hydroxypropyl, 2,3-diacetyloxypropyl, 3-methoxy-2-hydroxypropyl, 2,3-dimethoxypropyl, 2-hydroxy-1-methoxycarbonyl-1-ethyl, 3-chloro-2-hydroxypropyl, 2-hydroxypropyl, ethoxycarbonylmethyl, 3-mercapto-2-hydroxypropyl, 3-ethylthio-2-hydroxypropyl, 1-hydroxy-4-methylthio-2-butyl, 1-acetyloxy-4-methylthio-2-butyl, 1-methoxycarbonyl-3-methylthio-1-propyl and the like.

The carbostyril derivative represented by the general formula (1) according to the present invention can be produced by various processes. It can be easily produced by, for example, processes shown by the following reaction formuals.

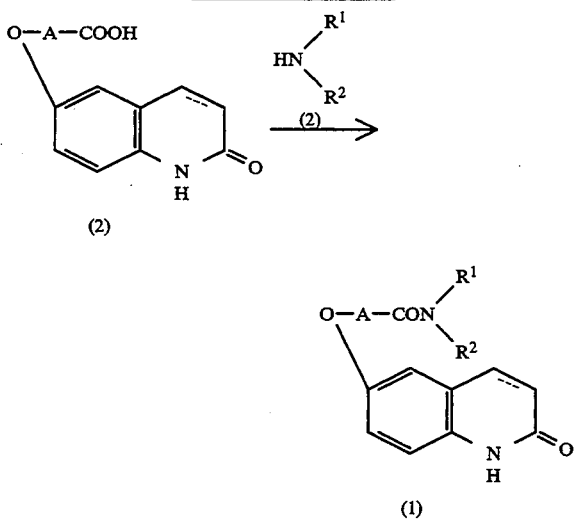

(in the above formula, $R^1$, $R^2$ and the carbon-carbon bond between 3- and 4-positions in the carbostyril skeleton have the same definitions as above.)

The process shown by the reaction formula 1 is a process wherein a carboxyalkoxycarbostyril derivative represented by the general formula (2) and an amine represented by the general formula (3) are reacted according to an ordinary reaction for amido bond formation. In the present invention, the compound of the general formula (2) may be used in a form in which the carboxyl group has been activated.

In the reaction for amido bond formation, known reaction conditions can be used easily.

For example, there can be mentioned:

(a) a mixed acid anhydride method, i.e. a method comprising reacting a carboxylic acid (2) with an alkyl halocarboxylate to obtain a mixed acid anhydride and then reacting the anhydride with an amine (3), (b) an active ester method, i.e. a method comprising converting a carboxylic acid (2) to a p-nitrophenyl ester, an N-hydroxysuccinimide ester, a 1-hydroxybenzotriazole ester or the like and then reacting the ester with an amine (3), (c) a carbodiimide method, i.e. a method comprising subjecting a carboxylic acid (2) and an amine (3) to dehydration and condensation in the presence of a dehydrogenating agent such as dicyclohexylcarbodiimide, carbonyldiimidazole or the like, and (d) other methods, i.e. a method comprising converting a carboxylic acid (2) to a carboxylic acid anhydride with a dehydrating agent such as acetic anhydride or the like and reacting the carboxylic anhydride with an amine (3), a method comprising reacting an ester of a carboxylic acid (2) with a lower alcohol, with an amine (3), and a method comprising reacting a halogenation product of a carboxylic acid (2), namely a carboxylic acid halide with an amine (3).

Of the above methods, the mixed acid anhydride method is preferred.

As to the alkyl halocarboxylate used in the mixed acid anhydride method, there can be mentioned methyl chloroformate, methyl bromoformate, ethyl chloroformate, ethyl bromoformate, isobutyl chloroformate, etc. The mixed acid anhydride can be obtained by an ordinary Schotten-Baumann reaction and, it is reacted with an amine (3) usually without being isolated, to obtain a compound of the general formula (1) of the present invention. The Schotten-Baumann reaction is effected in the presence of a basic compound. As to the basic compound, there can be used those compounds conventionally employed in the Schotten-Baumann reaction, and there can be mentioned organic bases such as triethylamine, trimethylamine, pyridine, dimethylaniline, N-methylmorpholine, 1,5-diazabicyclo[4,3,0]nonene-5 (DBN), 1,8-diazabicyclo[5,4,0]undecene-7 (DBU), 1,4-diazabicyclo[2,2,2]-octane (DABCO) and the like, as well as inorganic bases such as potassium carbonate, sodium carbonate, potassium hydrogencarbonate, sodium hydrogencarbonate, potassium hydroxide, sodium hydroxide and the like. The reaction is effected usually at about $-20°$ to $100°$ C., preferably at about $0°$ to $50°$ C., and the reaction time is about 5 minutes to 10 hours. The reaction of the resulting mixed acid anhydride with an amine (3) is effected usually at about $-20°$ to $150°$ C., preferably at about $10°$ to $50°$ C., and the reaction time is about 5 minutes to 10 hours. The mixed acid anhydride method is effected generally in a solvent. As to the solvent, there can be used any solvent conventionally used in the mixed acid anhydride method, and there can be specifically mentioned, for example, halogenated hydrocarbons such as dichloromethane, dichloroethane, chloroform and the like, aromatic hydrocarbons such as benzene, toluene, xylene and the like, ethers such as tetrahydrofuran, diethyl ether, dimethoxyethane and the like, esters such as ethyl acetate, methyl acetate and the like, and aprotic solvents such as N,N-dimethylformamide, dimethyl sulfoxide, hexamethylphosphoric triamide and the like. In said method, the carboxylic acid (2), the alkyl halocarboxylate and the amine (3) are used usually in an equimolar ratio, but it is preferable that the alkyl halocarboxylate and the amine (3) be used each in an amount of about 1-1.5 moles per 1 mole of the carboxylic acid (2).

In the reaction formula 1, the carboxylic acid (2) is a known compound or a novel compound. The amine (3) can be produced by, for example, the processes shown by the reaction formulas 8-19.

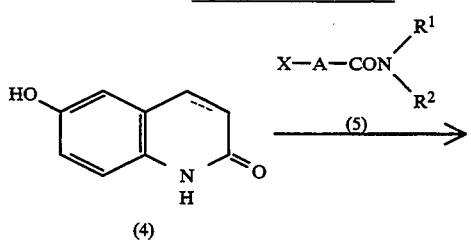

-continued

[Reaction formula-2]

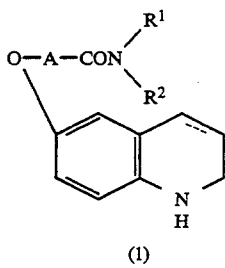

(1)

[in the formula, A, $R^1$, $R^2$ and the carbon-carbon bond between 3- and 4-positions in the carbostyril skeleton have the same definitions as above, and X represents a halogen atom.]

According to the reaction formula-2, a hydroxycarbonstyril derivative represented by the gneral formula (4) is reacted with a haloalkaneamide derivative represented by the general formula (5) under the conditions of dehydrohalogenation reaction to obtain a compound (1) of the present invention.

This dehydrogenation reaction is effected using a basic compound as a dehydrohalogenating agent. As to the basic compound, there can be widely used those known conventionally, and there can be mentioned inorganic bases such as sodium hydroxide, potassium hydroxide, sodium carbonate, potassium carbonate, sodium hydrogencarbonate, potassium hydrogencarbonate, sodium hydride, silver carbonate and the like, alcoholates such as sodium methylate, sodium ethylate and the like, and organic bases such as diisopropylethylamine, triethylamine, pyridine, N,N-dimethylaniline, DBN, DBU, DABCO and the like. Said reaction is effected in the presence or absence of a solvent. As to the solvent, there can be used any inactive solvent which gives no adverse effect on the reaction, and there can be mentioned, for example, alcohols such as methanol, ethanol, isoproipanol, butanol, ethylene glycol and the like, ethers such as dioxane, tetrahydrofuran, diethyl ether, monoglyme, diglyme and the like, halogenated hdyrocarbons such as dichloromethane, chloroform, carbon tetrachloride and the like, ketones such as acetone, methyl ketone and the like, aromatic hydrocarbons such as benzene, toluene, xylene and the like, esters such as ethyl acetate, methyl acetate and the like, and aprotic polar solvents such as acetonitrile, N,N-dimethylformamide, dimethyl sulfoxide, hexamethylphosphoric triamide and the like. Said reaction is advantageously effected in the presence of a metal iodide such as sodium iodide, potassium iodide or the like. In the above method, the amount of the compound of the general formula (5) used relative to the compound of the general formula (4) is not specified and can be appropriately selected in a wide range. However, when the reaction is effected using no solvent, the former is preferably used in a large excess amount relative to the latter; when the reaction is effected in a solvent, the former can be used in an amount of usually about 1-5 moles, preferably about 1-2 moles per 1 mole of the latter. The reaction temperature is not specified, either, but is usually about room temperature to 200° C., preferably about room temeprature to 160° C. The reaction time is usually about 1-30 hours.

Those compounds of the general formula (1) according to the present invention wherein the carbon-carbon bond between 3- and 4-positions in the carbostyril skeleton is a double bond can each take lactam-lactim tautomers [(1a) and (1b)] as shown by the following reaction formula-3.

[Reaction formula-3]

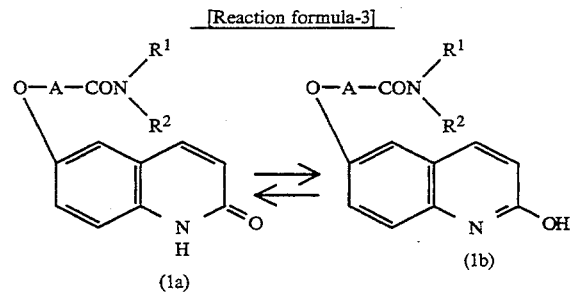

(in the formula, a, $R^1$ and $R^2$ have the same definition as above.)

The compound of the general formula (1c) according to the present invention wherein the carbon-carbon bond between 3- and 4-positions in the carbostyril skeleton is a single bond and the above-mentioned compound of the general formula (1a(according to the present invention are interchangeable by a reduction reaction or a dehydrogenation reaction, as shown by the following reaction formula-4.

[Reaction formula-4]

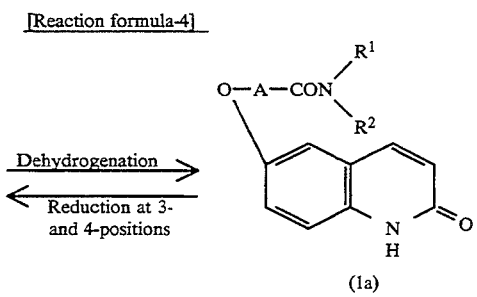

(in the formula, A, $R^1$ and $R^2$ have the same definitions as above.)

In the reduction of the compound of the general formula (1a), there can be applied conditions used in ordinary catalytic reduction reactions. As to the catalyst used, there can be mentioned, for example, metals such as palladium, palladium-carbon, platinum, Raney nickel and the like. These metals can be used in a usual catalyst amount. As to the solvent used, there can be mentioned, for example, methanol, ethanol, isopropanol, dioxane, tetrahydrofruan, hexane, cyclohexane and ethyl acetate. The reduction reaction can be effected under normal pressure or applied pressure, but can be effected usually at about normal pressure ot 20 kg/cm², preferaly at about normal pressure ot 10 kg/cm². The reaction temperature can be usually at about 0° to 150° C., preferably at about room temperature to 100° C.

The dehydrogenation reaction of the compound of the general formula (1c) is effected in an appropriate solvent, using an oxidizing agent. As to the oxidizing agent, there can be mentioned, for example, benzoquinones such as 2,3-dichloro-5,6-dicyanobenzoquinone, chloranil (2,3,5,6-tetrachlorobenzoquinone(and the like, halogenation agents such as N-bromosuccinimide, N-chlorosuccinimide, bromine and the like, and hydrogenation catalysts such as selenium dioxide, palladium carbon palladium black, palladium oxide, Raney nickel and the like. The amount of the halogenation agent used is not specified and can be appropriately selected in a wide range. The amount can be usually about 1–5 moles, preferably about 1–2 moles per 1 mole of the compound of the general formula (1c). When a hydrogenation catalyst is used as the oxidizing agent, it can be used in a usual catalyst amount. As the solvent, there can be mentioned, for example, ethers such as dioxane, tetrahydrofuran, methoxyethanol, dimethoxymethane and the like, aromatic hydrocarbons such as benzene, toluene, xylene cumene and the like, halogenated hydrocarbons such as dichloromethane, dichloroethane, chloroform, carbon tetrachloride and the like, alcohols such as butanol, amyl alcohol, hexanol and the like, polar protic solvents such as acetic acid and the like, and polar aprotic solvents such as dimethylformamide, dimethyl sulfoxide, hexamethylphosphoric triamide and the like. Said reaction is effected usually at about room temeprature to 300° C., preferably at about room temperature to 200° C., and is completed generally in about 1–40 hours.

hydrochloric acid and nitric acid; as the organic acid, there can be mentioned, for example, acetic acid, aroamtic sulfonic acids (e.g. p-toluenesulfonic acid) and Lewis acids (e.g. boron trichloride). As to the solvent, there can be mentioned, for example, water; alcohols such as methanol, ethanol, isopropanol and the like; ketones such as acetone, methyl ethyl ketone and the like; ethers such as dioxane, tetrahydrofuran, ethylene glycol dimethyl ether and the like; acetic acid; and their mixtures. Said reaction proceeds usually at about room temperature to 200° C., preferably at about room temeprature to 150° C., and is completed generally in about 0.5–18 hours.

The reaction for converting the compound of the general formula (1e) into a compound of the general formula (1f) is effected in the presence of a lower alkanoylating agent. As the lower alkanoylating agent, there can be used, for example, lower alkanolic acids such as formic acid, acetic acid, propionic acid and the like; lower alkanoic acid anhydrides such as acetic anhydride and the like; and lower alkanoic acid halides such as acetyl chloride, propionyl bromide and the like.

When an acid anhydride or an acid halide is used as the lower alkanoylating agent, a basic compound may be allowed to be present in the reaction system. As to such a basic compound, there can be mentioned, for example, alkali metals such as metallic sodium, metallic potassium and the like; hydroxyides, carbonates and bicarbonates of said alkali metals; and organic bases such as triethylamine, pyridine, piperidine and the like. The above reaction proceeds in the absence or presence of a solvent, but is effected usually in an appropriate solvent. As to the solvent, there can be mentioned, for

[Reaction formula-5]

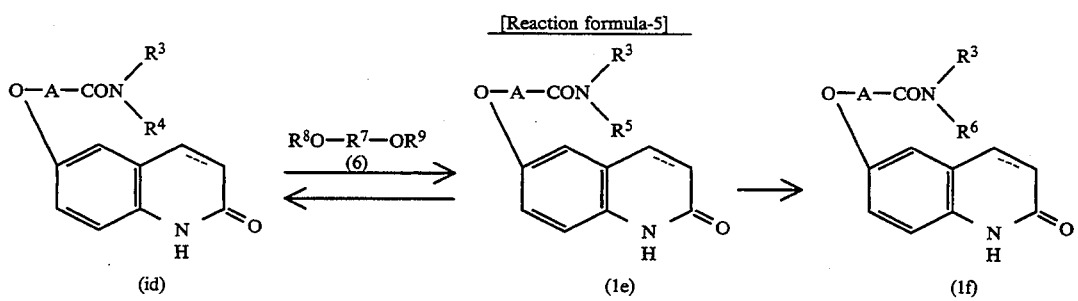

(in the formula, A and the carbon-carbon bond between 3- and 4-positions in the carbostyril skeleton have the same definitions as above; $R^3$ represents the above-mentioned $R^1$ but excludes a lower alkylenedioxy group-substituted lower alkyl group; $R^4$ represents a lower alkylenedioxy group-substituted lower alkyl group; $R^5$ represents a lower alkyl group having 2 hydroxyl groups; $R^6$ represents a lower alkyl group having 1–2 lower alkanoyloxy groups; $R^7$ represents a lower alkylene group; and $R^8$ and $R^9$ each represent a lower alkyl group.)

The compound of the general formula (1d) can be converted into a compound of the general formula (1e) by hydrolysis. In the hydrolysis reaction, any conditions employed in ordinary hydrolysis reactions can be applied. The hydrolysis reaction is effected usually in an appropriate solvent in the presence of a basic compound, a mineral acid, an organic acid or the like. As to the basic compound, there can be mentioned, for exmaple, sodium hydroxide, potassium hydroxide, barium hydroxide, and potassium carbonate; as the mineral acid, there can be mentioned, for example, sulfuric acid, example, ketones such as acetone, methyl ethyl ketone and the like; ethers such as dioxane, diethyl ether and the like; aromatic hydrocarbons such as benzene, toluene, xylene and the like; halogenated hydrocarbons such as dichloromethane, chloroform, carbon tetrachloride and the like; acetic acid; acetic anhydride; water; and pyridine. The amount of the lower alkanoylating agent used can be at least about equimolar, generally equimolar to a large excess relative to the compound of the general formula (1e). The reaction temperature is usually about 0°–150° C., preferably about 0°–100° C., and the reaction is completed generally in about 5 minutes to 15 hours.

When a lower alkanoic acid is used as the lower alkanoylating agent, it is preferable that there be added to the reaction system an acid-removing agent such as a mineral acid (e.g. sulfuric acid, hydrochloric acid) or a sulfonic acid (e.g. p-toluenesulfonic acid, benzenesulfonic acid, ethanesulfonic acid). In this case, the reaction temeprature is particularly preferably about 50°–120° C.

The reaction of the compound of the general formula (1e) with the compound of the general formula (6) is effected in an appropriate solvent in the presence of an acid. As to the solvent used therein, there can be mentioned, for example, halogenated hydrocarbons such as dichloromethane, chloroform, carbon tetrachloride and the like; aormatic hydrocarbons such as benzene, toluene, xylene and the like; ketones such as acetone, methyl ethyl ketone and the like; ethers such as dioxane, tetrahydrofuran, diethyl ether and the like; and aprotic polar solvents such as dimethylformamide, dimethyl sulfoxide and the like. As to the acid, there can be mentioned, for example, inorganic acids such as hydrochloric acid, sulfuric acid, nitric acid, phosphoric acid, perchloric acid and the like; and organic acids such as acetic acid, propionic acid, p-toluenesulfonic acid and the like. The amount of the compound of the general formula (6) used can be usually at least about 1 mole, preferably about 2-5 mols per 1 mole of the compound of the general formula (1e). Said reaction is effected usually at about room temperature to 200° C., preferably at about 50°-100° C., and is completed generally in about 30 minutes to 12 hours.

When the compound of the general formula (3) is a compound having, as $R^2$, a lower alkyl group having 2 hydroxyl groups, the compound can be converted into a compound of the general formula (3) having as $R^2$, a lower alkyl group substituted by a lower alkylenedioxy group, by treating in the same manner as in the above reaction of the compound of the general fromula (1e) with the compound of the general formula (6).

The compound of the general formula (3) having, as $R^2$, a lower alkyl group substituted by a lower alkylenedioxy group can be converted into a compound of the general formula (3) having, as $R^2$, a lower alkyl group, by treating in the same manner as in the reaction for converting the compound of the general formula (1d) to the compound of the general formula (1e).

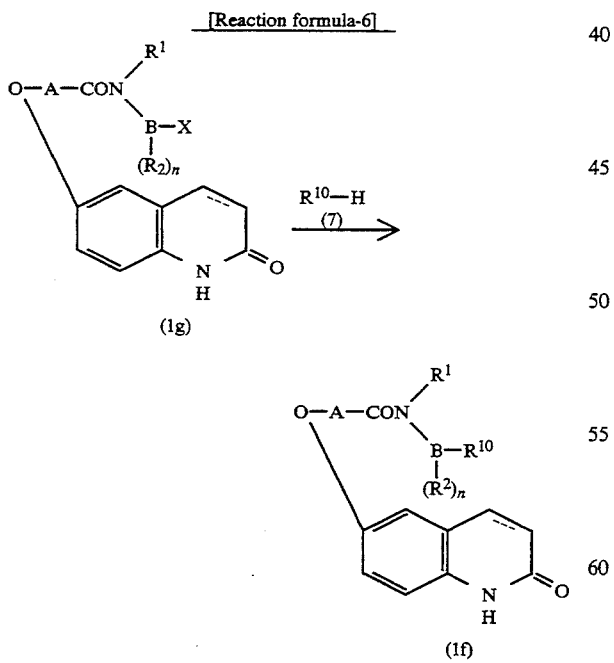

(in the formula A, $R^1$, $R^2$, X and the carbon-carbon bond between 3- and 4-positions in the carbostyril skeleton have the same definitions as above; B represents a lower alkyl group; n represents 0 or 1; $R^{10}$ represents a phenyl-lower alkyl group which may have a lower alkoxy group as a substituent on the phenyl ring, a lower alkenyl group, a hydroxy-lower alkyl group, an amino group, a lower alkylamino group, a

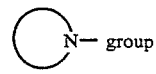

or a lower alkanoyloxy group, wherein the

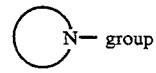

is an at least one nitrogen atom-containing 5-membered or 6-membered saturated or unsaturated heterocyclic group which may have, as substituent(s) on the heterocycle, 1-3 groups selected from the group consisting of hydroxy-lower alkyl groups, lower alkanoyloxy-lower alkyl groups, a hydroxyl group, lower alkyl groups, amino-lower alkyl groups, lower alkylamino-lower alkyl groups, lower alkoxy groups, lower alkoxy-lower alkoxy groups, lower alkoxy-lower alkyl groups, a thio group and lower alkylamido groups, when $R^{10}$ is the

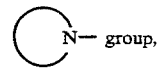

n is 0).

The reaction of a compound of the general formula (1g) with a compound of the general formula (7) is effected under the same conditions as in the reaction of the compound of the general formula (4) with the compound of the general formula (5).

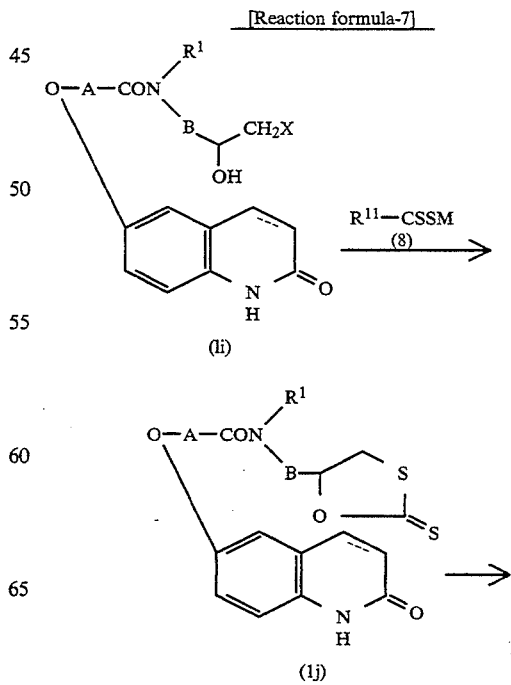

-continued

[Reaction formula-7]

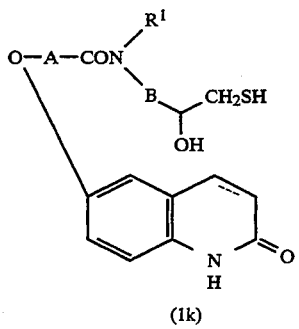

(1k)

(in the formula, A, $R^1$, B, X and the carbon-carbon bond between 3- and 4-positions in the carbostyril skeleton have the same definitions as above; $R^{11}$ represents a lower alkoxy group; and M represents an alkali metal atom.)

In the reaction formula (7), as the alkali metal atom represented by M, there can be mentioned, for example, a sodium atom and potassium atom.

The reaction of a compound of the general formula (1i) with a compound of the general formula (8) is effected in an appropriate solvent. As the solvent, there can be used any solvent employed in the reaction of the compound of the general formula (4) with the compound of the general formula (5). The amount of the compound of the general formula (8) used can be usually at least about 1 mole, preferably about 1–1.5 moles per 1 mole of the compound of the general formula (1i). Said reaction is effected usually at about 0°–150° C., preferably at about 0°–100° C., and is complete generally in about 1–10 hours.

The reaction for converting a compound of the general formula (1j) into a compound of the general formula (1k) is effected in a solventless state or in an appropriate solvent in the presence of an acid or a base. As to the solvent used therein, there can be mentioned, for example, water; alcohols such as methanol, ethanol and the like; ketones such as acetone, methyl ethyl ketone and the like; ethrs such as dioxane, tetrahydrofuran and the like; aprotic polar solvents such as dimethylformamide, dimethyl sulfoxide and the like; and their mixtures. As to the acid, there can be mentioned, for example, inorganic acids such as hydrochloric acid, sulfuric acid, phosphoric acid and the like; and organic acids such as acetic acid, propionic acid, p-toluene-sulfonic acid and the like. As to the base, there can be mentioned morpholine, ethylenediamine, etc. Said reaction proceeds usually at about room temperature to 200° C., preferably at about room temperature to 150° C., and is completed generally in about 0.5 to 18 hours.

When the compound of the general formula (1), the compound of the general formula (3) and the compound of the general formula (11) are compounds having, as $R^2$, a lower alkyl group having at least one hydroxyl group, respectively, they can be converted, by oxidation, into a compound of the general formula (1), a compound of the general formula (3) and a compound of the general formula (11) each having, as $R^2$, a lower alkyl group having at least one lower alkanoyl group.

Said oxidation reaction is effected in an appropriate solvent in the presence of an oxidizing agent. The solvent can be any conventionally known solvent as long as it gives no adverse effect on the reaction, and there can be mentioned, for example, water; organic acids such as formic acid, acetic acid, trifluoroacetic acid and the like; alcohols such as methanol, ethanol, iropropanol and the like; halogenated hydrocarbons such as dichloroemthane, dichloroethane, chloroform and the like; and ketones such as acetone, methyl ethyl ketone and the like. As to the oxidizing agent, there can be generally used any conventionally known oxidizing agent capable of converting a hydroxyl group to a carbonyl group, and there can be mentioned, for example, chromic acid, chromic acid salts such as sodium chromate; potassium chromate and the like; permanganic acid; permanganic acid salts such as sodium permanganate, potassium permanganate and the like; iodic acid salts such as sodium periodate and the like; and selenium compounds such as selenium dioxide and the like. The oxidizing agent can be used in an amount of usually about 1 mole, preferably about 1–1.5 moles per 1 mole of the material compound to be treated. Said reaction is effected usually at about −70° to 40° C., preferably at about −70° C. to room temperature, and is complete generally in about 5 minutes to 3 hours.

When the compound of the general formula (1), the compound of the general formula (3) and the compound of the general formula (9) are compounds having, as $R^1$, a cycloalkyl-lower alkyl group having a hydroxy-lower alkyl group, respectively, they can be converted, by lower alkanoylation, into a compound of the general formula (1), a compound of the general formula (3) and a compound of the general formula (9) each having, as $R^1$, a cycloalkyl-lower alkyl group having a lower alkanoyloxy-lower alkyl group. The lower alkanoylation can be effected under the same conditions as in the reaction for converting the compound of the general formula (1e) into the compound of the general formula (1f).

When the compound of the general formula (1), the compound of the general formula (3) and the compound of the general formula (11) are compounds having, as $R^2$, a 5-membered or 6-membered saturated or unsaturated heterocycle-lower alkyl group having at least one hydroxy-lower alkyl group, or compounds having, as $R^2$, a lower alkyl group having at least one hydroxyl group, respectively, they can be converted, by lower alkanoylation, to a compound of the general formula (1), a compound of the general formula (3) and a compound of the general formula (11) each having, as $R^2$, a 5-membered or 6-membered saturated or unsaturated heterocycle-lower alkyl group having at least one lower alkanoyloxy-lower alkyl group, or a compound of the general formula (1), a compound of the general formula (3) and a compound of the general formula (11) each having, as $R^2$, a lower alkyl group having at least one lower alkanoyloxy group. This lower alkanoylation can be effected under the same conditions as in the reaction for converting the compound of the general formula (1e) into the compound of the general formula (1f).

When the compound of the general formula (1), the compound of the general formula (3) and the compound of the general formula (11) are compounds having, as $R^2$, a lower alkyl group having at least one tetrahydropyranyloxy group or compounds having as $R^2$, a 5-membered or 6-membered saturated or unsaturated heterocycle-lower alkyl group having at least one lower alkoxy-lower alkyl group, respectively, they can be converted, by hydrolysis, into a compound of the general formula (1), a compound of the general formula (3)

and a compound of the general formula (11) each having, as $R^2$, a lower alkyl group having at least one hydroxyl group, or a compound of the general formula (1), a compound of the general formula (3) and a compound of the general formula (11) each having, as $R^2$, a 5-membered or 6-membered saturated or unsaturated heterocycle-lower alkyl group having at least one hydroxyl group. This hydrolysis can be effected under the same conditions as in the reaction for converting the compound of the general formula (1d) into the compound (1e).

When the compound of the general formula (1), the compound of the general formula (3), the compound of general formula (9) and the compound of the general formula (11) are compounds having, as $R^1$, a cycloalkyl-lower alkyl group having a lower alkoxycarbonyl group or a carboxy group, or compounds having, as $R^2$, a lower alkyl group having at least one lower alkoxycarbonyl group, respectively, they can be converted, by reduction, into a compound of the general formula (1), a compound of the general formula (3), a compound of the general formula (9) and a compound of the general formula (11) each having, as $R^1$, a cycloalkyl-lower alkyl group having a hydroxy-lower alkyl group, or a compound of the general formula (1), a compound of the general formula (3), a compound of the general formula (9) and a compound of the general formula (11) each having, as $R^2$, a lower alkyl group having at least one hydroxyl group.

Said reduction reaction is effected usually using a hydride reducing catalyst. As to the hydride reducing agent, there can be mentioned, for example, sodium boron hydride, lithium aluminium hydride and diborane. The amount of the hydride reducing agent used can be usually 1 mole to a large excess, preferably about 1-25 moles per 1 mole of the material compound to be treated. This reduction reaction is effected usually at about $-60°$ to $150°$ C., preferably at about $-30°$ to $100°$ C. for about 10 minutes to 5 hours, using an appropriate solvent, for example, water, a lower alcohol (e.g. methanol, ethanol, isopropanol)or an ether (e.g. tetrahydrofuran, diethyl ether, diglyme). When there is used, as the reducing agent, lithium aluminum hydride or diborane, there is preferably used an anhdyrous solvent such as tetrahydrofuran, diethyl ether, diglyme or the like.

The compound of the general formula (3) as a starting material includes novel compounds and can be easily produced according to the processes shown by the following reaction formulas.

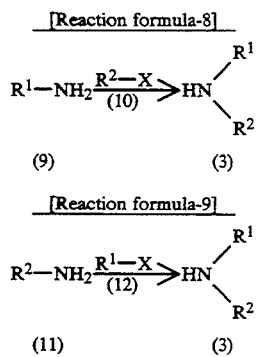

(in the above formulas, $R^1$, $R^2$ and X have the same definitions as above.)

The reaction of a compound of the general formula (9) with a compound of the general formula (10) and the reaction of a compound of the general formula (11) with a compound of the general formula (12) can both be effected under the same conditions as in the reaction of the compound of the general formula (4) with the compound of the general formula (5).

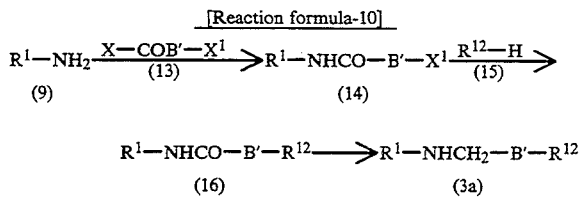

(in the formula, $R^1$ and X have the same definitions as above; $X^1$ represents a halogen atom; B' represents a lower alkylene group, with the proviso that the carbon atoms of a group —CO—B'— or a group —CH$_2$—B'— are not more than 6; $R^{12}$ represents a group —NR$^{13}$R$^{14}$ or a lower alkanoyloxy group, wherein $R^{13}$ and $R^{14}$ may be the same or different and each represent a hydrogen atom, a phenyl-lower alkyl group which may have a lower alkoxy group as a substituent on the phenyl ring, a lower alkenyl group, a hydroxy-lower alkyl group or a lower alkyl group, and $R^{13}$ and $R^{14}$ may further form, together with the nitrogen atom to which they bond, a 5-membered or 6-membered saturated or unsaturated heterocycle which may have, as substituents, 1–3 groups selected from the group consisting of hydroxy-lower alkyl groups, lower alkanoyloxy-lower alkyl groups, a hydroxyl group, lower alkyl groups, an amino group, lower alkylamino groups, lower alkoxy groups, lower alkoxy-lower alkoxy groups, lower alkoxy-lower alkyl groups, a thio group and lower alkylamido groups.)

The reaction of a compound of the general formula (9) with a compound of the general formula (13) can be effected in the same conditions as in the reaction of the compound of the general formula (4) with the compound of the general formula (5).

The reaction of a compound of the general formula (14) with a compound of the general formula (15) can be effected under the same conditions as in the reaction of the compound of the general formula (4) with the compound of the general formula (5).

The reactions for converting into a compound of the general formula (16) and a compound of the general formula (3a) are effected in an appropriate solvent in the presence of a hydride reducing agent. As the reducing agent used, there can be mentioned, for example, sodium boron hydride, lithium aluminum hydride and diborane. The amount of the reducing agent used can be at least about 1 mole, preferably about 1-3 moles per 1 mole of the starting material to be treated. When lithium aluminum hydride is used as the reducing agent, it can be used preferably in the same weight amount as the starting material. As the solvent used, there can be mentioned, for example, water; lower alcohols such as methanol, ethanol, isopropanol and the like; and ethers such as tetrahydrofuran, diethyl ether, diglyme and the like. Said reaction is effected usually at about $-60°$ to $150°$ C., preferably at about $-30°$ to $100°$ C., and is complete generally in about 10 minutes to 15 hours. When there is used, as the reducing agent, lithium aluminum hydride or diborane, there is preferably used an anhydrous solvent such as diethyl ether, tetrahydrofuran, diglyme or the like.

[Reaction formula-11]

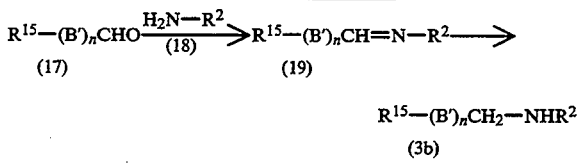

(in the formula, $R^2$, n and B' have the same definitions as above, with the proviso that the carbon atoms of the group —B'—$CH_2$— are not more than 6; $R^{15}$ represents a cycloalkyl group which may have, as a substituent, a group selected from the group consisting of lower alkoxycarbonyl groups, a carboxy group, lower alkanoyloxy-lower alkyl groups, amino-lower alkyl groups, lower alkylamino-lower alkyl groups and hydroxy-lower alkyl groups, a tetrahydropyranyl group, a lower alkylene-dioxy group, a phenyl group having, as substituent(s) on the phenyl ring, 1-3 groups selected from the group consisting of lower alkyl groups and a hydroxyl group, or a piperidinyl group having a lower alkyl group as a substituent; when n is 0, $R^{15}$ must not be a lower alkylenedioxy group.)

The reaction of a compound of the general formula (17) with a compound of the general formula (18) is effected in a solventless state or in an appropriate solvent in the absence or presence of a dehydrating agent. As to the solvent used, there can be mentioned, for example, alcohols such as methanol, ethanol, isopropanol and the like; aromatic hydrocarbons such as benzene, toluene, xylene and the like; and aprotic polar solvents such as dimethylformamide, dimethylacetamide, N-methylpyrrolidone and the like. As to the dehydrating agent, there can be mentioned, for example, desiccants usually used for dehydration of solvent, such as molecular sieve and the like; mineral acids such as hydrochloric acid, sulfuric acid, boron trifluoride and the like; and organic acids such as p-toluenesulfonic acid and the like. Said reaction is effected usually at about room temperature to 200° C., preferably at about room temperature to 150° C., and is complete generally in about 1-48 hours. The amount of the compound of the general formula (18) used is not specified but can be usually at least about 1 mole, preferably about 1-15 moles per 1 mole of the compound of the general formula (17). The amount of the dehydrating agent used can be usually a large excess when a desiccant is used, and a catalyst amount when an acid is used. The thus obtained compound of the general formula (19) is used for the subsequent reduction reaction without being isolated.

Various methods can be applied for the reduction reaction of the compound of the general formula (19). For example, there can be preferably used a reduction method using a hydride reducing agent. As to the hydride reducing agent used, there can be mentioned, for example, lithium aluminum hydride, sodium boron hydride and diborane. The amount of the reducing agent used can be at least about 1 mole, preferably about 1-10 moles per 1 mole of the compound of the general formula (19). This reduction reaction is effected usually at about −60° to 50° C., preferably at about −30° C. to room temeprature for about 10 minutes to 5 hours, usually using an appropriate solvent, for example, water, a lower alcohol (e.g. methanol, ethanol, isopropanol), or an ether (e.g. tetrahydrofuran, diethyl ether, diaglyme). When lithium aluminum hydride or diborane is used as the reducing agent, there is preferably used an anhydrous solvent such as diethyl ether, tetrahydrofuran, diglyme or the like.

The reduction of the compound of the general formula (19) can also be effected by subjecting the compound to catalytic hydrogenation in an appropriate solvent in the presence of a catalyst. As the solvent used, there can be mentioned, for example, water; acetic acid; alcohols such as methanol, ethanol, isopropanol and the like; hydrocarbons such as hexane, cyclohexane and the like; ethers such as dioxane, tetrahydrofuran, diethyl ether, ethylene glycol dimethyl ether and the like; esters such as ethyl acetate, methyl acetate and the like; and aprotic polar solvents such as dimethylformamide and the like. As the catalyst used, there can be mentioned, for example, palladium, palladium-black, palladium-carbon, platinum, platinum oxide, copper chromite and Raney nickel. The amount of the catalyst used can generally be about 0.02-1 time that of the compound of the general formula (19). The reaction temperature can be usually about −20° to 150° C., preferably about 0° to 100° C.; the hydrogen pressure can be usually about 1-10 atm.; said reaction is complete in about 0.5-10 hours.

[Reaction formula-12]

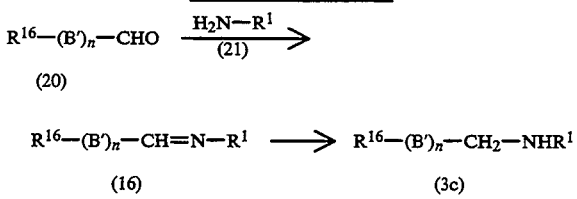

(in the formula, $R^1$, n and B' have the same definitions as above; and $R^{16}$ represents a 5-membered or 6-membered saturated or unsaturated heterocyclic group which may have, an substituent(s) on the heterocycle, 1-3 groups selected from the group consisting of hydroxy-lower alkyl groups, lower alkanoyloxy-lower alkyl groups, a hydroxyl group, lower alkyl groups, amino-lower alkyl groups, lower alkylamino-lower alkyl groups, lower alkoxy groups, lwoer alkoxy-lower alkoxy groups, lower alkoxy-lower alkyl groups, a thio group and lower alkylamido groups, a tetrahydropyranylthio group, a pyridylthio group, a lower alkylenedioxy group, an amino group (this amino group may be substituted by a lower alkanoyl group, a phenyl-lower alkyl group which may have a lower alkoxy group as a substituent on the phenyl ring, a lower alkenyl group, a hydroxy-lower alkyl group or a lower alkenyl group, a hydroxy-lower alkyl group or a lower alkyl group), a hydroxyl group, a lower alkylthio group, a lower alkanoyloxy group, a tetrahydropyranyloxy group, a halogen atom, a lower alkanoyl group, a mercapto group, a lower alkoxycarbonyl group, a carboxy group, a lower alkoxy group, an amido group or a lower alkylamido group, with the proviso that when n is 0, $R^{16}$ must be a 5-membered or 6-membered saturated or unsaturated heterocyclic group which may have, as substituent(s) on the heterocycle, 1-3 groups selected from the group consisting of hydroxy-lower alkyl groups, lower alkanoyloxy-lower alkyl groups, a hydroxyl group, lower alkyl groups, amino-lower alkyl groups, lower alkylamino-lower alkyl groups, lower alkoxy groups, lower alkoxy-lower alkoxy groups, lower alkoxy-lower alkyl groups, a thio group and lower alkylamido groups.)

The reaction of a compound of the general formula (20) with a compound of the general formula (21) can be effected under the same conditions as in the reaction of the compound of the general formula (17) with the compound of the general formula (18).

The reactions for converting into a compound of the general formula (22) and a compound of the general formula (3c) can be effected in the same conditions as in the reaction for converting the compound of the general formula (19) to the compound of the general formula (3b).

[Reaction formula-13]

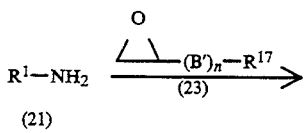

(21)

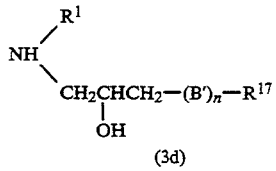

(3d)

[in the formula, R$^1$, B', n and X have the same definitions as above, with the proviso that the carbon atoms of the group

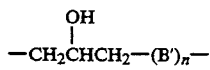

are not more than 6; and R$^{17}$ represents a hydrogen atom, an amino group (this amino group may be substituted by a lower alkanoyl group, a phenyl-lower alkyl group which may have a lower alkoxy group as a substituent on the phenyl ring, a lower alkenyl group, a hydroxy-lower alkyl group or a lower alkyl group), a hydroxyl group, a lower alkylthio group, a lower alkanoyloxy group, a tetrahydropyranyloxy group, a halogen atom, a lower alkanoyl group, a mercapto group, a lower alkoxycarbonyl group, a carboxy group, a lower alkoxy group, an amido group or a lower alkylamido group.]

The reaction of a compound of the general formula (21) with a compound of the general formula (23) is effected in a solventless state or in an appropriate solvent in the presence or absence of a basic compound. As to the solvent, there can be used singly or in combinations, for example, ethers such as dioxane, tetrahydrofuran, diethyl ether, ethylene glycol dimethyl ether and the like; aromatic hydrocarbons such as benzene, toluene, xylene and the like; lower alcohols such as methanol, ethanol, isopropanol and the like; and aprotic polar solvents such as dimethylformamide, dimethyl sulfoxide, hexamethylphosphoric triamide, N-methylpyrrolidone and the like. As to the basic compound, there can be used, for example, inorganic basic compounds such as potassium carbonate, sodium carbonate, sodium hydroxide, sodium hydrogencarbonate, sodium amide and the like; and organic basic compounds such as triethylamine, tripropylamine, pyridine, quinoline and the like. The amount of the compound of the general formula (23) used can be usually at least about 1 mole, preferably about 1–5 moles per 1 mole of the compound of the general formula (21). Said reaction is effected usually at about room temeprature to 200° C., preferably at about room temperature to 120° C., and is complete generally in about 1–24 hours.

[Reaction formula-14]

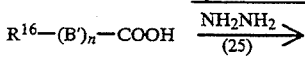

(24)

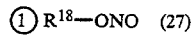

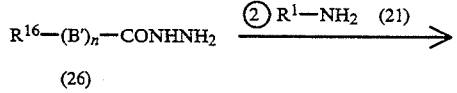

(26)

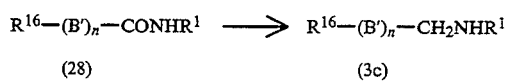

(28)                              (3c)

[in the formula R$^1$, R$^{16}$, B' and n have the same definitions as above, with the proviso that the carbon atoms of the group —(B')$_n$—CH$_2$— are not more than 6; and R$^{18}$ represents a hydrogen atom or a lower alkyl group.]

The reaction of a compound of the general formula (24) with hydrazine (25) can be effected under the same conditions as in the reaction of the compound of the general formula (2) with the compound of the general formula (3). For example, when an ester of the compound of the general formula (24) with a lower alcohol is reacted with hydrazine (25), the reaction is effected in a solventless state or in an appropriate solvent. As to the solvent used, there can be mentioned, for example, alcohols such as methanol, ethanol, propanol and the like; ethers such as tetrahydrofuran, diethyl ether, dimethoxyethane and the like; aromatic hydrocarbons such as benzene, toluene and the like; and aprotic polar solvents such as dimethyl formamide, dimethyl sulfoxide and the like. The amount of hydrazine used can be usually at least about 1 mole, preferably about 1.5–5 moels per 1 mole of the compound of the general formula (24). Said reaction is effected usually at about 0°–150° C., preferably about room temperature to 60° C., and is completed generally in about 5 minutes to 5 hours.

In the reaction for reacting an acid hydrazide of the general formula (26) with nitrous acid or its derivative of the general formula (27) to from an acid azide and then reacting the acid azide with an amine of the general formula (21) to obtain an acid amide of the general formula (28), there can be widely applied the conditions of the known azide method. As to the nitrous acid or its derivative of the general formula (27), there can be mentioned, for example, nitrous acid; nitrites such as sodium nitrite, potassium nitrite and the like; and alkyl nitrites such as ethyl nitrite, isoamyl nitrite and the like. The reaction for amide formation by the azide method is effected usually in a solvent. As to the solvent used, there can be mentioned, for example, water; organic acids such as acetic acid, propionic acid and the like; ethers such as dioxane, tetrahydrofuran, diethyl ether and the like; and aprotic polar solvents such as dimethylformamide, N-methylpiperidionone and the like. The amounts of the nitrous acid or its derivative of the general formula (27) and the amine of the general formula (21) are each at least about equimolar and usually a large excess relative to the compound of the general formula (26). Said reaction is effected usually at about −50° to 150° C., preferably at about −20° to 100° C., and is complete generally in about 1 hour to 5 days. The acid azide which is formed as an intermediate in the reaction may be isolated but is usually used in the subsequent reaction without being isolated.

The reaction for reducing the compound of the general formula (28) to obtain a compound of the general formula (3c) can be effected in the same conditions as in the reaction for converting the compound (16) into the compound (3a).

[Reaction formula-15]

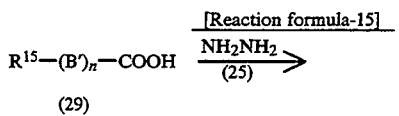

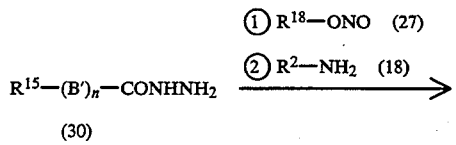

[in the formula $R^2$, $R^{15}$, $R^{18}$, B' and n have the same definitions as above, with the proviso that the carbon atoms of the group —(B')$_n$—CH$_2$— are not more than 6.]

The reaction of a compound of the general formula (29) with hydrazine (25) can be effected in the same conditions as in the reaction of the compound of the general formula (24) with hydrazine (25).

The reaction for obtaining a compound of the general formula (31) from a compound of the general formula (30) can be effected in the same conditions as in the reaction for converting the compound of the general formula (26) into the compound of the general formula (28).

The reaction for obtaining a compound of the general formula (3b) from the compound of the general formula (31) can be effected in the same conditions as in the reaction for converting the compound (28) to the compound (3c).

[Reaction formula-16]

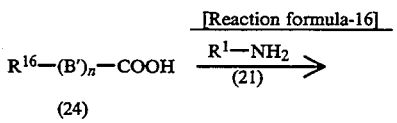

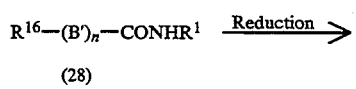

[in the formula $R^1$, $R^{16}$, B' and n have the same definitions as above, with the proviso that the carbon atoms of the group —(B')$_n$—CH$_2$— are not more than 6.]

The reaction of a compound of the general formula (24) with a compound of the general formula (21) can be effected in the same conditions as in the reaction of the compound of the general formula (2) with the compound of the general formula (3).

The reaction for reducing the compound of the general formula (28) to convert into a compound of the general formula (3c) was already described in the reaction formula 14.

[Reaction formula-17]

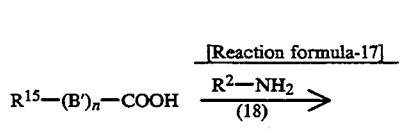

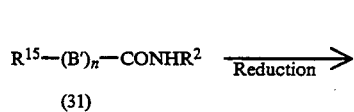

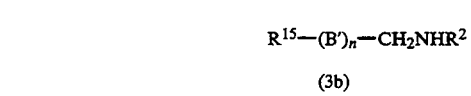

[in the formula, $R^2$, $R^{15}$, B' and n have the same definitions as above, with the proviso that the carbon atoms of the group —(B')$_n$—CH$_2$— are nor more than 6.]

The reaction of a compound of the general formula (29) with a compound of the general formula (18) can be effected in the same conditions as in the reaction of the compound of the general formula (2) with the compound of the general formula (3).

The reaction for converting a compound of the general formula (31) into a compound of the general formula (3b) was already described in the reaction formula 15.

[Reaction formula-18]

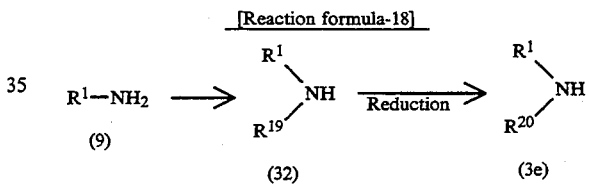

(in the formula, $R^1$ has the same definition as above; $R^{19}$ represents a lower alkanoyl group; and $R^{20}$ represents a lower alkyl group.)

The reaction for converting a compound of the general formula (9) into a compound of the general formula (32) can be effected in the same conditions as in the reaction for converting the compound of the general formula (1e) to the compound of the general formula (1f).

The reaction for reducing the compound of the general formula (32) to convert into a compound of the general formula (3e) can be effected under the same conditions as in the reaction for converting the compound of the general formula (16) into the compound of the general formula (3a).

[Reaction formula-19]

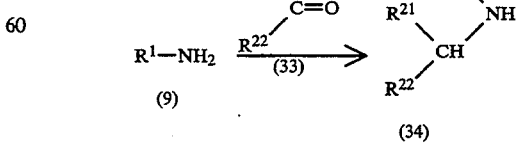

(in the formula, $R^1$ has the same definition as above; and $R^{21}$ and $R^{22}$ each represent a hydrogen atom or a lower alkyl group.)

The reaction of a compound of the general formula (9) with a compound of the general formula (33) is effected in a solventless state or in an appropriate solvent in the presence of a reducing agent. As to the solvent used therein, there can be mentioned, for example, water; alcohols such as methanol, ethanol, isopropanol and the like; lower alkanoic acids such as formic acid, acetic acid and the like; ethers such as dioxane, tetrahydrofuran, diethyl ether, diglyme and the like; and aromatic hydrocarbons such as benzene, toluene, xylene and the like. As to the reducing agent, there can be mentioned, for example, formic acid; alkali metal or alkaline earth metal salts of formic acid such as sodium formate and the like; hydride reducing agents such as sodium boron hydride, sodium boron cyanohydride, lithium aluminum hydride and the like; and catalytic reducing agents such as palladium black, palladium carbon, platinum oxide, platinum black, Raney nickel and the like. When formic acid is used as the reducing agent, the appropriate reaction temperature is usually about room temperature to 200° C., preferably about 50°–100° C., and the reaction is complete generally in about 0.5–10 hours. The amount of formic acid used can be about 0.1–20% by weight based on the compound of the general formula (9). The compound of the general formula (33) can be used usually in at least about an equimolar amount, preferably in an equimolar amount to a large excess relative to the compound of the general formula (9).

When the compound of the general formula (1), the compound of the general formula (3), the compound of the general formula (9) and the compound of the general formula (11) are respective compounds having, as $R^1$, a cycloalkyl-lower alkyl group having an amino-lower alkyl group, respective compounds having, as $R^2$, a 5-membered or 6-membered saturated or unsaturated heterocycle-lower alkyl group having at least one amino-lower alkyl group, or respective compounds having, as $R^2$, a lower alkyl group having at least one amino group, they can be converted, by treating under the same conditions as in the reaction shown by the reaction formula 19 or under the same conditions or by reacting with a compound represented by the general formula $R^{23}X$ ($R^{23}$ represents a lower alkyl group and X has the same definition as above) udner the same conditions as in the reaction of the compound of the general formula (4) with the compound of the general formula (5), to a compound of the general formula (1), a compound of the general formula (3), a compound of the general formula (9) and a compound of the general formula (11) each having, as $R^1$, a cycloalkyl-lower alkyl group having a lower alkylamino-lower alkyl group; a compound of the general formula (1), a compound of the general formula (3), a compound of the general formula (9) and a compound of the general formula (11) each having, as $R^2$, a 5-membered or 6-membered saturated or unsaturated heterocycle-lower alkyl group having at least one lower alkyl-substituted amino-lower alkyl group; or a compound of the general formula (1), a compound of the general formula (3), a compound of the general formula (9) and a compound of the general formula (11) each having, as $R^2$, a lower alkyl-substituted lower alkyl group.

When the compound of the general formula (1), the compound of the general formula (3) and the compound of the general formula (11) are respective compounds having, as $R^2$, a 5-membered or 6-membered saturated or unsaturated heterocycle-lower alkyl group having a nitrogen atom in the heterocycle, they can be converted, by treating under the same conditions as in the reaction shown by the reaction formula 19 or by reacting with a compound represented by the general formula $R^{23}X$ ($R^{23}$ and X have the same definitions as above) under the same conditions as in the reaction of the compound of the general formula (4) with the compound of the general formula (5), to a compound of the general formula (1), a compound of the general formula (3) and a compound of the general formula (11) each having, as $R^2$, a 5-membered or 6-membered heterocycle-lower alkyl group having a lower alkyl group on the nitorgen atom of the heterocycle.

When the compound of the general formula (1), the compound of the general formula (3) and the compound of the general formula (11) are respective compounds having, as $R^2$, a 5-membered or 6-membered saturated or unsaturated heterocycle-lower alkyl having at least one lower alkylamido group, respective compounds having, as $R^2$, a lower alkyl group having at least one amido or lower alkylamido group, or respective compounds having, as $R^2$, a lower alkyl group having at least one lower alkanoylamino group, they can be converted, by treating under the same conditions as in the reaction for converting the compound of the general formula (16) to the compound of the general formula (3a), to a compound of the general formula (1), a compound of the general formula (3) and a compound of the general formula (11) each having, as $R^2$, a 5-membered or 6-membered saturated or unsaturated heterocycle-lower alkyl group having at least one lower alkylaminomethyl group; a compound of the general formula (1), a compound of the general formula (3) and a compound of the general formula (11) each having, as $R^2$, a lower alkyl group having at least one amino or lower alkylamino group; or a compound of the general formula (1), a compound of the general formula (3) and a compound of the general formula (11) each having, as $R^2$, a lower alkyl group having at least one lower alkylamino group.

When the compound of the general formula (1), the compound of the general formula (3) and the compound of the general formula (11) are respective compounds having, as $R^2$, a lower alkyl group having at least one carboxy group, they can be converted, by treating under the same conditions as in the reaction of the compound of the general formula (2) with the compound of the general formula (3), into a compound of the general formula (1), a compound of the general formula (3) and a compound of the general formula (11) each having, as $R^2$, a lower alkyl group having at least one amido or lower alkylamido group.

When the compound of the general formula (1), the compound of the general formula (3) and the compound of the general formula (11) are respective compounds having, as $R^2$, a 5-membered or 6-membered saturated or unsaturated heterocycle-lower alkyl group having at least one hydroxyl group, they can be converted, by treating with a compound represented by the general formula

R24X (R24 represents a lower alkoxy-lower alkyl group and X has the same definition as above) udner the same conditions as in the reaction of the compound of the general formula (4) with the compound of the general formula (5), to a compound of the general formula (1), a compound of the general formula (3) and a compound of the general formula (11) each having as R2, a 5-membered or 6-membered saturated or unsaturated heterocycle-lower alkyl group having at least one lower alkoxy-lower alkoxy group.

When the compound of the general formula (1), the compound of the general formula (3) and the compound of the general formula (11) are respective compounds each having, as R2, a lower alkyl group having at least one carboxyl or lower alkoxycarbonyl group, they can be converted, by reacting with hydrazine (25) under the same conditions as in the reaction of the compound of the general formula (24) with hdyrazine (25) and then treating the resulting compound with the compound of the general formula (27) and an amine which may have a lower alkyl group in this order under the same conditions as in the reaction of the compound of the general formula (26) with the compound of the general formula (27) and the subsequent reaction with the amine of the general formula (21), to a compound of the general formula (1), a compound of the general formula (3) and a compound of the general formula (11) each having, as R2, a lower alkyl group having at least one amido or lower alkyl-amido group.

When the compound of the general formula (1), the compound of the general formula (3) and the compound of the general formula (11) are respective compounds having, as R2, a 5-membered or 6-membered saturated or unsaturated heterocycle-lower alkyl group having at least one hydroxy-lower alkyl group or at least one hydroxyl group, or respective compounds having, as R2, a lower alkyl group having at least one hydroxyl group, they can be converted, by reacting with a compound represented by the general formula

R23X (R23 and X have the same definitions as above) under the same conditions as in the reaction of the compound of the general formula (4) with the compound of the general formula (5), to a compound of the general formula (1), a compound of the general formula (3) and a compound of the general formula (11) each having, as R2, a 5-membered or 6-membered saturated or unsaturated heterocycle-lwoer alkyl group having at least one lower alkoxy-lower alkyl group or at least one lower alkoxy group, or a compound of the general formula (1), a compound of the general formula (3) and a compound of the general formula (11) each having, as R2, a lower alkyl group having at least one lower alkoxy group.

When the compound of the general formula (1), the compound of the general formula (3) and the compound of the general formula (11) are respective compounds having, as R2, a lower alkyl group having at least one amino group, they can be converted, by subjecting to lower alkanoylation under the same conditions as in the reaction for converting the compound of the general formula (1e) into the compound of the general formula (1f), to a compound of the general formula (1), a compound of the general formula (3) and a compound of the general formula (11) each having, as R2, a lower alkyl group having at least one lower alkanoylamino group.

The compound of the general formula (11) used above can also be produced according to, for example, the process shown by the following reaction formula.

[Reaction formula-20]

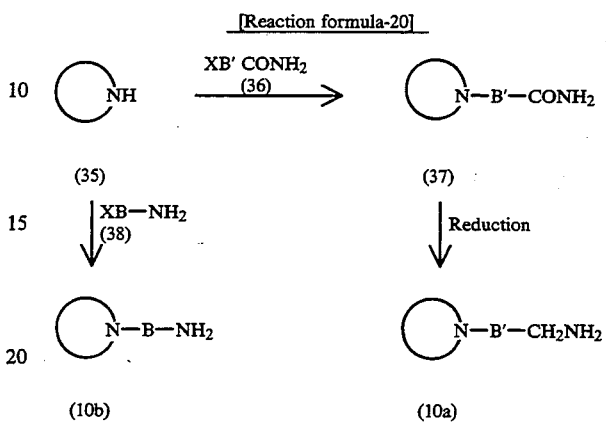

(in the formula, B, B', X and the group

have the same definitions as above.)

The reaction of a compound of the general formula (35) with a compound of the general formula (36) can be effected under the same conditions as in the reaction of the compound of the general formula (4) with the compound of the general formula (5).

The reaction of the compound of the general formula (35) with a compound of the general fromula (38) can also be effected under the same conditions as in the reaction of the compound of the general formula (4) with the compound of the general formula (5).

The reduction reaction of a compound of the general formula (41) can be effected under the same conditions as in the reaction for converting the compound of the general formula (16) to the compound of the general formula (3a).

The compound of the general formula (20) used above can be produced according to, for example, the process shown by the following reaction formula.

[Reaction formula-21]

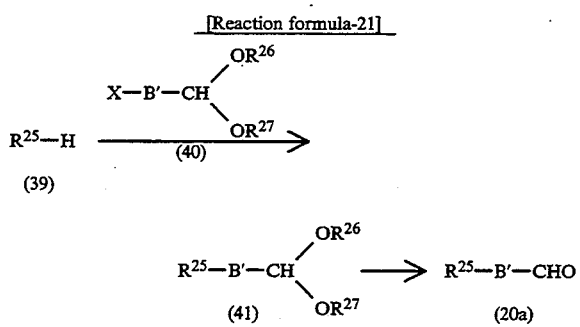

(in the formula, R25 represents a pyridylthio group or a tetrahydropyranylthio group; R26 and R27 each represent a lower alkyl group; and B' and X have the same definitions as above.)

The reaction of a compound of the general formula (39) with a compound of the general formula (40) can be effected under the same conditions as in the reaction of the compound of the general formula (4) with the compound of the general formula (5).

The reaction for converting a compound of the general formula (41) into a compound of the general formula (20a) can be effected under the same conditions as in the reaction for converting the compound of the general formula (1d) into the compound of the general formula (1e).

Of the compounds represented by the general formula (1), those having an acidic group can form respective salts with a pharmaceutically acceptable basic compound. As to such a basic compound, there can be specifically mentioned, for example, sodium hydroxide, potassium hydroxide, calcium hydroxide, calcium carbonate and potassium hydrogencarbonate.

Also, of the compounds represented by the general formula (1), those having a basic group can form respective salts with a pharmaceutically acceptable acid. As to such an acid, there can be mentioned specifically inorganic acids such as sulfuric acid, phosphoric acid, nitric acid, hydrochloric acid, hydrobromic acid and the like, as well as organic acids such as oxalic acid, maleic acid, fumaric acid, malic acid, tartaric acid, citric acid, benzoic acid and the like.

The thus obtained compound of the present invention can be easily isolated and purified according to a separation means used generally. As to such a separation means, there can be mentioned, for example, a precipitation method, an extraction method, a recrystallization method, column chromatography, and preparative thin layer chromatography.

The compound of the present invention can be administered to animals and human beings as it is or together with a conventional pharmaceutical carrier. The unit form for administering the present compound is not restricted and can be selected appropriately so as to meet the administration purpose. As to the unit form for administration, there can be mentioned, for example, agents for oral administration such as tablet, granule, solution for oral administration and the like, and agents for parenteral administration such as injection and the like. The amount of the active ingredient to be administered is not restricted and can be appropriately selected in a wide range; however, the amount is preferably about 0.06–10 mg in order to obtain a desired effect. Further, the active ingredient is preferably contained in one administration unit form in an amount of about 1–100 mg.

In the present invention, agents for oral administration such as tablet, capsule, solution for oral administration and the like can be prepared according to a conventional method. That is, tablets are prepared by mixing a compound of the present invention with pharmaceutical fillers such as gelatin, starch, lactose, magnesium stearate, talc, gum arabic and the like. Capsules are prepared by mixing a compound of the present invention with an inactive pharmaceutical filler or diluent and filling the mixture in a hard gelatin capsule, a soft capsule or the like. Medicated syrups or elixirs are prepared by mixing a compound of the present invention with a sweetening (e.g. saccharose), an antiseptic (e.g. methylparaben, propylparaben), a coloring agent, a seasoning, etc. That is, drugs for parenteral administration are prepared by dissolving a compound of the present invention in a sterilized carrier. A preferable carrier is water or salt water. Solutions having a desired transparency, stability and parenteral usability are prepared by dissolving about 1–500 mg of an active ingredient in water and an organic solvent and further in a polyethylene glycol having a molecular weight of 200–5,000. These solutions preferably contain a wetting agent such as sodium carboxymethyl cellulose, methyl cellulose, vinylpyrrolidone, polyvinyl alcohol and the like. These solutions may further contain a bactericide and fungicide (e.g. benzyl alcohol, phenol, thimerosol)and, as necessary, a tonicity agent (e.g. saccharose, sodium chloride), a local anesthetic, a stabilizer, a buffer, etc. In order to increase the stability, drugs for parenteral administration can be dehydrated by, after filling, subjecting to the freeze-drying technique which is known in the art. Thus, a freeze-dried powder can be reprepared right before use.

In order to describe the present invention in further details, there are mentioned below examples (reference examples(for preparing the material compounds for compounds of the present invention, examples for preparing compounds of the present invention, pharmacological tests conducted on compounds of the present invention, and examples of drugs containing compounds of the present invention.

Reference Example 1

5.66 Grams of cyclohexylmethylamine is dissolved in 200 ml of diethyl ether. Thereto is added 5.06 g of triethylamine. To the resulting mixture is dropwise added, with ice cooling, a solution of 5.65 g of chloroacetyl chloride dissolved in 150 ml of diethyl ether. The mixture is stirred for 1 hour at room temperature and then acidified with 5% hydrochloric acid. The mixture is extracted with diethyl ether. The extract is washed with water and dried with anhydrous magnesium sulfate. The solvent is removed by evaporation and the residue is recrystallized from n-hexane to obtain 6.7 g of N-cyclohexylmethyl-N-($\alpha$-chloroacetyl)amine.

Properties: Colorless acicular crystals
Melting point: 85°–86° C.

Reference Example 2

4.00 Grams of N-cyclohexyl-N-($\alpha$-chloroacetyl)amine is dissolved in 80 ml of ethanol. Thereto are added 1.50 g of pyrrolidine and further 4.37 g of potassium carbonate. The mixture is refluxed with heating. Then, the solvent is removed by evaporation. The resulting crude oily material is purified by a silica gel column chromatography (chloroform:methanol=50:1) to obtain 4.78 g of N-cyclohexylmethyl-N-[$\alpha$-(1-pyrrolidinyl)acetyl]amine.

Properties: Colorless oily substance
$^1$H-NMR (CDCl$_3$) $\delta$ ppm:
0.86–2.00 (15H, m)
2.56–2.76 (4H, m)
3.03–3.22 (2H, t, J=7 Hz)
3.15 (2H, s)

Reference Example 3

2.40 Grams of lithium aluminum hydride is suspended in 100 ml of anhydrous tetrahydrofuran. Thereto is dropwise added a solution of 4.78 g of N-cyclohexylmethyl N-[$\alpha$-(1-pyrrolidinyl)acetyl]amine dissolved in 50 ml of anhdyrous tetrahydrofuran. The mixture is refluxed for 3 hours with heating. Thereto are added 8 ml of 10% aqueous potassium hydroxide solution and 8 ml of water, and the mixture is refluxed for 10 minutes with heating. Aluminum hydroxide is removed by filtration. The filtrate is dried with anhydrous magnesium sulfate and the solvent is removed by evaporation. The residue is purified by a thin layer chromatography to obtain 0.70 g of N-cyclohexylaminomethyl-N-[2-(1-pyrrolidinyl)ethyl]amine.

Properties: Colorless oily substance
$^1$H-NMR (CDCl$_3$) δ:
0.80–2.29 (16H, m)
2.44 (2H, d, J=7 Hz)
2.49–2.56 (4H, m)
2.59 (2H, t, J=6 Hz)
2.71 (2H, t, J=6 Hz)

Reference Examples 4–6

Using appropriate starting materials and in the same procedure as in Reference Example 1, there are obtained compounds shown in Table 1 given later.

Reference Examples 7–31

Using appropriate starting materials and in the same procedure as in Reference Example 2, there are obtained compounds shown in Table 2 given later.

Reference Examples 32–56

Using appropriate starting materials and in the same procedure as in Reference Example 3, there are obtained compounds shown in Table 3 given later.

Reference Example 57

1.13 Grams of cyclohexylmethylamine and 1.51 g of 1,2-isopropylidenedioxy-3-chloropropanediol are dissolved in 15 ml of dimethylformamide. To the solution are added 1.66 g of potassium carbonate and 3.00 g of sodium iodide, and the mxiture is refluxed for 4 hours with heating. Dimethylformamide is removed by evaporation under reduced pressure. The residue obtained is extracted with diethyl ether. The extract is washed with water, dried and subjected to solvent removal by evaporation. The resulting crude oily substance is subjected to distillation under reduced pressure to obtain 1.25 g of N-cyclohexylmethyl-N-(2,3-isopropylidenedioxypropyl)amine.

Properties: Colorless oily substance
Boiling point: 120° C./0.3 mmHg

Reference Examples 58–64

Using appropriate starting materials and in the same procedure as in Reference Example 57, there are obtained compounds shown in table 4 given later.

Reference Example 65

To 100 ml of ethanol were added 7.0 g of cyclooctylaldehyde and 5.4 g of 3-aminomethylpyridine, and the mixture was subjected to a reaction for 4 hours at about 50° C. After cooling, 2.0 g of sodium boron hydride was added while 20° C. or below was kept by ice cooling, and the mixture was subjected to a reaction for 1 hour at room temperature. The reaction mixture was acidified with 2N hydrochloric acid and concentrated to dryness. To the residue was added an aqueous potassium carbonate solution to make the residue alkaline. The mixture was extracted with chloroform. The extract was washed with water and then dried with anhydrous sodium sulfate. The solvent was removed by evaporation. The residue was subjected to distillation under reduced pressure to obtain 6.4 g of N-(cyclohexylmethyl)-N-(3-pyridylmethyl)amine.

Properties: Colorless oily substance
Boiling point: 132°–140° C./0.2 mmHg

Reference Example 66

5.81 Grams of N,N-diethylaminoethylenediamine and 7.01 g of cyclooctylaladehyde are dissolved in 50 ml of ethanol. The mixture is stirred for 8 hours at room temperature. Thereto is added 0.5 g of 10% palladium carbon (Pd—C). The mixture is subjected to hydrogenation for 2 hours at 50° C. or below at 5 kg/cm$^2$. The catalyst is removed by filtration. The filtrate is subjected to evaporation under reduced pressure to remove ethanol. The resulting crude oily substance is subjected to distillation under reduced pressure to obtain 6.5 g of N-(2-diethylaminoethyl)-N-(cyclooctylmethyl)amine.

Properties: Colorless oily substance
Boiling point: 113° C./2 mmHg

Reference Examples 67–106

Using appropriate starting materials and in the same procedure as in Reference Examples 65 and 66, there are obtained compounds shown in Table 5 given later.

Reference Example 107

6.7 Grams of epichlorohydrin and 10.2 g of cyclohexylmethylamine are dissolved in 50 ml of methanol. The mixture is stirred for 8 hours at room temperature. Methanol is removed by evaporation under reduced pressure. The resulting crude oily substance is purified by a silica gel column chromatography (chloroform:methanol=8:1) to obtain 8.2 g of N-(dicyclohexylmethyl)-N-(3-chloro-2-hydroxypropyl)amine.

Properties: Colorless oily substance
$^1$H-NMR (CDCl$_3$) δ ppm:
0.75–1.09 (2H, m)
1.09–1.37 (3H, m)
1.47 (1H, m)
1.61–1.92 (5H, m)
2.48 (2H, m)
2.68 (1H, dd, J=12 Hz, 8 Hz)
2.80 (1H, dd, J=12 Hz, 4 Hz)
3.16 (2H, s)
3.55 (2H, d, J=6 Hz)

Reference Examples 108–112

Using appropriate starting materials and in the same procedure as in Reference Example 107, there are obtained compounds shown in Table 6 given later.

Reference Example 113

6.35 Grams of 1-benzyloxycarbonyl-2β-methoxycarbonyl-4α-methoxymethoxypyrrolidine is dissolved in 120 ml of methanol. To the solution is dropwise added 1.89 g of 100% hydrazine with ice cooling. The mixture is stirred overnight at room temperature. The solvent is removed by evaporation under reduced pressure. The resulting residue is purified by a silica gel short column chromatography (chloroform:methanol=8:1) to obtain 6.35 g of (1-benzyloxycarbonyl-4α-methoxymethyl-2β-pyrrolidinyl)hydrazide.

Properties: Colorless oily substance
$^1$H-NMR (CDCl$_3$) δ ppm:
2.12–2.52 (2H, m)
3.31 (3H, s)
3.54–4.14 (4H, m)
4.29–4.45 (2H, m)
4.63 (2H, s)
4.99–5.28 (2H, m)

7.35 (5H, s)
8.03 (1H, s)

Reference Example 114

6.80 Grams of (1-benzyloxycarbonyl-4α-methoxymethoxy-2β-pyrrolidinyl)hydrazide is dissolved in 300 ml of dimethylformamide (DMF). Thereto is added a solution of 5N hydrochloric acid dissolved in 10 ml of DMF. The mixture is cooled to −20° C. and 2.46 g of isoamyl nitrite is added. In 5 minutes, triethylamine is added to the solution to make the pH of the solution 8. 2.38 g of cyclohexylmethylamine is added and the mixture is allowed to stand for 48 hours at 4° C. DMF is removed by distillation under reduced pressure. The residue is dissolved in diethyl ether. The solution is washed with water and dried with anhydrous magnesium sulfate. The solvent is removed by evaporation. The resulting residue is purified by a silica gel column chromatography (chloroform:methanol=20:1) to obtain 6.60 g of 1-benzyloxycarbonyl-2β-cyclohexylmethylamido-4α-methoxymethoxypyrrolidine.

Properties: Colorless oily substance
$^1$H-NMR (CDCl$_3$) δ ppm:
0.71–1.80 (11H, m)
2.00–2.62 (2H, m)
2.88–3.18 (2H, m)
3.33 (3H, s)
3.48–3.72 (2H, m)
4.25–4.45 (2H, m)
4.63 (2H, s)
5.16 (2H, s)
6.76 (1H, s)
7.34 (5H, s)

Reference Example 115

4.15 Grams of 1-benzyloxycarbonyl-2β-cyclohexylmethylamido-4α-methoxymethoxypyrrolidine is dissolved in 100 ml of ethanol. Thereto is added 10% Pd—C. Hydrogenation is effected for 3 hours at room temperature at 3 kg/cm$^2$. The catalyst is removed by filtration. The filtrate is subjected to vacuum evaporation to remove the solvent. The residue is purified by a thin layer chromatography to obtain 2.78 g of 2β-cyclohexylmethylamido-4α-methoxymethoxypyrrolidine.

Properties: Colorless oily substance
$^1$H-NMR (CDCl$_3$) δ ppm:
0.84–1.90 (11H, m)
2.04 (1H, m), 2.60 (1H, m)
2.95–3.28 (3H, m)
3.37 (1H, m), 3.38 (1H, s)
4.30–4.52 (2H, m)
4.65 (2H, dd, J=12 Hz, 7 Hz)
8.23 (1H, s)

Reference Example 116

Using appropriate starting materials and in the same procedure as in Reference Example 3, there is obtained 1-ethyl-2β-cyclohexylmethylaminomethyl-4α-methoxymethoxypyrrolidine.

Properties: Colorless oily substance
$^1$H-NMR (CDCl$_3$) δ ppm:
0.84–1.94 (12H, m)
1.94–3.05 (10H, m)
3.40 (3H, s)
3.30–3.53 (1H, m)
4.38 (1H, m)
4.68 (2H, m)

Reference Example 117

1.50 Grams of 2β-cyclohexylmethylamido-4α-methoxymethoxypyrrolidine is dissolved in 20 ml of ethanol. Thereto are added 0.43 g of ethyl iodide and 1.76 g of potassium carbonate. The mixture is refluxed for 2 hours with heating. The solvent is removed by evaporation. The resulting reaction mixture is purified by a silica gel column chromatography (chloroform:methanol=20:1) to obtain 0.43 g of 1-ethyl-2β-cyclohexylmethylamido-4α-methoxymethoxypyrrolidine.

Properties: Colorless oily substance
$^1$H-NMR (CDCl$_3$) δ ppm:
0.84–1.94 (12H, m)
1.94–3.05 (10H, m)
3.40 (3H, s)
3.30–3.53 (1H, m)
4.38 (1H, m), 4.68 (2H, m)

Reference Example 118

1.30 Grams of 1-ethyl-2β-cyclohexylmethylaminomethyl-4α-methoxymethoxypyrrolidine is dissolved in 6N hydrochloric acid. The solution is stirred for 1 hour at room temperature. A 10% aqueous potassium hydroxide solution is added to the solution to make it alkaline. The alkaline solution is extracted with methylene chloride. The extract is washed with water and dried with anhydrous magnesium sulfate. The solvent is removed by evaporation. The residue is purified by a thin layer column chromatography to obtain 0.75 g of 1-ethyl-2β-cyclohexylmethylaminomethyl-4α-hydroxypyrrolidine.

Properties: Colorless oily substance
$^1$H-NMR (CDCl$_3$) δ ppm:
1.07 (3H, t, J=7 Hz)
0.76–2.10 (14H, m)
2.20 (1H, dd, J=10 Hz, 5 Hz)
2.31 (1H, dd, J=10 Hz, 7 Hz)
2.42 (2H, d, J=8 Hz)
2.53 (1H, dd, J=13 Hz, 8 Hz)
2.72 (1H, dd, J=13 Hz, 5 Hz)
2.78–2.97 (2H, m)
3.37–3.55 (1H, m)
4.39 (1H, m)

Reference Example 119

There are mixed 1.60 g of 5β-methoxycarbonyl-3β-methylthiomorpholine, 2.22 g of a formalin solution and 45 ml of formic acid. The mixture is refluxed for 40 minutes with heating. The solvent is removed by evaporation. The residue is dissolved in water. The solution is neutralized with an aqueous solution saturated with sodium hydrogen carbonate. The resulting solution is extracted with ethyl acetate. The extract is dried with anhydrous magnesium sulfate. The solvent is removed by evaporation. The residue is purified by a silica gel column chromatography (dichloromethane:methanol=40:1) to obtain 1.73 g of 3,4β-dimethyl-5β-methoxycarbonylthiomorpholine.

Properties: Light brown and oily
$^1$H-NMR (CDCl$_3$) δ ppm:
1.24 (3H, t, J=6 Hz)
2.24 (3H, s)
2.27–2.68 (3H, m)
2.74 (1H, dd, J=13 Hz, 11 Hz)
2.98 (1H, dd, J=13 Hz, 11 Hz)
3.36 (1H, dd, J=11 Hz, 2 Hz)

3.76 (3H, s)

Reference Example 120

Using 13.33 ml of hydrazine monohydrate and 1.73 g of 3,4β-dimethyl-5β-methoxycarbonylthiomorpholine and in the same procedure as in Reference Example 113, there is obtained 0.91 g of (3,4β-dimethyl-5β-thiomorpholinyl)hydrazide.

Properties: Colorless solid
Melting point: 118°–119° C.

Reference Example 121

Using 0.91 g of (3,4β-dimethyl-5β-thiomorpholinyl)hydrazide, 0.64 ml of isoamyl nitrite and 1.02 g of cyclooctylmethylamine and in the same procedure as in Reference Example 114, there is obtained 0.95 g of 3,4β-dimethyl-5β-cyclooctylmethylamidothiomorpholine.

Properties: Light purple acicular crystals
Melting point: 72° C.

Reference Example 122

Using appropriate materials and in the same procedure as in Reference Example 3, there is obtained 3,4β-dimethyl-5β-cyclooctylmethylaminomethylthiomorpholine.

Properties: Colorless solid
$^1$H-NMR (CDCl$_3$) δ ppm:
1.16 (3H, d, J=6 Hz)
1.22–1.82 (16H, m)
1.94–2.10 (2H, m)
2.13 (3H, s)
2.44 (2H, dd, J=7 Hz, 4 Hz)
2.54–2.84 (4H, m)
3.15 (1H, m)

Reference Example 123

70 Milliliters of formic acid and 70 ml of a 35% formalin solution are added to 20 g of nipecotic acid. The mixture is refluxed for 8 hours with stirring. The reaction mixture is concentrated. The residue is mixed with chloroform and the mixture is concentrated (this procedure is conducted twice). The residue is acidified with 2N hdyrochloric acid and then concentrated. The residue is mixed with dichloromethane to effect crystallization to obtain 20.2 g of 1-methylnipecotic acid hydrochloride.

Properties: White powdery crystals
$^1$H-NMR (CDCl$_3$) δ ppm:
1.30–2.00 (4H, m)
2.45–2.91 (4H, m)
2.61 (3H, s)
3.05–3.36 (2H, m)
9.01 (1H, s)

Reference Example 124

To 80 ml of chloroform were added 3.59 g of 1-methylnipecotic acid hydrochloride and 6.26 ml of triethylamine. Thereto was added 3.0 g of isobutyl chloroformate under ice cooling and stirring. The mixture was stirred for 30 minutes. Thereto was added 3.1 g of cyclooctylmethylamine, and the mixture was subjected to a reaction for 2 hours at room temperature. The reaction mixture was washed with an aqueous sodium hydrogen carbonate solution and with water, and dried with anhydrous sodium sulfate. The solvent was removed by evaporation. The residue was purified by a Silica gel column chromatography (dichloromethane:-methanol=10:1) to obtain 3.3 g of 1-methyl-3-cyclooctylmethylaminocarbonylpiperidine.

Properties: Colorless solid
$^1$H-NMR (CDCl$_3$) δ ppm:
1.14–2.00 (19H, m)
2.00–2.84 (5H, m)
2.28 (3H, s)
3.09 (2H, t, J=6 Hz)
8.00 (1H, s)

Reference Example 125

To 50 ml of distilled tetrahydrofuran were added 3.2 g of 1-methyl-3-cyclooctylmethylaminocarbonylpiperidine and 1.5 g of lithium aluminum hydride. The mixture was refluxed for 10 hours under a nitrogen current. After cooling, the reaction mixture was mixed with methanol and 2N sodium hydroxide. The resulting mixture was stirred and then the insoluble materials were removed by filtration. The filtrate was concentrated. The residue was distilled in a glass tube over under reduced pressure to obtain 2.6 g of N-(1-methyl-3-piperidinylmethyl)-N-cyclooctylmethylamine.

Properties: Colorless oily substance
Boiling point: 150° C./0.2 mmHg

Reference Example 126

Using appropriate starting materials and in the same procedure as in Reference Example 123, there are obtained the following compounds.

(1) 1-Methyl-2-carboxypiperidine

Properties: Colorless powdery crystals
Melting point: 177°–178° C.

(2) Trans-p-dimethylaminomethylcyclohexanecarboxylic Acid

Properties: Colorless scaly crystals
Melting point: 236°–238° C.

Reference Example 127

Using appropriate starting materials and in the same procedure as in Reference Example 124, there are obtained the following compounds.

(1) 1-Methyl-2-cyclohexylmethylamidopiperidine

Properties: Colorless and oily
$^1$H-NMR (CDCl$_3$) δ ppm:
0.83–1.87 (17H, m)
1.95–2.12 (2H, m)
2.20 (3H, s)
2.46 (1H, dd, J=11 Hz, 3 Hz)
2.90 (1H, s), 3.10 (2H, m)

(2) 1-Methyl-3-(2-tetrahydropyranyloxyethylamido)piperidine

Properties: Light yellow oily substance
$^1$H-NMR (CDCl$_3$) δ ppm:
1.40–1.97 (11H, m)
2.27 (3H, s)
2.40–2.78 (6H, m)
3.25 (1H, m)
3.34–3.61 (4H, m)
3.74–3.93 (2H, m)
4.60 (1H, s)

(3)
N-(4α-dimethylaminomethyl-1β-cyclohexylcarbonyl)-N-ethoxycarbonylmethylamine Properties: Brown oily substance
¹H-NMR (CDCl₃) δ ppm:
0.83–2.06 (12H, m)
1.28 (3H, t, J=7 Hz)
2.17 (1H, m)
2.42 (2H, d, J=7 Hz)
2.47 (6H, s)
4.00 (2H, d, J=5 Hz)
4.20 (2H, q, J=7 Hz)
6.37 (1H, s)

Reference Exampel 128

Using appropriate starting materials and in the same procedure as in Reference Example 125, there are obtained the following compounds.

(1)
(N-cyclohexylmethyl-N-(1-methyl-2-piperidinylmethyl)amine

Properties: Colorless oily substance
¹H-NMR (CDCl₃) δ ppm:
0.80–2.17 (20H, m)
2.26 (3H, s)
2.41 (2H, dd, J=7 Hz, 3 Hz)
2.66 (2H, d, J=6 Hz)
2.83 (1H, m)

(2)
N-(1-methyl-3-piperidinylmethyl)-N-(2-tetrahydropyranyloxyethyl)amine

Properties: Colorless oily substance
Boiling point: 180° C./0.2 mmHg (3)
N-ethyl-N-(4α-hydroxymethyl-1β-cyclohexylmethyl)amine Properties: Colorless acicular crystals
Melting point: 85°–86° C. (recrystallized from diethyl ether)

Reference Example 129

Using appropriate starting materials and in the same procedure as in Reference Example 113, there is obtained (2-hydroxy-1-diethylaminoethyl)hydrazide.

Properties: Colorless oily substance
¹H-NMR (CDCl₃) δ ppm:
1.06 (6H, t, J=7 Hz)
2.45–2.74 (4H, m)
3.37–4.48 (1H, m)
3.79 (1H, dd, J=11 Hz, 4 Hz)
3.98 (1H, dd, J=11 Hz, 8 Hz)
3.50–4.10 (3H, m)
8.38 (1H, s)

Reference Example 130

Using appropriate starting materials and in the same procedure as in Reference Example 114, there is obtained N-cyclooctylmethyl-N-(2-hydroxy-1-diethylaminoethylcarbonyl)amine.

Properties: Colorless oily substance
¹H-NMR (CDCl₃) δ ppm:
1.07 (6H, t, J=7 Hz)
1.17–1.91 (15H, m)
2.41–2.73 (4H, m)
2.91–3.40 (3H, m)
3.64–4.04 (2H, m)
7.59 (1H, s)

Reference Example 131

Using appropriate starting materials and in the same procedure as in Reference Example 3, there is obtained N-cyclooctylmethyl-N-(3-hydroxy-2-diethylaminopropyl)amine.

Properties: Colorless oily substance
¹H-NMR (CDl₃) δ ppm:
1.05 (6H, t, J=7 Hz)
1.15–1.78 (16H, m)
2.24–3.03 (9H, m)
3.53–3.76 (2H, m)

Reference Example 132

A solution of 5.7 g of 4α-hydroxymethyl-1β-cyclohexylmethylamine, 8.3 ml of acetic anhdyride and 100 ml of pyridine is stirred for 30 minutes at room temperature. After the completion of the reaction, pyridine is removed by evaporation under reduced pressure. The residue is acidified with 5% hydrochloric acid. The resulting material is extracted with chloroform. The extract is washed with water and dried with anhydrous magnesium sulfate. The solvent is removed by evaporation. The resulting crystals are recrystallized from diethyl ether to obtain 7.0 g of N-(4α-acetyloxymethyl-1β-cyclohexylmethyl)-N-acetylamine.

Properties: Colorless acicular crystals
Melting point: 82°–83° C.

Reference Example 133

Using appropriate starting materials and in the same procedure as in Reference Example 1, there is obtained N-diethyl-N-(α-chloroacetyl)amine.

Properties: Light yellow oily substance
¹H-NMR (CDCl₃) δ ppm:
1.15 (3H, t, J=7 Hz)
1.24 (3H, t, J=7 Hz)
3.30–3.49 (4H, m)
4.06 (2H, s)

Reference Example 134

Using appropriate starting materials and in the same procedure as in Reference Example 2, there is obtained N-cyclooctylmethyl-N-diethylamidomethylamine.

Properties: Light yellow and oily substance
¹H-NMR (CDCl₃) δ ppm:
1.12 (3H, t, J=7 Hz)
1.18 (3H, t, J=7 Hz)
1.23–1.85 (15H, m)
2.00 (1H, b)
2.42 (2H, d, J=7 Hz)
3.26 (2H, q, J=7 Hz)
3.35–3.44 (4H, m)

Reference Example 135

7.7 Grams of 1-chloro-2,4-methylenedioxybutane and 6.4 g of cyclohexylmethylamine are dissolved in 80 ml of dimethylformamide (DMF). Thereto are added 9.4 g of potassium carbonate and 17.0 g of sodiumiodide. The mixture is refluxed for 3 hours with heating. DMF is removed by evaporation under reduced pressure. The residue is extracted with diethyl ether. The extract is washed with water and dried with anhdyrous magnesium sulfate. The solvent is removed by evaporation. The residue is purified by a silica gel column chromatography (chloroform: methanol=20:1) and then subjected to distillation by glass tube oven to obtain 4.5 of N-(2,4-methylenedioxy-1-butyl)-N-cyclohexylmethylamine.

Properties: Colorless oily substance
Boiling point: 180° C./0.5 mmHg

Reference Examples 136–139

Using appropriate starting materials and in the same procedure as in Reference Example 135, there are obtained compounds shown in Table 7 given later.

In the following tables 1–7 are shown the compounds obtained in the above Reference Examples 4–56, 58–64, 67–106, 108–112 and 136–139.

The $^1$H-NMR (CDCl$_3$) δ ppm data of the compounds shown in the above tables are shown in Table 8.

TABLE 1

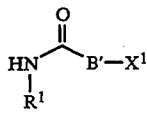

Reference Example 4

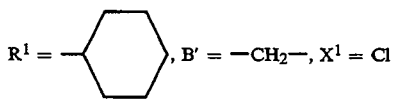

Properties: Colorless acicular crystals (recrystallized from n-hexane)
Melting point: 107–108° C.
Reference Example 5

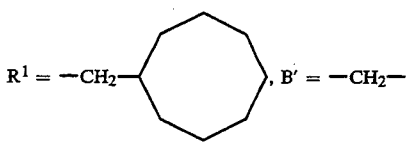

$X^1 = Cl$
Properties: Colorless acicular crystals (recrystallized from n-hexane)
Melting point: 75–76° C.
Reference Example 6

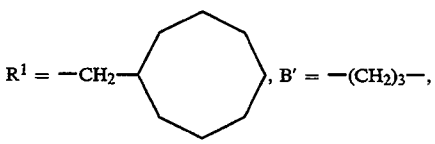

$X^1 = Cl$
Properties: Colorless oily substance
$^1$H-NMR (CDCl$_3$) δ ppm: See Table 8.

TABLE 2

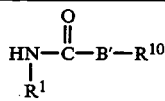

Reference Example 7

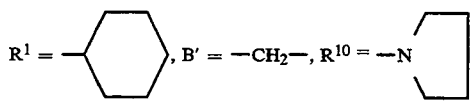

Properties: Colorless oily substance

TABLE 2-continued

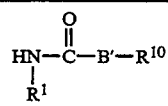

$^1$H-NMR (CDCl$_3$) δ ppm: See Table 8.
Reference Example 8

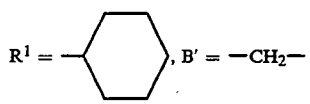

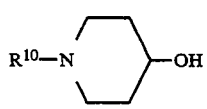

Properties: Colorless oily substance
$^1$H-NMR (CDCl$_3$) δ ppm: See Table 8.
Reference Example 9

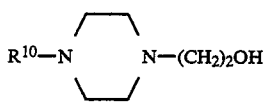

Properties: Colorless oily substance
$^1$H-NMR (CDCl$_3$) δ ppm: See Table 8.
Reference Example 10

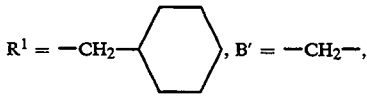

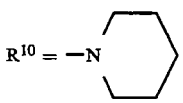

Properties: Colorless oily substance
$^1$H-NMR (CDCl$_3$) δ ppm: See Table 8.
Reference Example 11

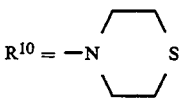

Properties: Colorless oily substance
$^1$H-NMR (CDCl$_3$) δ ppm: See Table 8.
Reference Example 12

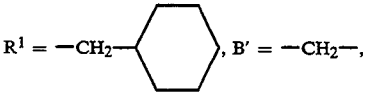

TABLE 2-continued $$\underset{R^1}{HN-\overset{O}{\overset{\|}{C}}-B'-R^{10}}$$

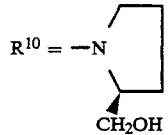

Properties: Colorless oily substance
¹H-NMR (CDCl₃) δ ppm See Table 8.
Reference Example 13

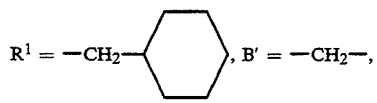

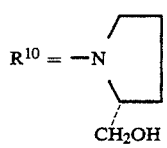

Properties: Colorless oily substance
¹H-NMR (CDCl₃) δ ppm: See Table 8.
Reference Example 14

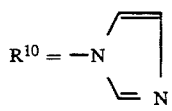

Properties: Colorless solid
¹H-NMR (CDCl₃) δ ppm: See Table 8.
Reference Example 15

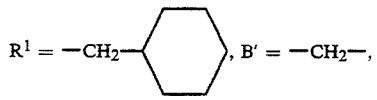

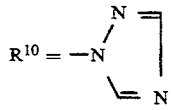

Properties: Light yellow oily substance
¹H-NMR (CDCl₃) δ ppm: See Table 8.
Reference Example 16

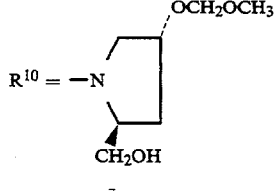

TABLE 2-continued $$\underset{R^1}{HN-\overset{O}{\overset{\|}{C}}-B'-R^{10}}$$

Properties: Colorless oily substance
¹H-NMR (CDCl₃) δ ppm: See Table 8.
Reference Example 17

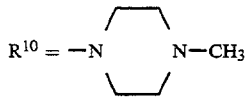

Properties: Colorless oily substance
¹H-NMR (CDCl₃) δ ppm: See Table 8.
Reference Example 18

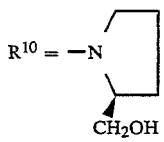

Properties: Colorless oily substance
¹H-NMR (CDCl₃) δ ppm: See Table 8.
Reference Example 19

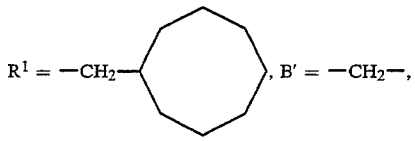

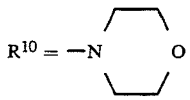

Properties: Colorless oily substance
¹H-NMR (CDCl₃) δ ppm: See Table 8.
Reference Example 20

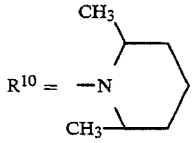

TABLE 2-continued

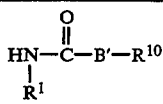

Properties: Colorless oily substance
$^1$H-NMR (CDCl$_3$) δ ppm: See Table 8.
Reference Example 21

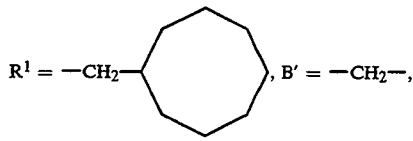
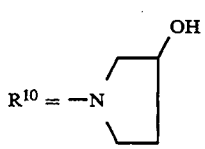

Properties: Colorless oily substance
$^1$H-NMR (CDCl$_3$) δ ppm: See Table 8.
Reference Example 22

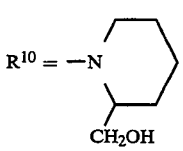

Properties: Colorless oily substance
$^1$H-NMR (CDCl$_3$) δ ppm: See Table 8.
Reference Example 23

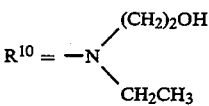

Properties: Colorless oily substance
$^1$H-NMR (CDCl$_3$) δ ppm: See Table 8.
Reference Example 24

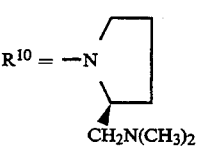

TABLE 2-continued

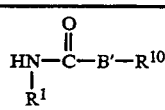

Properties: Colorless oily substance
$^1$H-NMR (CDCl$_3$) δ ppm: See Table 8.
Reference Example 25

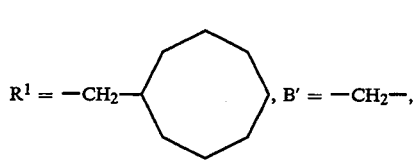
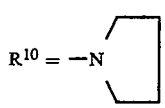

Properties: Colorless oily substance
$^1$H-NMR (CDCl$_3$) δ ppm: See Table 8.
Reference Example 26

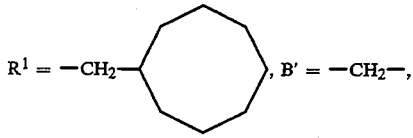
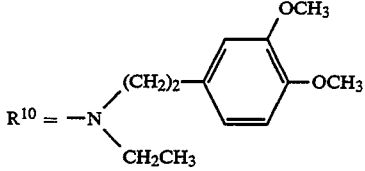

Properties: Colorless oily substance
$^1$H-NMR (CDCl$_3$) δ ppm: See Table 8.
Reference Example 27

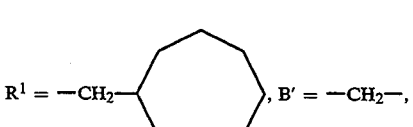
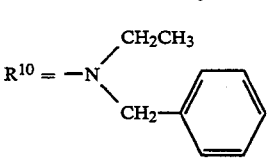

Properties: Colorless oily substance
$^1$H-NMR (CDCl$_3$) δ ppm: See Table 8.
Reference Example 28

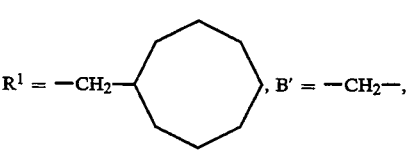
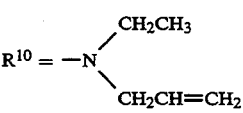

TABLE 2-continued $$\underset{\underset{R^1}{|}}{HN}-\overset{\overset{O}{\|}}{C}-B'-R^{10}$$

Properties: Light brown oily substance
¹H-NMR (CDCl₃) δ ppm: See Table 8.
Reference Example 29

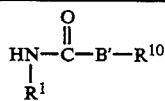

$R^1 = -CH_2-$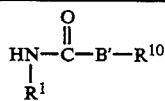, $B' = -CH_2-$, $R^{10} = -(CH_2)_2N(C_2H_5)_2$
Properties: Light brown oily substance
¹H-NMR (CDCl₃) δ ppm: See Table 8.
Reference Example 30

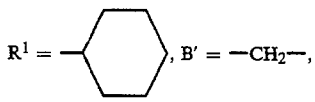

$R^1 = $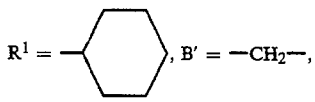, $B' = -CH_2-$,

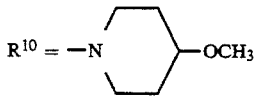

$R^{10} = -N$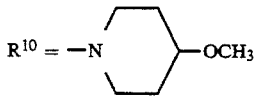$OCH_3$

Properties: Light brown oily substance
¹H-NMR (CDCl₃) δ ppm: See Table 8.
Reference Example 31

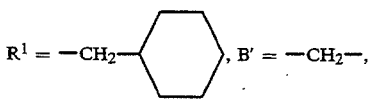

$R^1 = -CH_2-$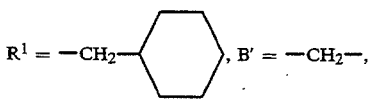, $B' = -CH_2-$,

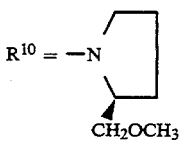

$R^{10} = -N$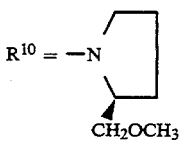
    $CH_2OCH_3$

Properties: Light brown oily substance
¹H-NMR (CDCl₃) δ ppm: See Table 1.

TABLE 3

$$\underset{\underset{R^1}{\diagdown}}{HN}\overset{CH_2-B'-R^{10}}{\diagup}$$

Reference Example 32

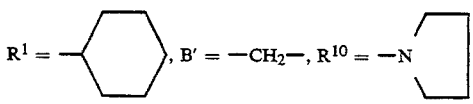

$R^1 = $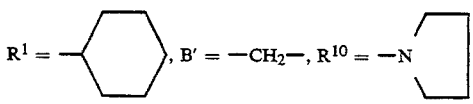, $B' = -CH_2-$, $R^{10} = -N$

Properties: Colorless oily substance
¹H-NMR (CDCl₃) δ ppm: See Table 8.
Reference Example 33

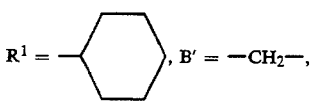

$R^1 = $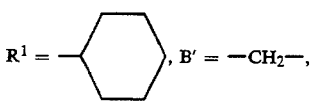, $B' = -CH_2-$,

TABLE 3-continued $$\underset{\underset{R^1}{\diagdown}}{HN}\overset{CH_2-B'-R^{10}}{\diagup}$$

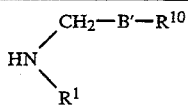

$R^{10} = -N$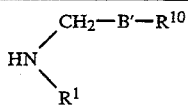$OCH_3$

Properties: Colorless oily substance
¹H-NMR (CDCl₃) δ ppm: See Table 8.
Reference Example 34

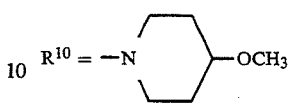

$R^1 = -CH_2-$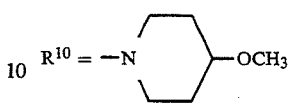, $B' = -CH_2-$,

$R^{10} = -N$$N-(CH_2)_2OH$

Properties: Light brown oily substance
¹H-NMR (CDCl₃) δ ppm: See Table 8.
Reference Example 35

$R^1 = -CH_2-$, $B' = -CH_2-$,

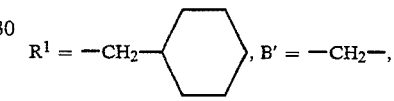

$R^{10} = -N$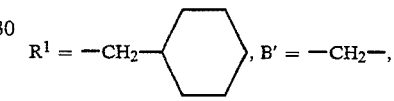

Properties: Colorless oily substance
¹H-NMR (CDCl₃) δ ppm: See Table 8.
Reference Example 36

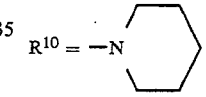

$R^1 = -CH_2-$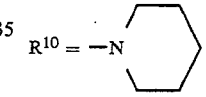, $B' = -CH_2-$,

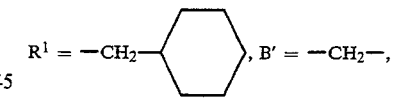

$R^{10} = -N$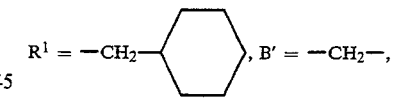$S$

Properties: Colorless oily substance
¹H-NMR (CDCl₃) δ ppm: See Table 8.
Reference Example 37

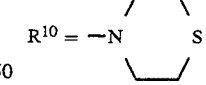

$R^1 = -CH_2-$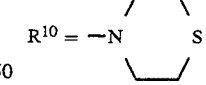, $B' = -CH_2-$,

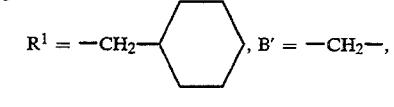

$R^{10} = -N$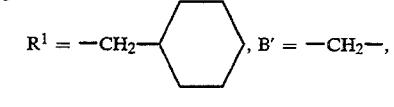
    $CH_2OH$

Properties: Colorless oily substance
¹H-NMR (CDCl₃) δ ppm: See Table 8.
Reference Example 38

TABLE 3-continued

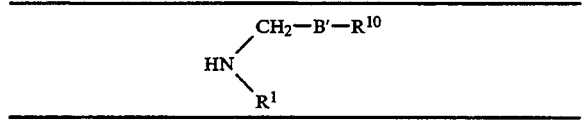

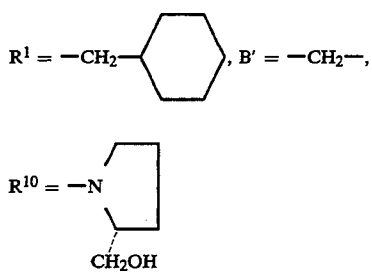

Properties: Colorless oily substance
$^1$H-NMR (CDCl$_3$) δ ppm: See Table 8.
Reference Example 39

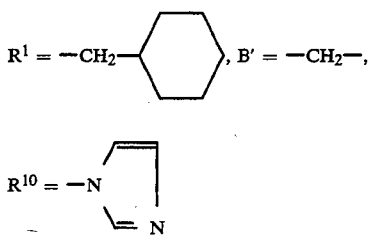

Properties: Light yellow oily substance
$^1$H-NMR (CDCl$_3$) δ ppm: See Table 8.
Reference Example 40

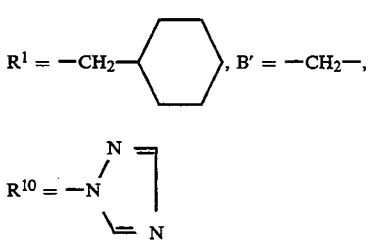

Properties: Colorless oily substance
Boiling point: 135–141° C./1 mmHg
Reference Example 41

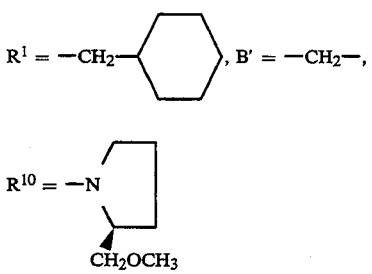

Properties: Colorless oily substance
$^1$H-NMR (CDCl$_3$) δ ppm: See Table 8.
Reference Example 42

TABLE 3-continued

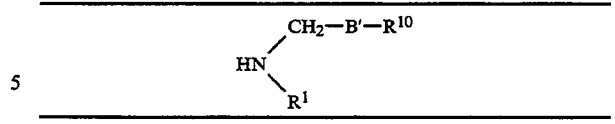

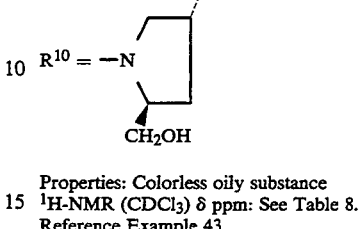

Properties: Colorless oily substance
$^1$H-NMR (CDCl$_3$) δ ppm: See Table 8.
Reference Example 43

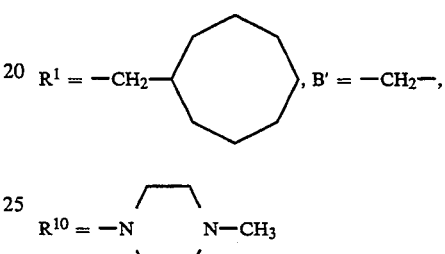

Properties: Colorless oily substance
Boiling point: 180° C./0.35 mmHg
Reference Example 44

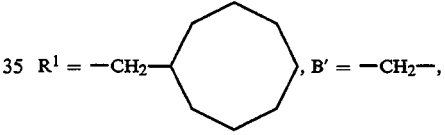

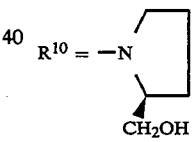

Properties: Colorless oily substance
$^1$H-NMR (CDCl$_3$) δ ppm: See Table 8.
Reference Example 45

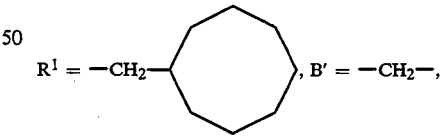

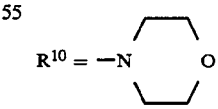

Properties: Colorless oily substance
$^1$H-NMR (CDCl$_3$) δ ppm: See Table 8.
Reference Example 46

TABLE 3-continued

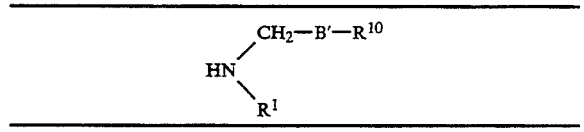

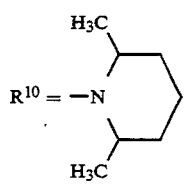

Properties: Colorless oily substance
$^1$H-NMR (CDCl$_3$) δ ppm: See Table 8.
Reference Example 47

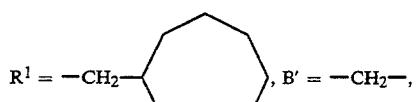

Properties: Colorless oily substance
$^1$H-NMR (CDCl$_3$) δ ppm: See Table 8.
Reference Example 48

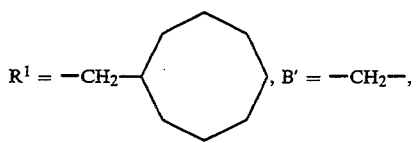

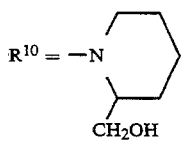

Properties: Colorless oily substance
$^1$H-NMR (CDCl$_3$) δ ppm: See Table 8.
Reference Example 49

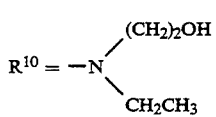

Properties: Colorless oily substance
$^1$H-NMR (CDCl$_3$) δ ppm: See Table 8.
Reference Example 50

TABLE 3-continued

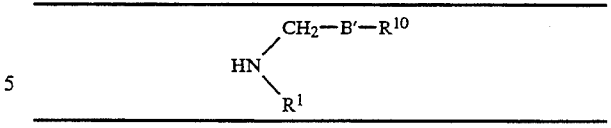

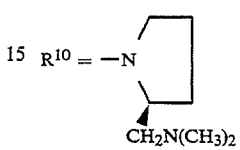

Properties: Colorless oily substance
$^1$H-NMR (CDCl$_3$) δ ppm: See Table 8.
Reference Example 51

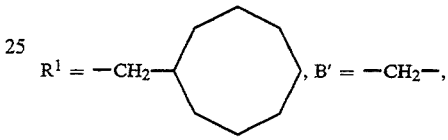

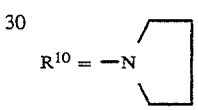

Properties: Colorless oily substance
Boiling point: 134° C./0.3 mmHg
Reference Example 52

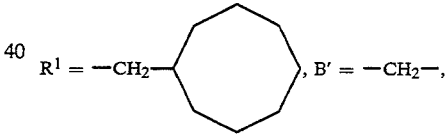

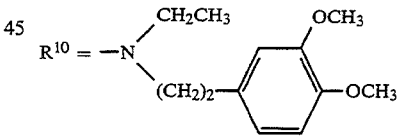

Properties: Colorless oily substance
$^1$H-NMR (CDCl$_3$) δ ppm: See Table 8.
Reference Example 53

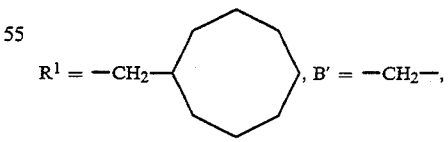

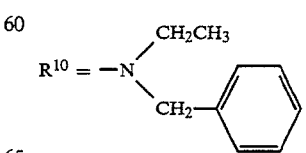

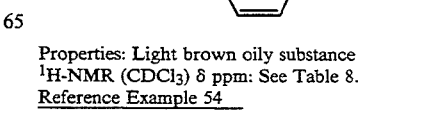

Properties: Light brown oily substance
$^1$H-NMR (CDCl$_3$) δ ppm: See Table 8.
Reference Example 54

TABLE 3-continued

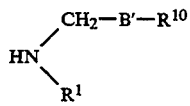

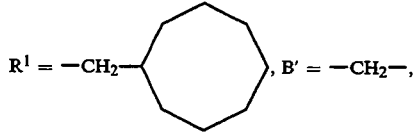

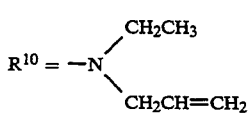

Properties: Colorless oily substance
$^1$H-NMR (CDCl$_3$) δ ppm: See Table 8.
Reference Example 55

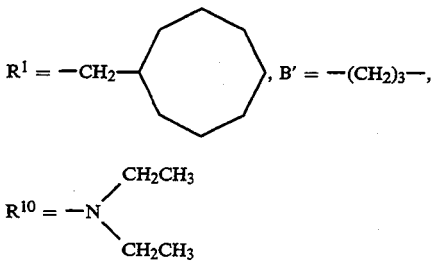

Properties: Colorless oily substance
Boiling point: 135–145° C./2 mmHg
Reference Example 56

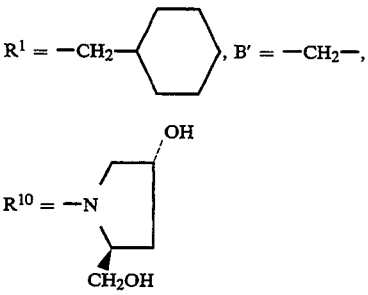

Properties: Colorless oily substance
$^1$H-NMR (CDCl$_3$) δ ppm: See Table 8.

TABLE 4

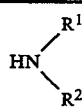

Reference Example 58

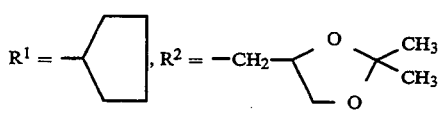

Properties: Colorless oily substance
Boiling point: 90° C./0.1 mmHg
Reference Example 59

TABLE 4-continued

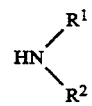

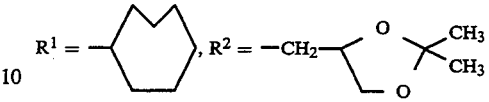

Properties: Colorless oily substance
Boiling point: 120° C./1 mmHg
Reference Example 60

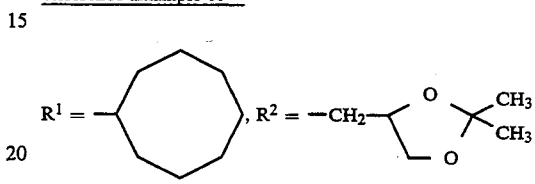

Properties: Colorless oily substance
Boiling point: 120° C./0.1 mmHg
Reference Example 61

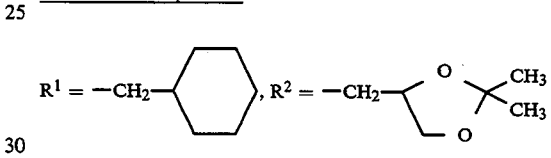

Properties: Colorless oily substance
Boiling point: 120° C./0.3 mmHg
Reference Example 62

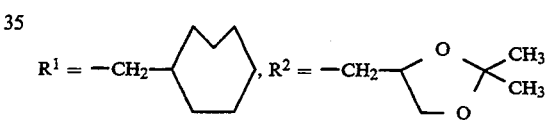

Properties: Colorless oily substance
Boiling point: 125° C./0.5 mmHg
Reference Example 63

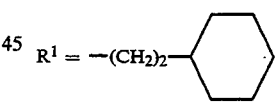

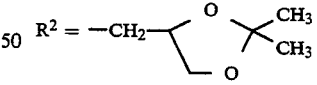

Properties: Colorless oily substance
Boiling point: 125° C./0.25 mmHg
Reference Example 64

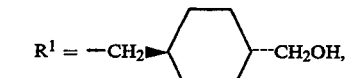

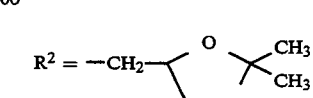

Properties: Colorless oily substance
$^1$H-NMR (CDCl$_3$) δ ppm: See Table 8.

TABLE 5

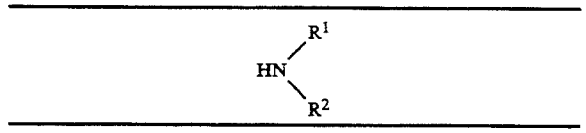

Reference Example 67

$R^1 = $ 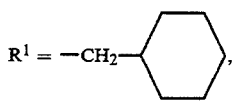, $R^2 = -(CH_2)_2N(C_2H_5)_2$
Properties: Colorless acicular crystals
$^1$H-NMR (CDCl$_3$) δ ppm: See Table 8.
Reference Example 68

$R^1 = $ 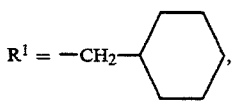, $R^2 = $ 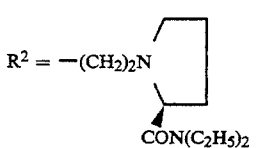

Properties: Colorless oily substance
$^1$H-NMR (CDCl$_3$) δ ppm: See Table 8.
Reference Example 69

$R^1 = $ 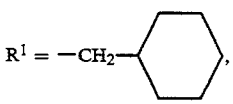, $R^2 = $ 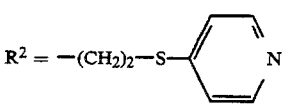

Properties: Colorless oily substance
$^1$H-NMR (CDCl$_3$) δ ppm: See Table 8.
Reference Example 70

$R^1 = $ 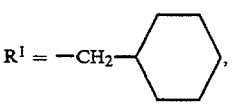, $R^2 = $ 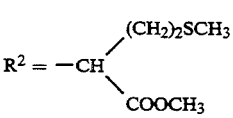

Properties: Colorless oily substance
$^1$H-NMR (CDCl$_3$) δ ppm: See Table 8.
Reference Example 71

$R^1 = $ 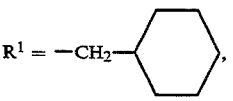, $R^2 = -(CH_2)_2SH$
Properties: Colorless oily substance
$^1$H-NMR (CDCl$_3$) δ ppm: See Table 8.
Reference Example 72

TABLE 5-continued

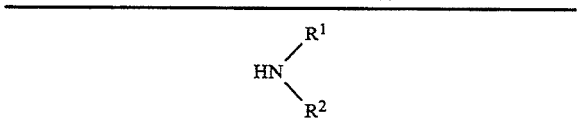

$R^1 = $ 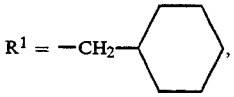, $R^2 = $ 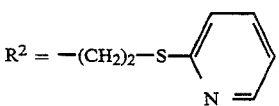

Properties: Light yellow oily substance
$^1$H-NMR (CDCl$_3$) δ ppm: See Table 8.
Reference Example 73

$R^1 = $ 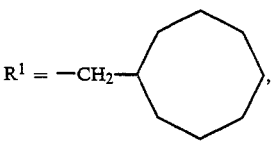, $R^2 = -(CH_2)_3N(C_2H_5)_2$
Properties: Colorless oily substance
Boiling point: 130–140° C./2 mmHg
Reference Example 74

$R^1 = $ 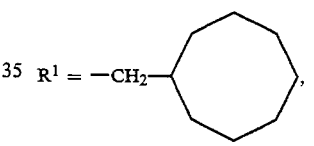, $R^2 = -(CH_2)_2N(CH_3)_2$
Properties: Colorless oily substance
Boiling point: 100–105° C./2 mmHg
Reference Example 75

$R^1 = $ 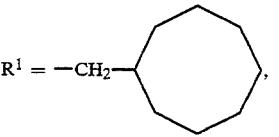, $R^2 = -(CH_2)_2NHCOCH_3$
Properties: Colorless oily substance
$^1$H-NMR (CDCl$_3$) δ ppm: See Table 8.
Reference Example 76

$R^1 = $ 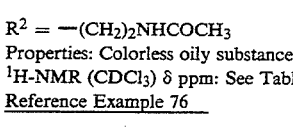, $R^2 = -\overset{\overset{\displaystyle CH_3}{|}}{CH}CON(C_2H_5)_2$ (S type)

Properties: Colorless oily substance
$^1$H-NMR (CDCl$_3$) ppm: See Table 8.
Reference Example 77

TABLE 5-continued

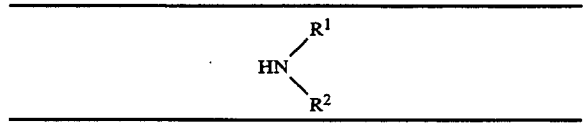

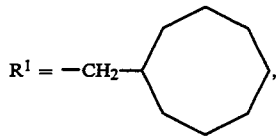

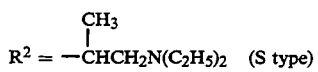

Properties: Colorless oily substance
Boiling point: 130° C./0.3 mmHg
Reference Example 78

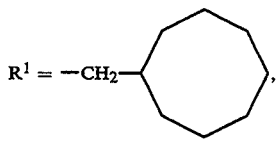

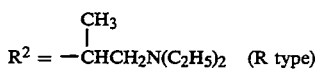

Properties: Colorless oily substance
Boiling point: 122–127° C./0.5 mmHg
Reference Example 79

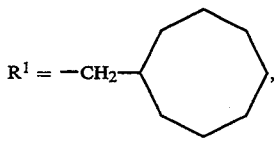

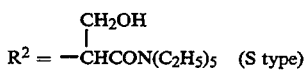

Properties: Colorless oily substance
$^1$H-NMR (CDCl$_3$) δ ppm: See Table 8.
Reference Example 80

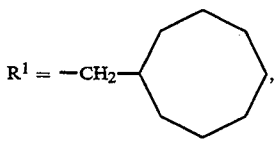

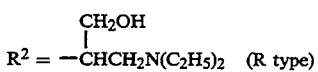

Properties: Colorless oily substance
$^1$H-NMR (CDCl$_3$) δ ppm: See Table 8.
Reference Example 81

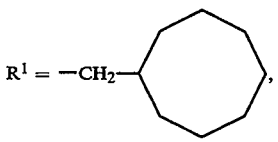

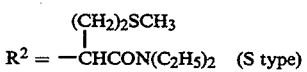

TABLE 5-continued

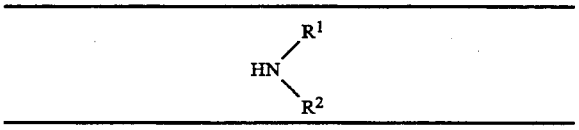

Properties: Colorless oily substance
$^1$H-NMR (CDCl$_3$) δ ppm: See Table 8.
Reference Example 82

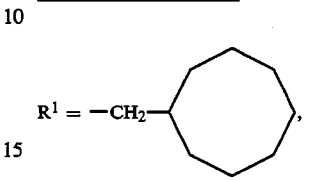

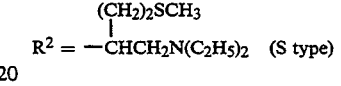

Properties: Colorless oily substance
$^1$H-NMR (CDCl$_3$) δ ppm: See Table 8.
Reference Example 83

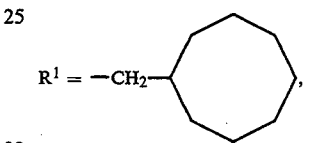

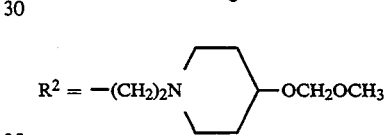

Properties: Colorless oily substance
Boiling point: 190° C./4 mmHg
Reference Example 84

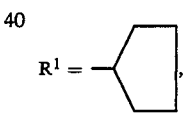

R$^2$ = —(CH$_2$)$_2$N(C$_2$H$_5$)$_2$
Properties: Colorless oily substance
Boiling point: 74° C./0.4 mmHg
Reference Example 85

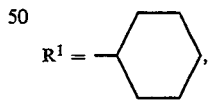

R$^2$ = —(CH$_2$)$_2$N(C$_2$H$_5$)$_2$
Properties: Colorless oily substance
Boiling point: 83–85° C./0.3 mmHg
Reference Example 86

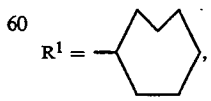

R$^2$ = —(CH$_2$)$_2$N(C$_2$H$_5$)$_2$
Properties: Colorless oily substance
Boiling point: 93° C./0.35 mmHg
Reference Example 87

TABLE 5-continued

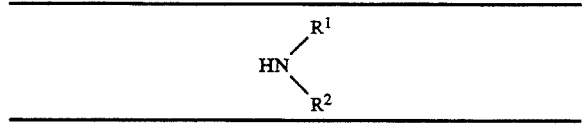

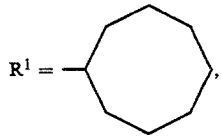

R² = —(CH₂)₂N(C₂H₅)₂
Properties: Colorless oily substance
Boiling point: 94–95° C./0.35 mmHg
Reference Example 88

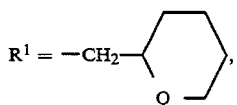

R² = —(CH₂)₂N(C₂H₅)₂
Properties: Colorless oily substance
Boiling point: 155–160° C./24 mmHg
Reference Example 89

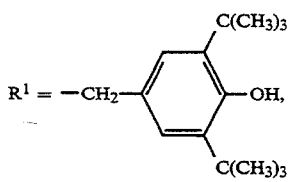

R² = —(CH₂)₂N(C₂H₅)₂
Properties: Colorless oily substance
¹H-NMR (CDCl₃) δ ppm: See Table 8.
Reference Example 90

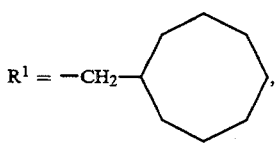

Properties: Colorless oily substance
¹H-NMR (CDCl₃) δ ppm: See Table 8.
Reference Example 91

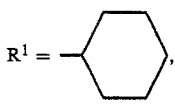

R² = —CH₂CH—CH₂—OH
         |
         OH

Properties: Colorless oily substance
Boiling point: 114–118° C./0.4 mmHg
Reference Example 92

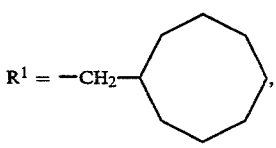

TABLE 5-continued

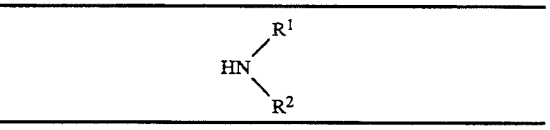

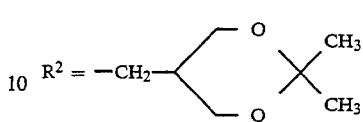

Properties: Colorless oily substance
Boiling point: 120° C./0.1 mmHg
Reference Example 93

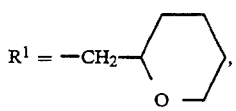

R² = —CH₂CH—CH₂OH
         |
         OH

Properties: Colorless oily substance
Boiling point: 155–165° C./0.7 mmHg
Reference Example 94

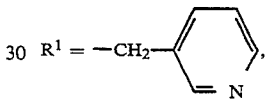

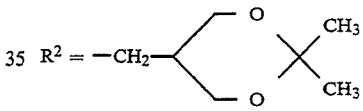

Properties: Light yellow oily substance
¹H-NMR (CDCl₃) δ ppm: See Table 8.
Reference Example 95

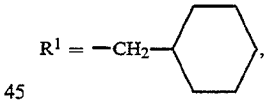

R² = —CH₂CH—CH₂OCH₃
         |
         OCH₃

Properties: Colorless oily substance
Boiling point: 105° C./0.1 mmHg
Reference Example 96

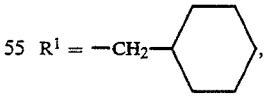

CH₂OH
        |
R² = —CH—COOCH₃

Properties: Colorless oily substance
¹H-NMR (CDCl₃) δ ppm: See Table 8.
Reference Example 97

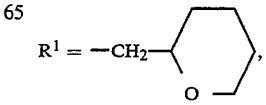,  R² = —(CH₂)₃OH

TABLE 5-continued

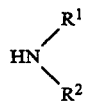

Properties: Colorless oily substance
Boiling point: 150–155° C./11 mmHg
Reference Example 98

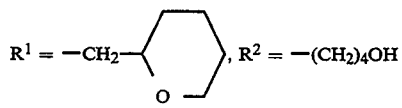

Properties: Colorless oily substance
Boiling point: 135° C./3 mmHg
Reference Example 99

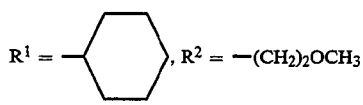

Properties: Colorless oily substance
Boiling point: 95–98° C./22 mmHg
Reference Example 100

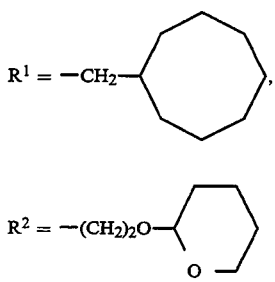

Properties: Colorless oily substance
$^1$H-NMR (CDCl$_3$) δ ppm: See Table 8.
Reference Example 101

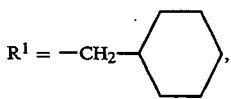

$R^2 = -(CH_2)_2OH$.
Properties: Colorless oily substance
Boiling point: 131–133° C./12 mmHg
Reference Example 102

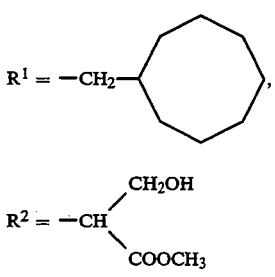

Properties: Colorless oily substance
$^1$H-NMR (CDCl$_3$) δ ppm: See Table 8.
Reference Example 103

TABLE 5-continued

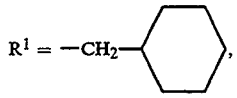

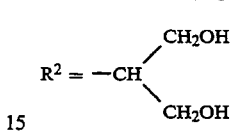

Properties: Colorless oily substance
$^1$H-NMR (CDCl$_3$) δ ppm: See Table 8.
Reference Example 104

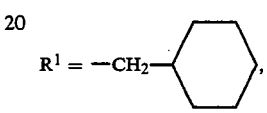

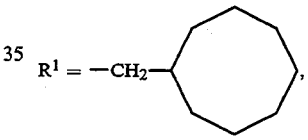

Properties: Colorless oily substance
$^1$H-NMR (CDCl$_3$) δ ppm: See Table 8.
Reference Example 105

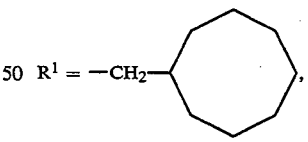

Properties: Colorless oily substance
$^1$H-NMR (CDCl$_3$) δ ppm: See Table 8.
Reference Example 106

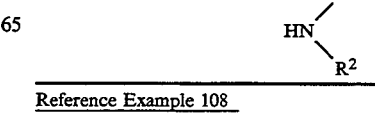

Properties: Colorless oily substance
$^1$H-NMR (CDCl$_3$) δ ppm: See Table 8.

TABLE 6

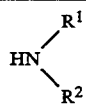

Reference Example 108

TABLE 6-continued

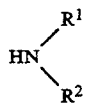

R¹ = 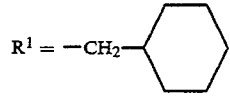

R² = —CH₂CHCH₂Cl
         |
         OH

Properties: Colorless oily substance
¹H-NMR (CDCl₃) δ ppm: See Table 8.
Reference Example 109

R¹ = 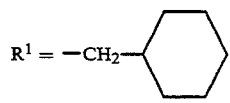

R² = —CH₂CHCH₂OCH₃
         |
         OH

Properties: Colorless oily substance
Boiling point: 130° C./3 mmHg
Reference Example 110

R¹ = 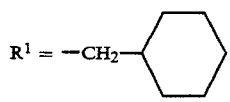

R² = —CH₂CH—CH₃
           |
           OH

Properties: Colorless oily substance
Boiling point: 105–115° C./8 mmHg
Reference Example 111

R¹ = 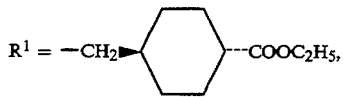

R² = —CH₂CHCH₃
         |
         OH

Properties: Colorless oily substance
¹H-NMR (CDCl₃) δ ppm: See Table 8.
Reference Example 112

R¹ = 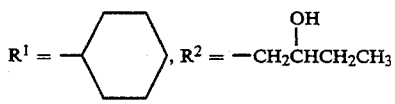, R² = —CH₂CHCH₂CH₃
                                     |
                                     OH Properties: Colorless oily substance
Boiling point: 122–125° C./12 mmHg

TABLE 7

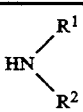

Reference Example 136

TABLE 7-continued

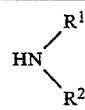

R¹ = 

R² = —CH₂COOCH₃
Properties: Colorless oily substance
¹H-NMR (CDCl₃) δ ppm: See Table 8.
Reference Example 137

R¹ = 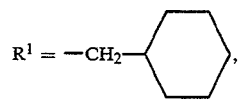,

R² = —(CH₂)₃OH
Properties: Colorless oily substance
Boiling point: 135–142° C./10 mmHg
Reference Example 138

R¹ = 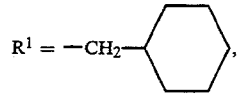,

R² = —(CH₂)₄OH
Properties: Colorless oily substance
Boiling point: 158–160° C./12 mmHg
Reference Example 139

R¹ = 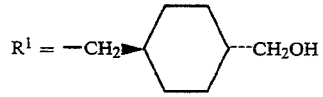

R² = —(CH₂)₂OH
Properties: Colorless oily substance
¹H-NMR (CDCl₃) δ ppm: See Table 8.

TABLE 8

| Reference Example No. | ¹H-NMR (CDCl₃) δ ppm |
|---|---|
| Reference Example 6 | 1.17–1.78 (15H, m), 2.12(2H, quintet, J=7Hz), 2.36(2H, t, J=7Hz), 3.10(2H, t, J=7Hz), 3.61(2H, t, J=6Hz), 5.56(1H, s) |
| Reference Example 7 | 1.10–1.98(14H, m), 2.50–2.40(4H, m), 3.12(2H, s), 3.80(1H, m), 7.02(1H, s), |
| | 1.12–2.10(14H, m), 2.29(2H, m), 2.76(2H, m), 2.96(2H, s), 3.68–3.40(2H, m), 7.11(1H, s) |
| Reference Example 8 | 1.12–2.19(14H, m), 2.29(2H, m), 2.76(2H, m), 2.96(2H, s), 3.68–3.87(2H, m), 7.11(1H, s) |
| Reference Example 9 | 0.85–1.88(11H, m), 2.47–2.74(10H, m), 3.01(2H, s), 3.12(2H, t, J=6Hz), 3.62(2H, t, J=6Hz), 7.20(1H, s) |
| Reference Example 10 | 0.88–1.88(17H, m), 2.33–2.60(4H, m), 3.12(2H, t, J=7Hz), 2.94(2H, s), 7.35(1H, s) |
| Reference Example 11 | 0.86–2.16(11H, m), 2.66–2.76(4H, m), 2.76–2.92(4H, m), 3.01(2H, s), 3.09–3.31(2H, m), 7.16(1H, s) |
| Reference Example 12 | 0.80–2.26(15H, m), 2.38–2.53(1H, m), 2.70–2.87(1H, m), 3.00–3.30(4H, m), 3.44(1H, d, J=17Hz), 3.51(1H, dd, J=10Hz, 4Hz), 3.59(1H, dd, J=10Hz, 4Hz), |

TABLE 8-continued

| Reference Example No. | $^1$H-NMR (CDCl$_3$) δ ppm |
|---|---|
| | 7.13(1H, s) |
| Reference Example 13 | 0.84–2.20(15H, m), 2.38–2.53(1H, m), 2.70–2.87(1H, m), 3.00–3.30(4H, m), 3.44(1H, d, J=17Hz), 3.51(1H, dd, J=10Hz, 4Hz), 3.59(1H, dd, J=10Hz, 4Hz), 7.09(1H, s) |
| Reference Example 14 | 0.73–1.83(11H, m), 3.08(2H, t, J=7Hz), 4.66(2H, s), 6.97(1H, s), 7.18(1H, s), 7.53(1H, s), 5.50(1H, s) |
| Reference Example 15 | 0.74–1.80(11H, m), 3.11(2H, t, J=6Hz), 4.86(2H, s), 8.06(1H, s), 8.19(1H, s), 6.31(1H, s) |
| Reference Example 16 | 0.83–1.84(11H, m), 1.98(2H, dd, J=8Hz, 5Hz), 2.57(1H, dd, J=10Hz, 6Hz), 2.95–3.29(4H, m), 3.36(3H, s), 3.39–3.57(3H, m), 3.63(1H, dd, J=11Hz, 4Hz), 7.06(1H, s) |
| Reference Example 17 | 1.21–1.87(15H, m), 2.36–2.68(8H, m), 2.30(3H, s), 3.01(2H, s), 3.11(2H, t, J=6Hz), 7.24(1H, s) |
| Reference Example 18 | 1.21–2.08(19H, m), 2.42(1H, m), 2.77(1H, m), 2.98–3.26(3H, m), 3.08(1H, d, J=17Hz), 3.45(1H, d, J=17Hz), 3.51(1H, dd, J=11Hz, 4Hz), 3.59(1H, dd, J=11Hz, 4Hz), 7.09(1H, s) |
| Reference Example 19 | 1.20–1.85(15H, m), 2.48–2.60(2H, m), 3.01(2H, s), 3.05–3.20(2H, m), 3.05–3.20(2H, m), 3.63–3.79(4H, m), 7.19(1H, s) |
| Reference Example 20 | 1.00(3H, s), 1.02(3H, s), 1.10–1.80(21H, m), 2.45(2H, m), 3.07(2H, s), 2.93–3.17(2H, m), 7.63(1H, s) |
| Reference Example 21 | 1.20–2.34(18H, m), 2.40–2.57(1H, m), 2.63–2.81(2H, m), 2.87–3.04(1H, m), 3.11(2H, t, J=7Hz), 3.17(2H, s), 4.41(1H, m), 7.13(1H, s) |
| Reference Example 22 | 1.12–1.95(21H, m), 2.30–2.53(2H, m), 2.79–2.90(1H, m), 2.94(1H, d, J=17Hz), 3.02–3.27(2H, m), 3.47(1H, d, J=17Hz), 3.60(1H, dd, J=11Hz, 5Hz), 3.67(1H, dd, J=11Hz, 5Hz), 7.36(1H, s) |
| Reference Example 23 | 1.06(3H, t, J=9Hz), 1.17–2.08(15H, m), 2.62(2H, q, J=9Hz), 2.68(2H, t, J=7Hz), 3.13(2H, s), 3.11(2H, t, J=8Hz), 3.67(2H, t, J=7Hz), 7.36(1H, s) |
| Reference Example 24 | 1.18–1.88(18H, m), 1.91–2.09(1H, m), 2.21(6H, s), 2.09–2.44(2H, m), 2.70(1H, m) |
| Reference Exampe 25 | 1.18–2.00(19H, m), 2.48–2.75(14H, m), 3.11(2H, t, J=7Hz), 3.14(2H, s), 7.20(1H, s) |
| Reference Example 26 | 0.96–1.82(15H, m), 1.05(3H, t, J=7Hz), 2.54–2.88(6H, m), 2.88–3.23(2H, m), 3.07(2H, s), 3.87(6H, s), 6.67–6.93(3H, m), 7.09(1H, s) |
| Reference Example 27 | 1.09(3H, t, J=7Hz), 1.18–1.81(15H, m), 2.57(2H, q, J=7Hz), 2.97–3.21(2H, m), 3.07(2H, s), 3.62(3H, s), 6.61(1H, s), 7.17–7.50(5H, m) |
| Reference Example 28 | 1.05(3H, t, J=7Hz), 1.17–1.94(15H, m), 2.56(2H, q, J=7Hz), 3.05(2H, s), 2.96–3.18(4H, m), 5.10–5.30(2H, m), 5.80(1H, m), 7.40(1H, s) |
| Reference Example 29 | 1.02(6H, t, J=7Hz), 1.17–1.94(17H, m), 2.25(2H, t, J=7Hz), 2.40–2.64(6H, m), 3.07(2H, t, J=7Hz), 6.50(1H, s) |
| Reference Example 30 | 1.10–2.00(14H, m), 2.28(2H, m), 2.67–2.80(2H, m), 2.96(2H, s), 3.23(1H, m), 3.34(3H, s), 3.79(1H, s) |
| Reference Example 31 | 0.80–2.00(15H, m), 2.41(1H, m), 2.79(1H, m), 3.03–3.18(4H, m), 3.28–3.34(2H, m), 3.32(3H, s), 3.47(1H, d, J=17Hz), 7.44(1H, s) |
| Reference Example 32 | 0.97–2.13(16H, m), 2.33–2.56(4H, m), 2.58(2H, t, J=6Hz), 2.75(2H, t, J=6Hz) |
| Reference Example 33 | 1.03–2.03(12H, m), 2.16(2H, m), 2.66–2.99(5H, m), 2.77(2H, t, J=6Hz), 2.52(2H, t, J=6Hz), 2.42–2.62(1H, m), 3.22(1H, m), 3.33(3H, s) |
| Reference Example 34 | 0.78–1.82(11H, m), 2.33–2.62(14H, m), 2.68(2H, t, J=7Hz) |
| Reference Example 35 | 0.72–2.20(20H, m), 2.23–2.57(4H, m), 2.67(2H, t, J=6Hz) |
| Reference Example 36 | 0.74–1.39(5H, m), 1.47(1H, m), 1.60–1.91(5H, m), 1.91–2.34(2H, m), 2.43(2H, d, J=7Hz), 2.51(2H, t, J=6Hz), 2.59–2.83(8H, m) |
| Reference Example 37 | 0.80–2.00(16H, m), 2.20–2.80(8H, m), 2.83–2.93(1H, m), 3.10–3.22(1H, m), 3.38(1H, dd, J=5Hz, 11Hz), 3.57(1H, dd, J=4Hz, 11Hz) |
| Reference Example 38 | 0.79–2.09(16H, m), 2.27–2.85(7H, m), 2.85–3.02(1H, m), 3.15(1H, m), 3.37(1H, dd, J=11Hz, 5Hz), 3.59(1H, dd, J=11Hz, 5Hz) |
| Reference Example 39 | 0.79–1.00(2H, m), 1.10–1.80(10H, m), 2.43(2H, d, J=7Hz) |
| Reference Example 41 | 0.80–2.12(16H, m), 2.10–2.29(1H, m), 2.38–2.50(3H, m), 2.53–2.28(3H, m), 2.90–3.17(2H, m), 3.27(1H, d, J=9Hz, 5Hz), 3.35(3H, s), 3.40(1H, dd, J=9Hz, 5Hz) |
| Reference Example 42 | 0.76–2.02(14H, m), 2.50–3.56(11H, m), 3.36(3H, s), 3.62–3.83(2H, m), 4.21(1H, m), 4.63(2H, s) |
| Reference Example 44 | 1.20–2.00(20H, m), 2.25–2.58(5H, m), 2.58–2.80(3H, m), 2.87–2.95(1H, m), 3.05–3.25(1H, m), 3.37(1H, dd, J=5Hz, 10Hz), 3.59(1H, dd, J=5Hz, 10Hz) |
| Reference Example 45 | 1.15–1.95(15H, m), 2.23(1H, b), 2.36–2.60(8H, m), 2.71(2H, t, J=7Hz), 3.71(4H, t, J=7Hz) |
| Reference Example 46 | 1.14(6H, d, J=7Hz), 1.15–2.05(22H, m), 2.30–2.08(4H, m), 2.10–2.36(4H, m) |
| Reference Example 47 | 1.15–1.82(17H, m), 1.94(2H, b), 2.10–2.39(2H, m), 2.45(2H, d, J=7Hz), 2.56–2.71(2H, m), 2.71–2.80(3H, m), 2.85–3.00(1H, m), 4.26–4.40(1H, m) |
| Reference Example 48 | 1.20–2.20(22H, m), 2.25–2.65(3H, m), 2.65–2.85(1H, m), 2.85–3.15(5H, m), 3.42(1H, dd, J=4Hz, 12Hz), 3.69(1H, t, J=6Hz), 3.84(1H, dd, J=6Hz, 12Hz) |
| Reference Example 49 | 1.04(3H, t, J=7Hz), 1.21–1.85(16H, m), 2.47(2H, q, J=7Hz), 2.50–2.90(9H, m), 3.58(2H, t, J=7Hz) |
| Reference Example 50 | 1.15–2.08(20H, m), 2.10–2.22(1H, m), 2.24(6H, s), 2.30–2.60(6H, m), 2.70(2H, t, J=7Hz), 2.95–3.17(2H, m) |
| Reference Example 52 | 1.05(3H, t, J=7Hz), 1.17–1.73(16H, m), 2.42(2H, d, J=7Hz), 2.57–2.79(10H, m), 3.85, 3.88(3H, singlet, respectively), 6.69–6.82(3H, m) |
| Reference Example 53 | 1.04(3H, t, J=7Hz), 1.18–1.80(16H, m), 2.34(2H, d, J=7Hz), 2.53(2H, q, J=7Hz), 2.60–2.67(4H, m), 3.57(2H, s), 7.18–7.40(5H, m) |
| Reference Example 54 | 1.02(3H, t, J=7Hz), 1.20–1.80(15H, m), 2.09(1H, b), 2.42(2H, d, J=7Hz), 2.49–2.69(6H, m), 3.08–3.11(2H, m), 5.09–5.21(2H, m), 5.76–5.92(1H, m) |
| Reference Example 56 | 0.70–1.96(14H, m), 2.30–2.57(4H, m), 2.57–2.80(2H, m), 2.83–3.15(2H, m), 3.32–3.46(2H, m), 3.62(1H, dd, J=13Hz, 3Hz), 4.34(1H, m) |
| Reference Example 64 | 0.83–1.08(4H, m), 1.36(3H, s), 1.42(3H, s), 1.48–1.55(2H, m), 1.74–1.93(4H, m), 2.49(2H, d, J=7Hz), 2.65–2.78(2H, m), 3.45(2H, d, J=6Hz), 3.66(1H, dd, J=8Hz, 7Hz), 4.05(1H, dd, J=8Hz, 6Hz), 4.19–4.30(1H, m) |
| Reference | 1.12(6H, t, J=7Hz), 0.90–1.50(5H, m), |

TABLE 8-continued

| Reference Example No. | $^1$H-NMR (CDCl$_3$) δ ppm |
|---|---|
| Example 67 | 1.60–2.00(7H, m), 2.67–2.77(6H, m), 2.94(2H, t, J=7Hz), 3.04(2H, t, J=7Hz) |
| Reference Example 68 | 1.21(3H, t, J=7Hz), 1.32(3H, t, J=7Hz), 0.85–1.45(16H, m), 2.16–2.35(1H, m), 2.41–2.85(4H, m), 2.48–3.08(1H, m), 3.12–3.53(7H, m) |
| Reference Example 69 | 1.75–1.90(12H, m), 2.46(2H, d, J=7Hz), 2.93(2H, t, J=7Hz), 3.14(2H, t, J=7Hz), 7.14(2H, dd, J=4.6Hz, 1.6Hz), 8.39(2H, dd, J=4.6Hz, 1.6Hz) |
| Reference Example 70 | 0.75–2.05(14H, m), 2.10(3H, s), 2.23–2.46(2H, m), 2.60(2H, t, J=7Hz), 3.31–3.38(1H, m), 3.73(3H, s) |
| Reference Example 71 | 0.80–2.10(13H, m), 2.40–3.10(6H, m) |
| Reference Example 72 | 0.75–1.92(12H, m), 2.57(2H, d, J=7Hz), 3.05(2H, t, J=6Hz), 3.38(2H, t, J=6Hz), 6.92–7.09(1H, m), 7.22(1H, dd, J=7Hz, 1Hz), 7.48(1H, dt, J=2Hz, 7Hz), 8.35–8.46(1H, m) |
| Reference Example 75 | 1.10–1.70(16H, m), 1.99(3H, s), 2.41(2H, d, J=7Hz), 2.72(2H, t, J=6Hz), 3.31(2H, q, J=6Hz), 6.09(1H, b) |
| Reference Example 76 | 1.13(3H, t, J=7Hz), 1.18–1.80(21H, m), 1.99(1H, b), 2.18–2.32(2H, m), 3.20–3.60(5H, m) |
| Reference Example 79 | 1.13(3H, t, J=7Hz), 1.22(3H, t, J=7Hz), 1.08–1.80(15H, m), 2.22(1H, dd, J=13Hz, 8Hz), 2.43(1H, dd, J=13Hz, 7Hz), 2.04–2.38(1H, br), 3.22–3.58(6H, m), 3.63(1H, dd, J=10Hz, 4Hz) |
| Reference Example 80 | 1.03(6H, t, J=7Hz), 1.15–1.90(16H, m), 2.28–2.67(8H, m), 2.73(1H, m), 3.52(1H, dd, J=11Hz, 2Hz), 3.59(1H, dd, J=11Hz, 6Hz) |
| Reference Example 81 | 1.13(3H, t, J=7Hz), 1.22(3H, t, J=7Hz), 1.35–1.80(18H, m), 2.11(3H, s), 2.11–2.38(2H, m), 2.60–2.80(2H, m), 3.15–3.65(5H, m) |
| Reference Example 82 | 0.99(6H, t, J=7Hz), 1.15–1.90(18H, m), 2.11(3H, s), 2.20–2.70(11H, m) |
| Reference Example 89 | 1.00(6H, t, J=7Hz), 1.44(18H, s), 1.80(1H, b), 2.47–2.61(6H, m), 2.72(2H, t, J=7Hz), 3.71(2H, s), 5.12(1H, s), 7.10(2H, s) |
| Reference Example 90 | 1.12(6H, t, J=7Hz), 1.15–1.33(3H, m), 1.33–1.82(15H, m), 2.06(1H, s), 2.13–2.36(2H, m), 3.17–3.63(5H, m) |
| Reference Example 94 | 1.35(3H, s), 1.41(3H, s), 2.68–2.77(2H, m), 3.69(1H, dd, J=8Hz, 7Hz), 3.85(2H, s), 4.04(1H, dd, J=8Hz, 6Hz), 4.26(1H, m), 7.26(1H, dd, J=8Hz, 5Hz), 7.69(1H, m), 8.50(1H, m), 8.56(1H, m) |
| Reference Example 96 | 0.82–1.85(11H, m), 2.32(1H, dd, J=11Hz, 7Hz), 2.54(1H, dd, J=11Hz, 7Hz), 3.35(1H, dd, J=7Hz, 5Hz), 3.57(1H, dd, J=11Hz, 7Hz), 3.75(1H, t), 3.76(1H, dd, J=7Hz, 5Hz) |
| Reference Example 100 | 1.18–2.13(21H, m), 2.46(2H, d, J=7Hz), 2.79(2H, t, J=5Hz), 3.44–3.59(2H, m), 3.88–3.95(2H, m), 4.60(1H, dd, J=4Hz, 3Hz) |
| Reference Example 102 | 1.20–1.84(15H, m), 2.10–2.38(3H, m), 2.54(1H, dd, J=11Hz, 6Hz), 3.35(1H, dd, J=7Hz, 5Hz), 3.55(1H, dd, J=11Hz, 7Hz), 3.70–3.83(1H, m), 3.75(3H, s) |
| Reference Example 103 | 0.81–1.87(12H, m), 2.53(2H, d, J=7Hz), 2.72(1H, m), 2.90(2H, s), 3.55–3.80(4H, m) |
| Reference Example 104 | 0.80–1.96(12H, m), 1.41(1H, s), 1.43(1H, s), 2.44(2H, d, J=7Hz), 2.62(1H, m), 3.68(1H, dd, J=12Hz, 6Hz), 3.97(1H, dd, J=12Hz, 4Hz) |
| Reference | 1.19–1.85(15H, m), 2.48(2H, d, J=5Hz), |

TABLE 8-continued

| Reference Example No. | $^1$H-NMR (CDCl$_3$) δ ppm |
|---|---|
| Example 105 | 2.49(3H, s), 2.74(1H, m), 3.55(2H, dd, J=11Hz, 5Hz), 3.72(2H, dd, J=11Hz, 5Hz) |
| Reference Example 106 | 1.11–1.83(15H, m), 1.42(3H, s), 1.43(3H, s), 2.42(2H, d, J=7Hz), 2.62(1H, m), 3.68(2H, dd, J=12Hz, 6Hz), 3.97(2H, dd, J=12Hz, 4Hz) |
| Reference Example 108 | 0.75–1.09(2H, m), 1.09–1.37(3H, m), 1.47(1H, m), 1.61–1.92(5H, m), 2.48(2H, m), 2.68(1H, dd, J=12Hz, 8Hz), 2.80(1H, dd, J=12Hz, 4Hz), 3.16(2H, s), 3.55(2H, d, J=6Hz) |
| Reference Example 111 | 0.87–1.10(2H, m), 1.15(3H, d, J=6Hz), 1.25(3H, t, J=7Hz), 1.32–1.57(3H, m), 1.82–2.06(4H, m), 2.22(1H, tt, J=12Hz, 4Hz), 2.32–2.43(2H, m), 2.47(1H, dd, J=14Hz, 7Hz), 2.69(1H, dd, J=12Hz, 3Hz), 3.76(1H, m), 4.11(2H, q, J=7Hz) |
| Reference Example 136 | 0.85–1.00(4H, m), 1.33–1.54(2H, m), 1.61(1H, s), 1.72–1.95(4H, m), 2.45(2H, d, J=7Hz), 3.40(2H, s), 3.45(2H, d, J=6Hz), 3.73(3H, s) |
| Reference Example 139 | 0.74–1.17(4H, m), 1.22–1.61(2H, m), 1.61–1.99(5H, m), 2.47(2H, d, J=8Hz), 2.75(2H, t, J=7Hz), 3.44(2H, d, J=8Hz), 3.64(2H, t, J=7Hz) |

Example 1

2.00 Grams of 6-(4-carboxybutoxy)carbostyril is suspended in 60 ml of chloroform. Thereto is added 1.40 g of DBu. The mixture is stirred for 30 minutes at room temperature. 1.05 g of isobutyl chloroformate is added with ice cooling. Then, there is dropwise added at room temperature 1.61 g of N-(cyclohexylmethyl)-N-[2-(1-pyrrolidinyl)ethyl]amine. The mixture is stirred for 3 hours at room temperature. Then, a 0.5N aqueous sodium hydroxide solution is added, and the mixture is stirred for 10 minutes. Extraction with chloroform is effected. The extract is washed with water and dried with anhydrous magnesium sulfate. The solvent is removed by evaporation. The resulting residue is purified by a silica gel column chromatography (chloroform-:methanol=20:1) and recrystallized from diethyl ether to obtain 1.00 g of 6-[4-{N-cyclohexylmethyl-N-[2-(1-pyrrolidinyl)ethyl]aminocarbonyl}butoxy]carbostyril.

Properties: Colorless powdery crystals
Melting point: 105°–106° C.

Examples 2–121

Using appropriate starting materials and in the same procedure as in Example 1, there are obtained compounds shown in Table 9 given later.

In Table 9 are also shown the properties (crystal form and solvent used for recrystallization) and melting point (°C.) of each compound.

TABLE 9

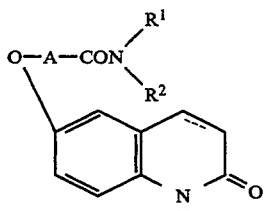

Example 2

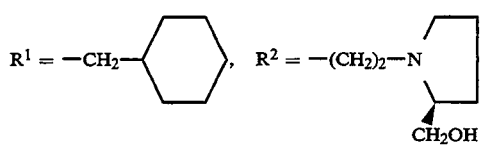

A = —(CH₂)₄—
Carbon-carbon bond between 3- and 4-positions in the carbostyril skeleton: Double bond
Properties: Colorless powdery crystals (recrystallized from diethyl ether)
Melting point: 85–87° C.

Example 3

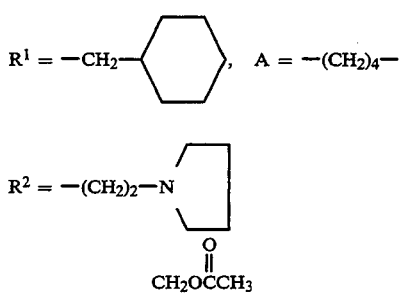

Carbon-carbon bond between 3- and 4-positions in the carbostyril skeleton: Double bond
Properties: Colorless powdery crystals (recrystallized from diethyl ether/n-hexane)
Melting point: 76–78° C.

Example 4

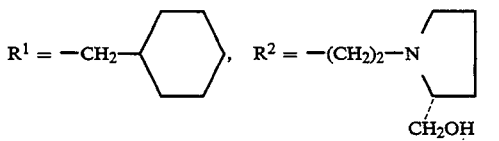

A = —(CH₂)₄—
Carbon-carbon bond between 3- and 4-positions in the carbostyril skeleton: Double bond
Properties: Colorless powdery crystals (recrystallized from diethyl ether)
Melting point: 85–87° C.

Example 5

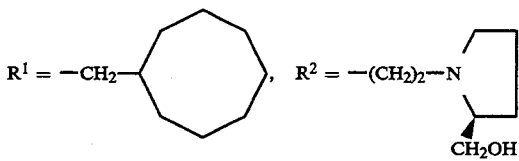

A = —(CH₂)₄—
Carbon-carbon bond between 3- and 4-positions in the carbostyril skeleton: Double bond
Properties: Colorless powdery crystals (recrystallized from diethyl ether)

TABLE 9-continued

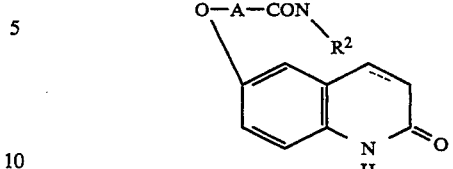

Melting point: 101–102° C.

Example 6

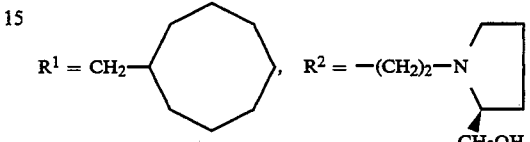

A = —(CH₂)₃—
Carbon-carbon bond between 3- and 4-positions in the carbostyril skeleton: Double bond
Properties: Colorless powdery crystals (recrystallized from diethyl ether)
Melting point: 82–83° C.

Example 7

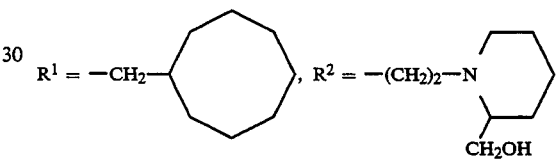

A = —(CH₂)₄—
Carbon-carbon bond between 3- and 4-positions in the carbostyril skeleton: Double bond
Properties: Colorless powdery crystals (recrystallized from diethyl ether)
Melting point: 108–109° C.

Example 8

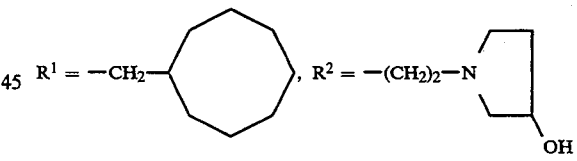

A = —(CH₂)₄—
Carbon-carbon bond between 3- and 4-positions in the carbostyril skeleton: Double bond
Properties: Colorless powdery crystals (recrystallized from ethanol/diethyl ether)
Melting point: 96–98° C. [as (COOH)₂ salt]

Example 9

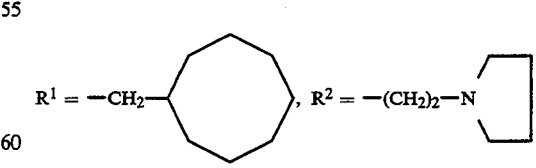

A = —(CH₂)₄—
Carbon-carbon bond between 3- and 4-positions in the carbostyril skeleton: Double bond
Properties: Colorless powdery crystals (recrystallized from chloroform/diethyl ether)
Melting point: 101–103° C.

Example 10

TABLE 9-continued

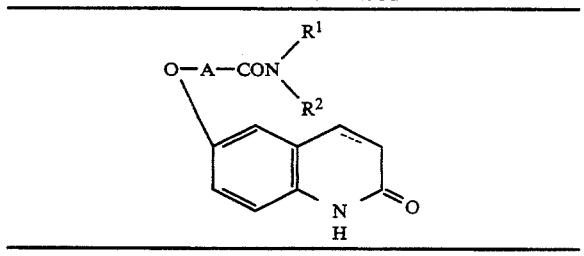

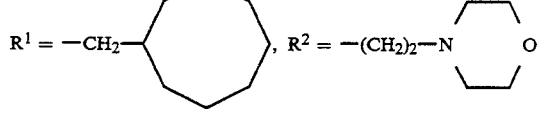

A = —(CH$_2$)$_4$—
Carbon-carbon bond between 3- and 4-positions
in the carbostyril skeleton: Double bond
Properties: Colorless powdery crystals
(recrystallized from diethyl ether)
Melting point: 133–135° C.
Example 11

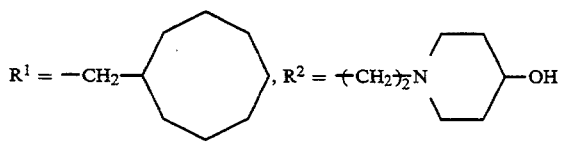

A = —(CH$_2$)$_4$—
Carbon-carbon bond between 3- and 4-positions
in the carbostyril skeleton: Double bond
Properties: Colorless powdery crystals
(recrystallized from ethanol/diethyl ether)
Melting point: 108–110° C.
Example 12

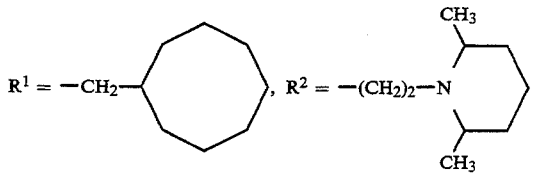

A = —(CH$_2$)$_4$—
Carbon-carbon bond between 3- and 4-positions
in the carbostyril skeleton: Double bond
Properties: Colorless powdery crystals
(recrystallized from diethyl ether)
Melting point: 99–100° C.
Example 13

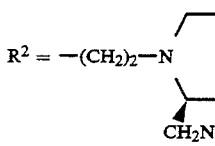

Carbon-carbon bond between 3- and 4-positions
in the carbostyril skeleton: Double bond
Properties: Colorless powdery crystals (recrystallized from ethanol/diethyl ether)

TABLE 9-continued

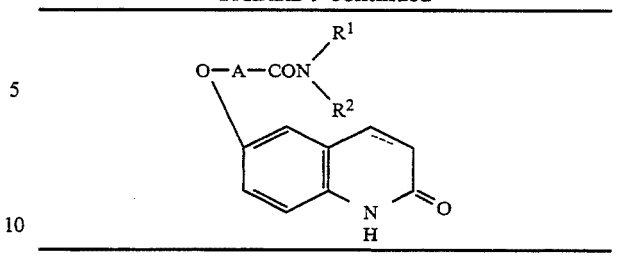

Melting point: 93°–96° C. [as 2.

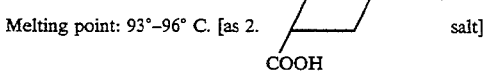

salt]

Example 14

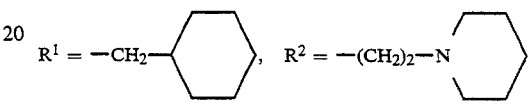

A = —(CH$_2$)$_4$—
Carbon-carbon bond between 3- and 4-positions
in the carbostyril skeleton: Double bond
Properties: Colorless powdery crystals (recrystallized from diethyl ether)
Melting point: 103.5–104.5° C.
Example 15

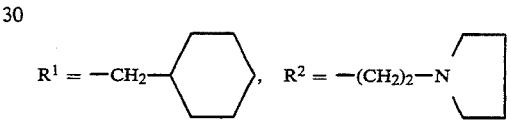

A = —(CH$_2$)$_4$—
Carbon-carbon bond between 3- and 4-positions
in the carbostyril skeleton: Double bond
Properties: Colorless powdery crystals (recrystallized from diethyl ether)
Melting point: 105–106° C.
Example 16

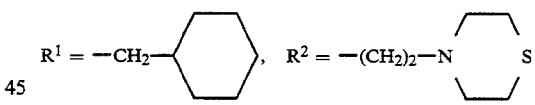

A = —(CH$_2$)$_4$—
Carbon-carbon bond between 3- and 4-positions
in the carbostyril skeleton: Double bond
Properties: Colorless powdery crystals (recrystallized from diethyl ether)
Melting point: 108–109° C.
Example 17

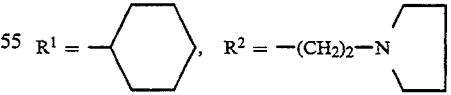

A = —(CH$_2$)$_4$—
Carbon-carbon band between 3- and 4-positions
in the carbostyril skeleton: Double bond
Properties: Colorless powdery crystals
(recrystallized from diethyl ether)
Melting point: 146–147° C.
Example 18

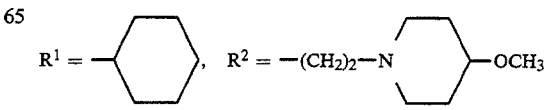

TABLE 9-continued

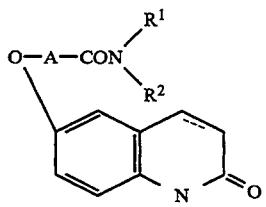

A = —(CH₂)₄—
Carbon-carbon bond between 3- and 4-positions in the carbostyril skeleton: Double bond
Properties: Colorless powdery crystals (recrystallized from diethyl ether)
Melting point: 85–87° C.
Example 19

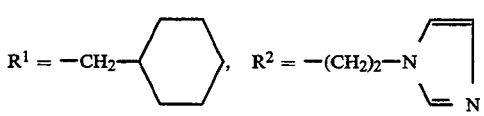

A = —(CH₂)₄—
Carbon-carbon bond between 3- and 4-positions in the carbostyril skeleton: Double bond
Properties: Colorless powdery crystals (recrystallized from ethyl acetate)
Melting point: 124.5–125.5° C.
Example 20

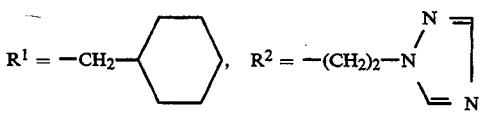

A = —(CH₂)₄—
Carbon-carbon bond between 3- and 4-positions in the carbostyril skeleton: Double bond
Properties: Colorless powdery crystals (recrystallized from ethyl acetate)
Melting point: 120.5–121.5° C.
Example 21

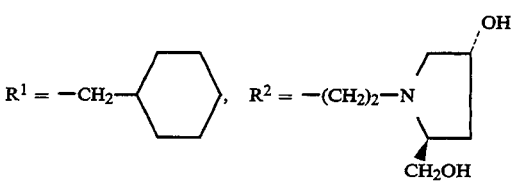

A = —(CH₂)₄—
Carbon-carbon bond between 3- and 4-positions in the carbostyril skeleton: Double bond
Properties: Colorless powdery crystals (recrystallized from diethyl ether)
Melting point: 79–80° C.
Example 22

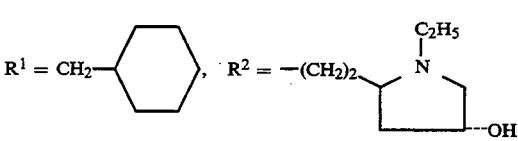

A = —(CH₂)₄—
Carbon-carbon bond between 3- and 4-positions in the carbostyril skeleton: Double bond
Properties: Colorless powdery crystals (recrystallized from diethyl ether)
Melting point: 80–81° C.
Example 23

TABLE 9-continued

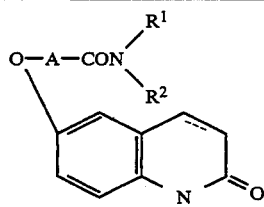

R¹ = —CH₂—⟨tetrahydropyran⟩, R² = —(CH₂)₂—N(C₂H₅)₂

A = —(CH₂)₄—
Carbon-carbon bond between 3- and 4-positions in the carbostyril skeleton: Double bond
Properties: Colorless acicular crystals (recrystallized from ethyl acetate/diethyl ether/n-hexane)
Melting point: 80–83.5° C.
Example 24

R¹ = —CH₂—⟨cycloheptyl⟩, A = —(CH₂)₄—

R² = —(CH₂)₂—N⟨piperidine⟩—OCH₂OCH₃

Carbon-carbon bond between 3- and 4-positions in the carbostyril skeleton: Double bond
Properties: Colorless oily substance
¹H-NMR (CDCl₃) δ ppm:
Example 25

R¹ = —CH₂—⟨3,5-di-tert-butyl-4-hydroxyphenyl⟩

R² = —(CH₂)₂—N(C₂H₅)₂
A = —(CH₂)₄—
Carbon-carbon bond between 3- and 4-positions in the carbostyril skeleton: Double bond
Properties: Colorless powdery crystals (recrystallized from methylene chloride/ethyl acetate)
Melting point: 175.5–176° C.
Example 26

R¹ = —CH₂—⟨cyclohexyl⟩, A = —(CH₂)₄—

R² = —(CH₂)₂—N⟨pyrrolidine⟩—CH₂OCH₃

Carbon-carbon bond between 3- and 4-positions in the carbostyril skeleton: Double bond TABLE 9-continued

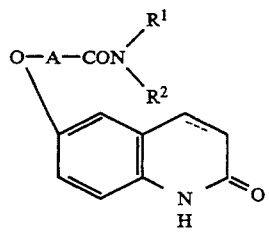

Properties: Colorless powdery crystals (recrystallized from diethyl ether)
Melting point: 72–73° C.
Example 27

$R^2 = -(CH_2)_2-N(C_2H_5)_2$
Carbon-carbon bond between 3- and 4-positions in the carbostyril skeleton: Double bond
Properties: Colorless powdery crystals (recrystallized from diethyl ether)
Melting point: 109–110° C.
Example 28

$R^2 = -(CH_2)_3-N(C_2H_5)_2$
Carbon-carbon bond between 3- and 4-positions in the carbostyril skeleton: Double bond
Properties: Colorless powdery crystals (recrystallized from diethyl ether)
Melting point: 151–153° C. [as (COOH)$_2$ salt]
Example 29

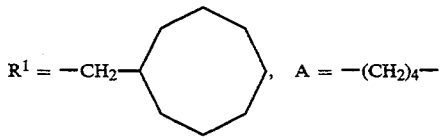

$R^2 = -(CH_2)_4-N(C_2H_5)_2$
Carbon-carbon bond between 3- and 4-positions in the carbostyril skeleton: Double bond
Properties: Colorless powdery crystals (recrystallized from diethyl ether)
Melting point: 90–91° C. [as (COOH)$_2$ salt]
Example 30

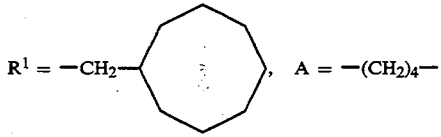

$R^2 = -(CH_2)_2-N(CH_3)_2$
Carbon-carbon bond between 3- and 4-positions in the carbostyril skeleton: Double bond
Properties: Colorless foliate crystals (recrystallized from diethyl ether)
Melting point: 76.5–79° C.
Example 31

TABLE 9-continued

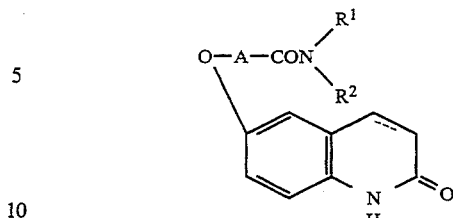

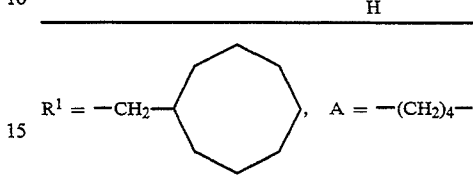

$R^2 = -CH_2CON(C_2H_5)_2$
Carbon-carbon bond between 3- and 4-positions in the carbostyril skeleton: Double bond
Properties: Colorless granular crystals (recrystallized from diethyl ether)
Melting point: 131–132.5° C.
Example 32

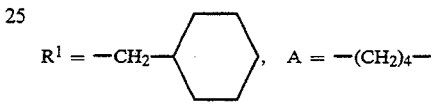

$R^2 = -(CH_2)_2-N(C_2H_5)_2$
Carbon-carbon bond between 3- and 4-positions in the carbostyril skeleton: Double bond
Properties: Colorless and acicular crystals (recrystallized from methylene chloride/n-hexane)
Melting point: 89–90.5° C.
Example 33

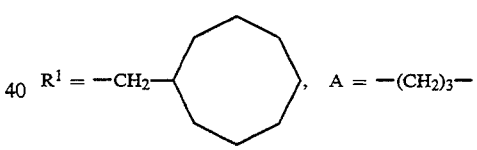

$R^2 = -(CH_2)_2N(C_2H_5)_2$
Carbon-carbon bond between 3- and 4-positions in the carbostyril skeleton: Double bond
Properties: Colorless powdery crystals (recrystallized from diethyl ether)
Melting point: 87.5–89.5° C.
Example 34

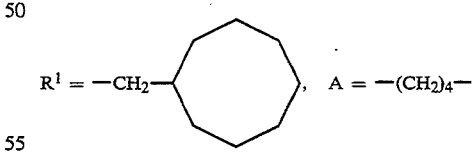

$R^2 = -(CH_2)_2-N(C_2H_5)_2-$
Carbon-carbon bond between 3- and 4-positions in the carbostyril skeleton: Single bond
Properties: Colorless powdery crystals (recrystallized from diethyl ether)
Melting point: 106–108° C. [as (COOH)$_2$ salt]
Example 35

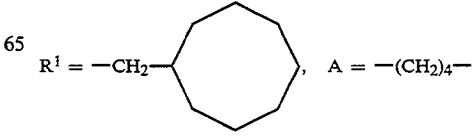

TABLE 9-continued

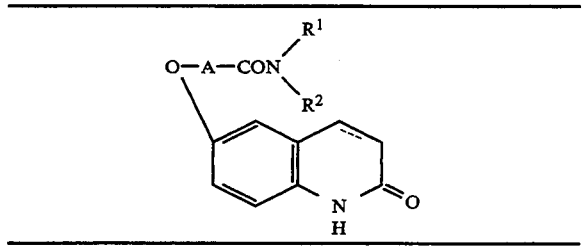

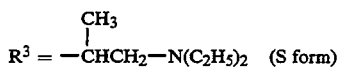

Carbon-carbon bond between 3- and 4-positions
in the carbostyril skeleton: Double bond
Properties: Colorless prism-like crystals
(recrystallized from methylene chloride/
ethyl acetate)
Melting point: 104.5–105.5° C.
Example 36

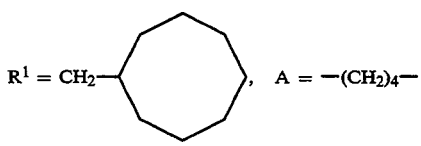

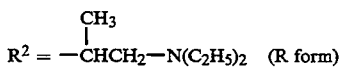

Carbon-carbon bond between 3- and 4-positions
in the carbostyril skeleton: Double bond
Properties: Colorless prism-like crystals
(recrystallized from methylene chloride/
ethyl acetate)
Melting point: 105.5–106° C.
Example 37

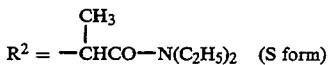

Carbon-carbon bond between 3- and 4-positions
in the carbostyril skeleton: Double bond
Properties: Colorless prism-like crystals
(recrystallized from methylene chloride/
ethyl acetate)
Melting point: 89–90° C.
Example 38

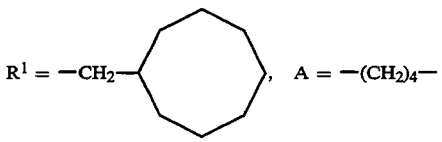

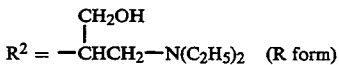

Carbon-carbon bond between 3- and 4-positions
in the carbostyril skeleton: Double bond
Properties: Colorless powdery crystals
(recrystallized from diethyl ether)
Melting point: 96–98° C.

TABLE 9-continued

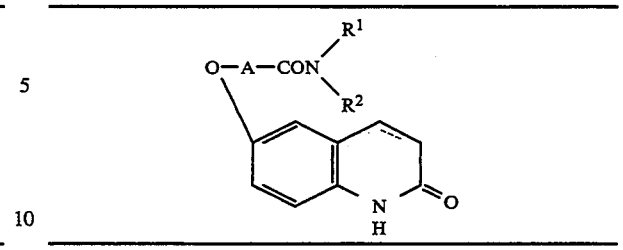

Example 39

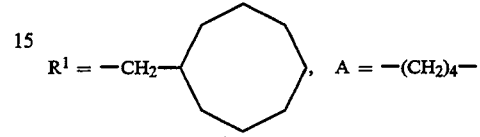

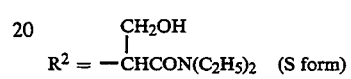

Carbon-carbon bond between 3- and 4-positions
in the carbostyril skeleton: Double bond
Properties: Colorless powdery crystals
(recrystallized from diethyl ether)
Melting point: 72–73° C.
Example 40

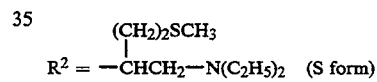

Carbon-carbon bond between 3- and 4-positions
in the carbostyril skeleton: Double bond
Properties: Colorless solid (recrystallized from
diethyl ether/n-hexane)
Melting point: 91.5–92.5° C.
Example 41

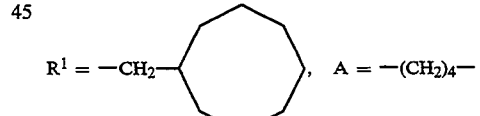

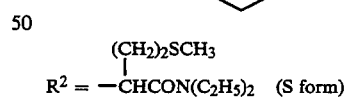

Carbon-carbon bond between 3- and 4-positions
in the carbostyril skeleton: Double bond
Properties: Colorless syrup-like substance
Example 42

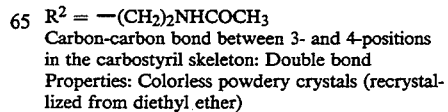

Carbon-carbon bond between 3- and 4-positions
in the carbostyril skeleton: Double bond
Properties: Colorless powdery crystals (recrystal-
lized from diethyl ether)

TABLE 9-continued

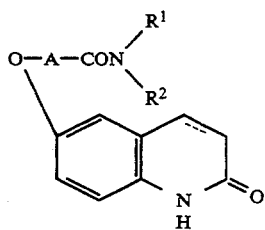

Melting point: 93–95° C.
Example 43

Carbon-carbon bond between 3- and 4-positions
in the carbostyril skeleton: Double bond
Properties: Colorless powdery crystals (recrystal-
lized from diethyl ether)
Melting point: 93–95° C.
Example 44

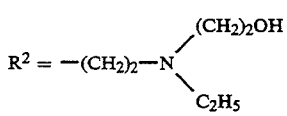

$R^2 = -(CH_2)_2-N(C_2H_5)_2$
Carbon-carbon bond between 3- and 4-positions
in the carbostyril skeleton: Double bond
Properties: Colorless powdery crystals
(recrystallized from diethyl ether)
Melting point: 124–126° C.
Example 45

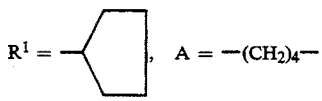

$R^2 = -(CH_2)_2-N(C_2H_5)_2$
Carbon-carbon bond between 3- and 4-positions
in the carbostyril skeleton: Double bond
Properties: Colorless powdery crystals
(recrystallized from diethyl ether)
Melting point: 120.5–122° C.
Example 46

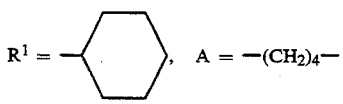

$R^2 = -(CH_2)_2-N(C_2H_5)_2$
Carbon-carbon bond between 3- and 4-positions
in the carbostyril skeleton: Double bond
Properties: Colorless powdery crystals
(recrystallized from diethyl ether)
Melting point: 108–110° C.
Example 47

TABLE 9-continued

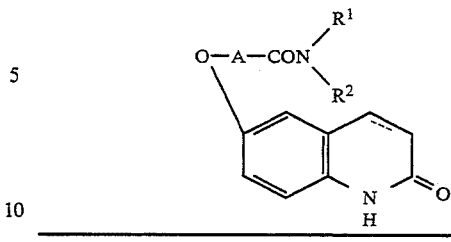

$R^2 = -(CH_2)_2-N(C_2H_5)_2$
Carbon-carbon bond between 3- and 4-positions
in the carbostyril skeleton: Double bond
Properties: Colorless powdery crystals
(recrystallized from diethyl ether)
Melting point: 104.5–106.5° C.
Example 48

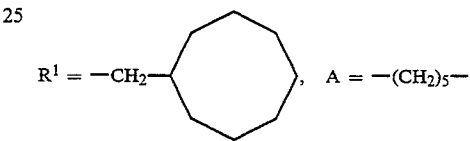

$R = -(CH_2)_2-N(C_2H_5)_2$
Carbon-carbon bond between 3- and 4-positions
in the carbostyril skeleton: Double bond
Properties: Colorless powdery crystals
(recrystallized from diethyl ether/
n-hexane)
Melting point: 104–106.5° C.
Example 49

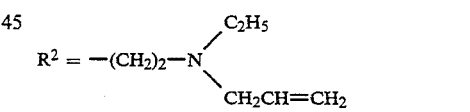

Carbon-carbon bond between 3- and 4-positions
in the carbostyril skeleton: Double bond
Properties: Colorless powdery crystals (recrystal-
lized from diethyl ether/n-hexane)
Melting point: 92–93° C.
Example 50

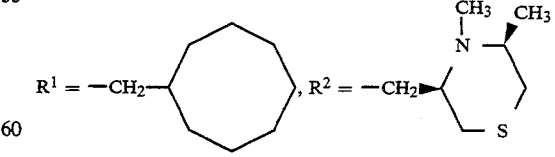

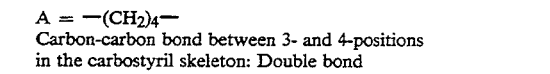

$A = -(CH_2)_4-$
Carbon-carbon bond between 3- and 4-positions
in the carbostyril skeleton: Double bond
Properties: Colorless powdery crystals (recrystal-
lized from diethyl ether/n-hexane)
Melting point: 111° C.
Example 51

TABLE 9-continued

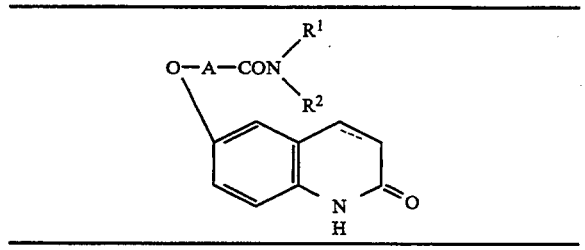

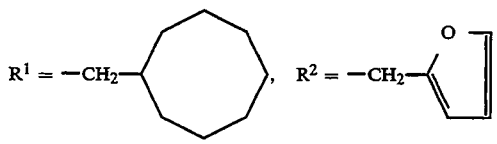

A = —(CH₂)₄—
Carbon-carbon bond between 3- and 4-positions in the carbostyril skeleton: Double bond
Properties: Colorless powdery crystals (recrytallized from diethyl ether)
Melting point: 101–103° C.
Example 52

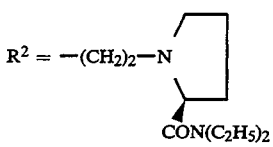

Carbon-carbon between 3- and 4-positions in the carbostyril skeleton: Double bond
Properties: Colorless syrup-like substance
Example 53

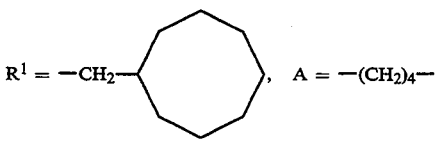

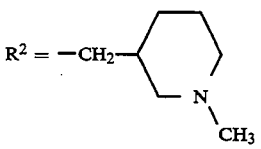

Carbon-carbon bond between 3- and 4-positions in the carbostyril skeleton: Double bond
Properties: Colorless powdery crystals (recrystallized from methylene chloride/ethyl acetate/n-hexane)
Melting point: 195–198° C.
Example 54

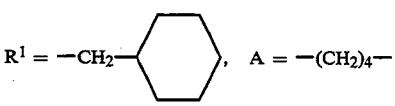

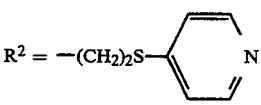

TABLE 9-continued

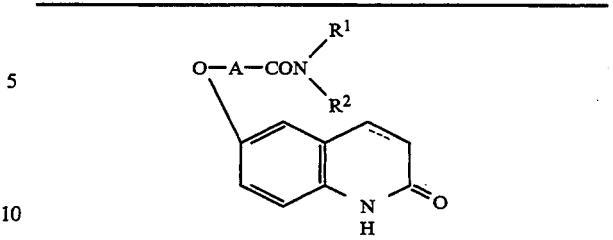

Carbon-carbon bond between 3- and 4-positions in the carbostyril skeleton: Double bond
Properties: Colorless amorphous substance
Example 55

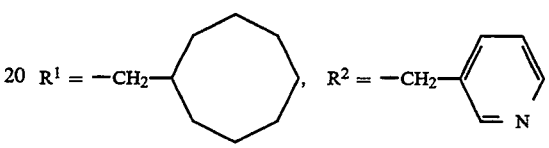

A = —(CH₂)₄—
Carbon-carbon bond between 3- and 4-positions in the carbostyril skeleton: Double bond
Properties: Colorless prism-like crystals (recrystallized from ethyl acetate/n-hexane)
Melting point: 93.5–95° C.
Example 56

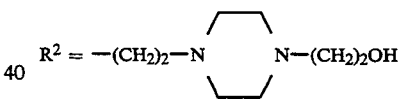

Carbon-carbon bond between 3- and 4-positions in the carbostyril skeleton: Double bond
Properties: Colorless powdery crystals (recrystallized from methylene chloride/diethyl ether)
Melting point: 99–102° C.
Example 57

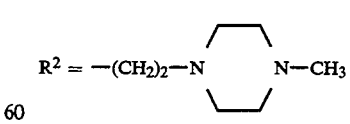

Carbon-carbon bond between 3- and 4-positions in the carbostyril skeleton: Double bond
Properties: Colorless prism-like crystals (recrystallized from methylene chloride/ethyl acetate/n-hexane)
Melting point: 80.5–82° C.
Example 58

TABLE 9-continued

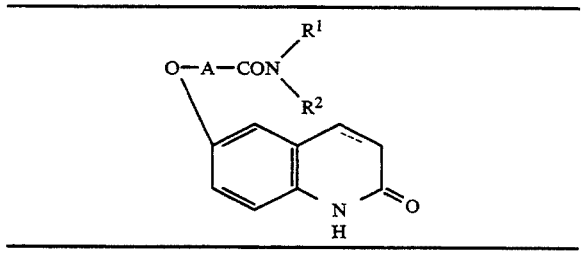

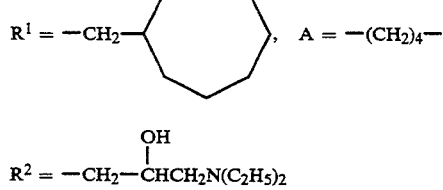

$R^2 = -CH_2-\overset{OH}{\underset{|}{C}}HCH_2N(C_2H_5)_2$

Carbon-carbon bond between 3- and 4-positions in the carbostyril skeleton: Double bond
Properties: Colorless powdery crystals (recrystallized from diethyl ether)
Melting point: 61–63° C.
Example 59

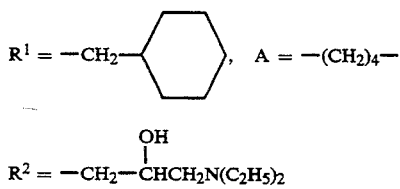

$R^2 = -CH_2-\overset{OH}{\underset{|}{C}}HCH_2N(C_2H_5)_2$

Carbon-carbon bond between 3- and 4-positions in the carbostyril skeleton: Double bond
Properties: Colorless powdery crystals (recrystallized from diethyl ether)
Melting point: 103–105° C.
Example 60

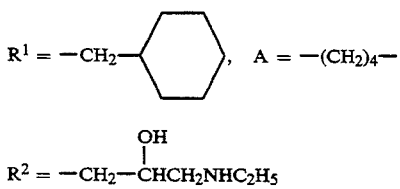

$R^2 = -CH_2-\overset{OH}{\underset{|}{C}}HCH_2NHC_2H_5$

Carbon-carbon bond between 3- and 4-positions in the carbostyril skeleton: Double bond
Properties: Colorless powdery crystals (recrystallized from diethyl ether)
Melting point: 82–84° C.
Example 61

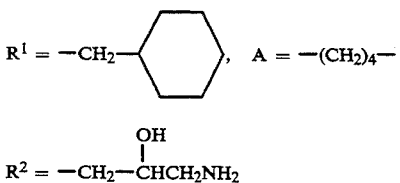

$R^2 = -CH_2-\overset{OH}{\underset{|}{C}}HCH_2NH_2$

Carbon-carbon bond between 3- and 4-positions in the carbostyril skeleton: Double bond
Properties: Colorless powdery crystals (recrystallized from ethanol/diethyl ether)
Melting point: 101–103° C. [as (COOH)$_2$ salt]
Example 62

TABLE 9-continued

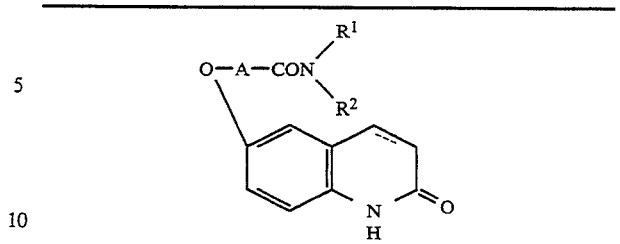

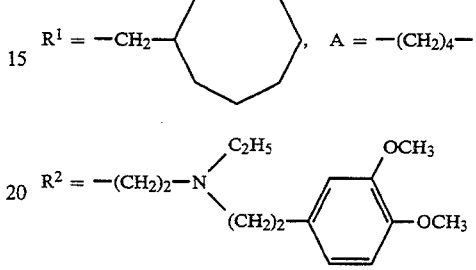

Carbon-carbon bond between 3- and 4-positions in the carbostyril skeleton: Double bond
Properties: Colorless powdery crystals (recrystallized from ethanol/diethyl ether)
Melting point: 74–76° C. [as (COOH)$_2$ salt]
Example 63

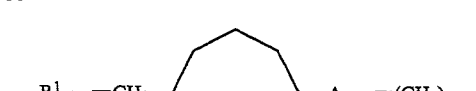

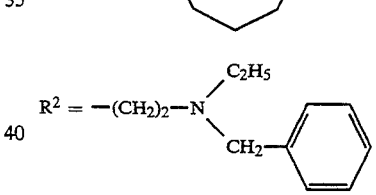

Carbon-carbon bond between 3- and 4-positions in the carbostyril skeleton: Double bond
Properties: Colorless powdery crystals (recrystallized from ethanol/diethyl ether/n-hexane)
Melting point: 137–139° C. [as (COOH)$_2$ salt]
Example 64

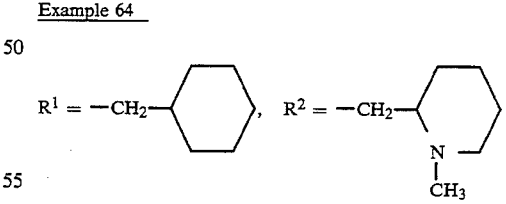

$A = -(CH_2)_4-$
Carbon-carbon bond between 3- and 4-positions in the carbostyril skeleton: Double bond
Properties: Colorless powdery crystals (recrystallized from diethyl ether)
Melting point: 109–111° C.
Example 65

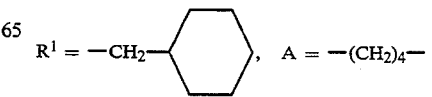

TABLE 9-continued

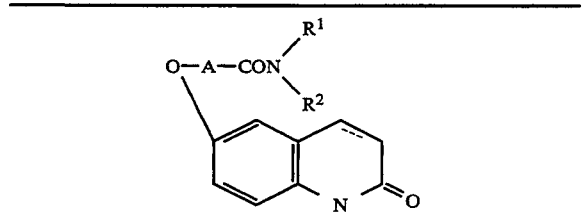

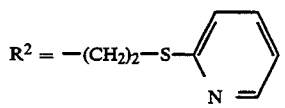

Carbon-carbon bond between 3- and 4-positions in the carbostyril skeleton: Double bond
Properties: Light yellow solid (recrystallized from methylene chloride/n-hexane)
Melting point: 130.5–132.5° C.

Example 66

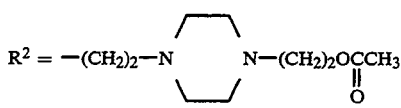

Carbon-carbon bond between 3- and 4-positions in the carbostyril skeleton: Double bond
Properties: Colorless syrup-like substance Example 67

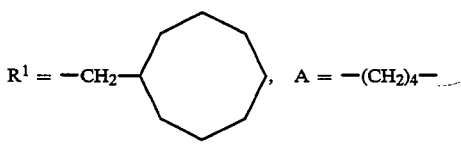

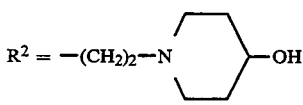

Carbon-carbon bond between 3- and 4-positions in the carbostyril skeleton: Double bond
Properties: Colorless powdery crystals (recrystallized from diethyl ether)
Melting point: 106–107° C.

Example 68

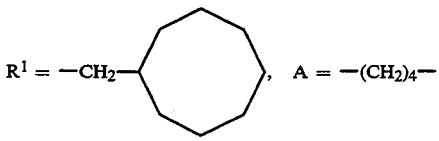

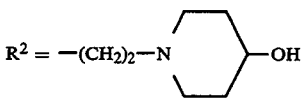

Carbon-carbon bond between 3- and 4-positions in the carbostyril skeleton: Double bond
Properties: Colorless powdery crystals (recrystallized from diethyl ether)
Melting point: 112–113° C.

TABLE 9-continued

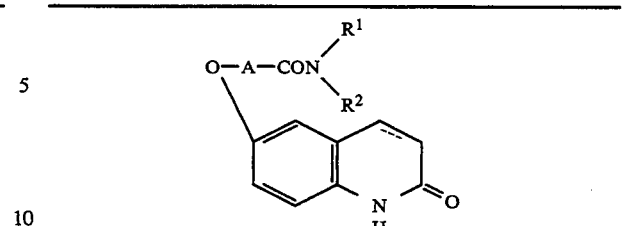

Example 69

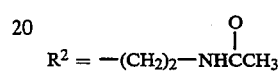

Carbon-carbon bond between 3- and 4-positions in the carbostyril skeleton: Double bond
Properties: Colorless powdery crystals (recrystallized from diethyl ether)
Melting point: 137–138° C.

Example 70

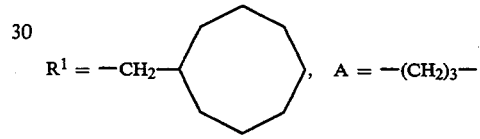

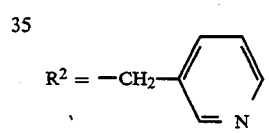

Carbon-carbon bond between 3- and 4-positions in the carbostyril skeleton: Double bond
Properties: Colorless powdery crystals (recrystallized from diethyl ether)
Melting point: 123–123.5° C.

Example 71

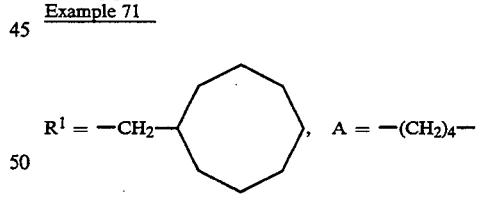

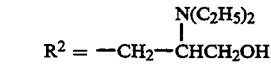

Carbon-carbon bond between 3- and 4-position in the carbostyril skeleton: Double bond
Properties: Colorless powdery crystals (recrystallized from diethyl ether)
Melting point: 88–90° C.

Example 72

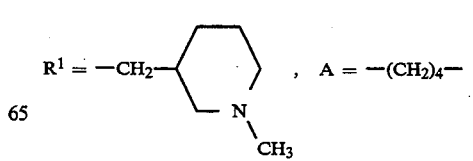

TABLE 9-continued

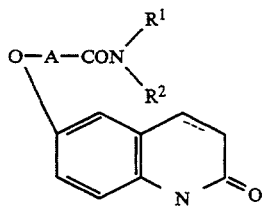

Carbon-carbon bond between 3- and 4-positions
in the carbostyril skeleton: Double bond
Properties: Colorless solid
Example 73

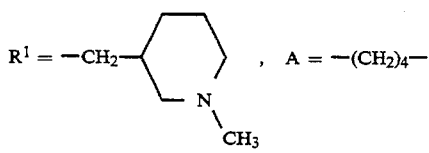

$R^2 = -(CH_2)_2-OCCH_3$
         $\underset{\|}{O}$

Carbon-carbon bond between 3- and 4-positions
in the carbostyril skeleton: Double bond
Properties: Colorless solid
Example 74

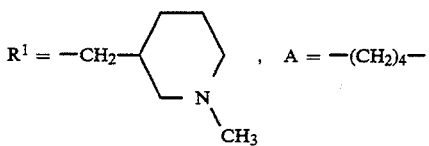

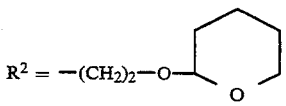

Carbon-carbon bond between 3- and 4-positions
in the carbostyril skeleton: Double bond
Properties: Colorless solid
Example 75

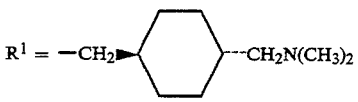

$R^2 = -(CH_2)_2OH$, $A = -(CH_2)_4-$
Carbon-carbon bond between 3- and 4-positions
in the carbostyril skeleton: Double bond
Properties: Colorless powdery crystals
(recrystallized from ethanol)
Melting point: 96–98° C. [as $(COOH)_2$ salt]
Example 76

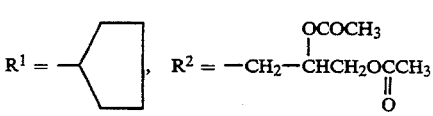

$A = -(CH_2)_4-$
Carbon-carbon bond between 3- and 4-positions
in the carbostyril skeleton: Double bond
Properties: Colorless powdery crystals
(recrystallized from diethyl ether)
Melting point: 105–106° C.
Example 77

TABLE 9-continued

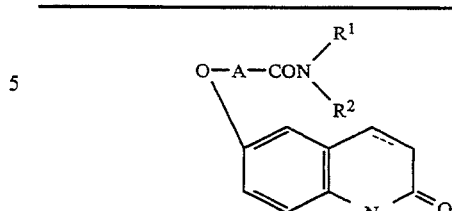

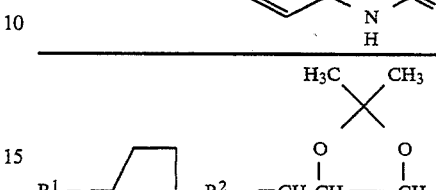

$A = -(CH_2)_4-$
Carbon-carbon bond between 3- and 4-positions
in the carbostyril skeleton: Double bond
Properties: Colorless powdery crystals
(recrystallized from diethyl ether)
Melting point: 134–135° C.
Example 78

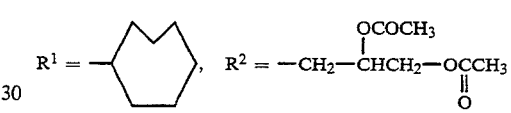

$A = -(CH_2)_4-$
Carbon-carbon bond between 3- and 4-positions
in the carbostyril skeleton: Double bond
Properties: Colorless powdery crystals
(recrystallized from diethyl ether)
Melting point: 109–110° C.
Example 79

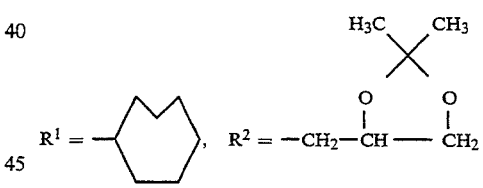

$A = -(CH_2)_4-$
Carbon-carbon bond between 3- and 4-positions
in the carbostyril skeleton: Double bond
Properties: Colorless powdery crystal
(recrystallized from diethyl ether)
Melting point: 132–133° C.
Example 80

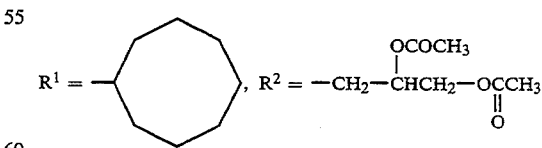

$A = -(CH_2)_4-$
Carbon-carbon bond between 3- and 4-positions
in the carbostyril skeleton: Double bond
Properties: Colorless powdery crystals
(recrystallized from diethyl ether)
Melting point: 124–125° C.
Example 81

TABLE 9-continued

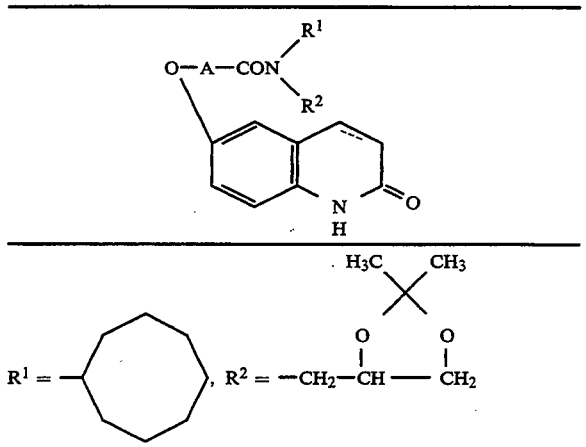

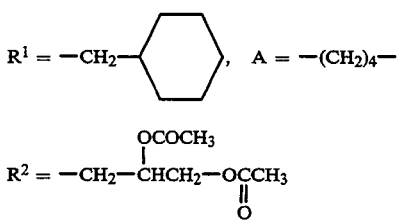

A = —(CH$_2$)$_4$—
Carbon-carbon bond between 3- and 4-positions in the carbostyril skeleton: Double bond
Properties: Colorless granular crystals (recrystallized from diethyl ether)
Melting point: 137–138° C.
Example 82

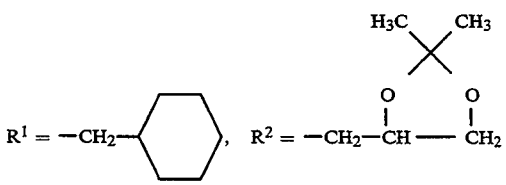

Carbon-carbon bond between 3- and 4-positions in the carbostyril skeleton: Double bond
Properties: Colorless powdery crystals (recrystallized from ethanol/diethyl ether)
Melting point: 98–100° C.
Example 83

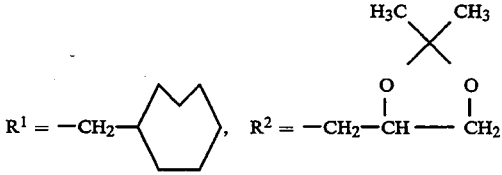

A = —(CH$_2$)$_4$—
Carbon-carbon bond between 3- and 4-positions in the carbostyril skeleton: Double bond
Properties: Colorless granular crystals (recrystallized from diethyl ether)
Melting point: 121–123° C.
Example 84

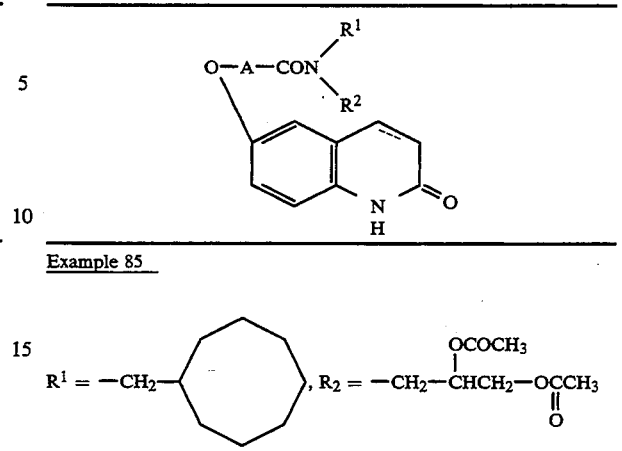

A = —(CH$_2$)$_4$—
Carbon-carbon bond between 3- and 4-positions in the carbostyril skeleton: Double bond
Properties: Colorless foliate crystals (recrystallized from diethyl ether)
Melting point: 107–108° C.

TABLE 9-continued

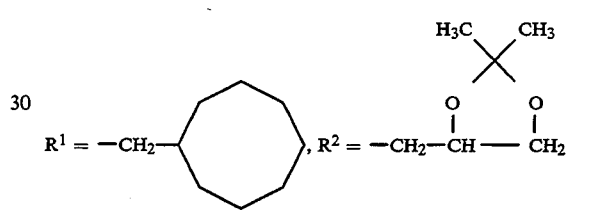

Example 85

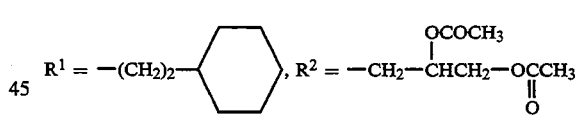

A = —(CH$_2$)$_4$—
Carbon-carbon bond between 3- and 4-positions in the carbostyril skeleton: Double bond
Properties: Colorless powdery crystals (recrystallized from diethyl ether)
Melting point: 69–71° C.
Example 86

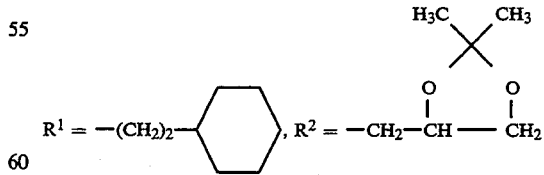

A = —(CH$_2$)$_4$—
Carbon-carbon bond between 3- and 4-positions in the carbostyril skeleton: Double bond
Properties: Colorless granular crystals (recrystallized from diethyl ether)
Melting point: 107–108° C.
Example 87

R$^1$ = —(CH$_2$)$_2$— [cyclohexyl], R$^2$ = —CH$_2$—CH(OCOCH$_3$)CH$_2$—OCCH$_3$ (||O)

A = —(CH$_2$)$_4$—
Carbon-carbon bond between 3- and 4-positions in the carbostyril skeleton: Double bond
Properties: Colorless powdery crystals (recrystallized from diethyl ether)
Melting point: 77–78° C.
Example 88

R$^1$ = —(CH$_2$)$_2$— [cyclohexyl], R$^2$ = —CH$_2$—CH—CH$_2$ (with O—C(CH$_3$)$_2$—O)

A = —(CH$_2$)$_4$—
Carbon-carbon bond between 3- and 4-positions in the carbostyril skeleton: Double bond
Properties: Colorless powdery crystals (recrystallized from diethyl ether)
Melting point: 107–108° C.
Example 89

TABLE 9-continued

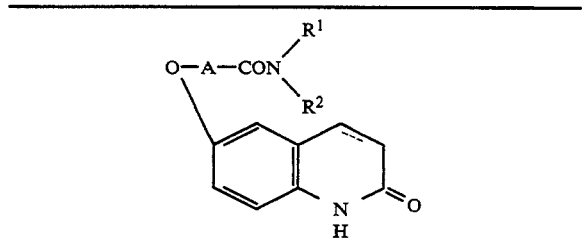

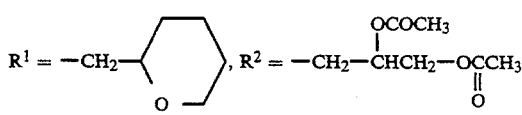

A = —(CH₂)₄—
Carbon-carbon bond between 3- and 4-positions
in the carbostyril skeleton: Double bond
Properties: Colorless powdery crystals
(recrystallized from diethyl ether)
Melting point: 68–70° C.
Example 90

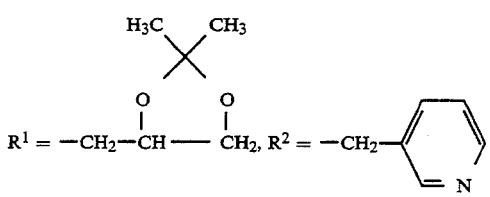

A = —(CH₂)₄—
Carbon-carbon bond between 3- and 4-positions
in the carbostyril skeleton: Double bond
Properties: Colorless prism-like crystals
(recrystallized from methylene
chloride/diethyl ether)
Melting point: 169–170.5° C.
Example 91

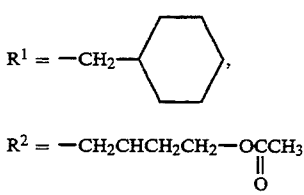

R² = —CH₂CHCH₂CH₂—OCCH₃
                              ‖
                              O

A = —(CH₂)₄—
Carbon-carbon bond between 3- and 4-positions
in the carbostyril skeleton: Double bond
Properties: Colorless powdery crystals
(recrystallized from diethyl ether)
Melting point: 79–81° C.
Example 92

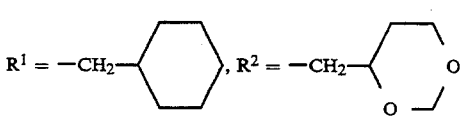

A = —(CH₂)₄—
Carbon-carbon bond between 3- and 4-positions
in the carbostyril skeleton: Double bond
Properties: Colorless powdery crystals
(recrystallized from diethyl ether)
Melting point: 120–121° C.
Example 93

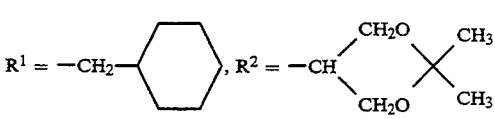

TABLE 9-continued

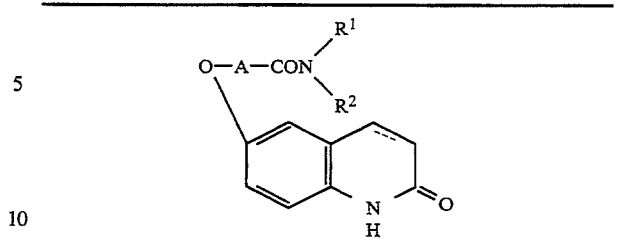

A = —(CH₂)₄—
Carbon-carbon bond between 3- and 4-positions
in the carbostyril skeleton: Double bond
Properties: Colorless acicular crystals (recrystallized from methylene chloride/diethyl
ether)
Melting point: 97.5–99.5° C.
Example 94

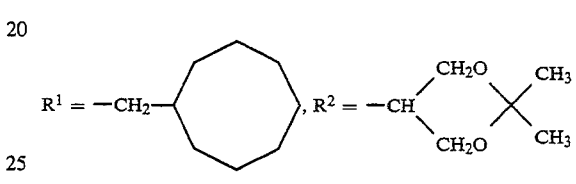

A = —(CH₂)₄—
Carbon-carbon bond between 3- and 4-positions
in the carbostyril skeleton: Double bond
Properties: Colorless powdery crystals
(recrystallized from diethyl ether)
Melting point: 123–125° C.
Example 95

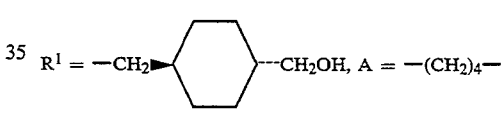

OH
            |
R² = —CH₂CHCH₂OH

Carbon-carbon bond between 3- and 4-positions
in the carbostyril skeleton: Double bond
Properties: Colorless powdery crystals (recrystallized from ethanol/diethyl ether)
Melting point: 156–159° C.
Example 96

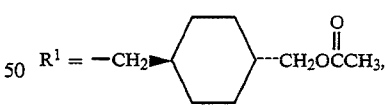

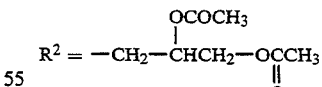

A = —(CH₂)₄—
Carbon-carbon bond between 3- and 4-positions
in the carbostyril skeleton: Double bond
Properties: Colorless powdery crystals
(recrystallized from diethyl ether)
Melting point: 100–102° C.
Example 97

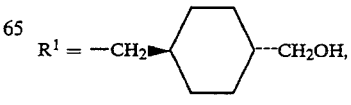

TABLE 9-continued

[Structure: carbostyril with O—A—CON(R¹)(R²) substituent at 6-position]

R² = —CH₂—CH(O—C(CH₃)₂—O)—CH₂ (cyclic acetonide)

A = —(CH₂)₄—
Carbon-carbon bond between 3- and 4-positions in the carbostyril skeleton: Double bond
Properties: Colorless powdery crystals (recrystallized from ethanol/diethyl ether)
Melting point: 128–130° C.
Example 98

R¹ = —CH₂—(cyclohexyl)—, R² = —CH₂—CH(OH)CH₂—OCH₃

A = —(CH₂)₄—
Carbon-carbon bond between 3- and 4-positions in the carbostyril skeleton: Double bond
Properties: Colorless powdery crystals (recrystallized from ethanol/diethyl ether)
Melting point: 56–58° C.
Example 99

R¹ = —CH₂—(cyclohexyl)—, R² = —CH₂—CH(OCH₃)CH₂OCH₃

A = —(CH₂)₄—
Carbon-carbon bond between 3- and 4-positions in the carbostyril skeleton: Double bond
Properties: Colorless powdery crystals (recrystallized from diethyl ether)
Melting point: 66–68° C.
Example 100

R¹ = —CH₂—(cyclohexyl)—, R² = —CH(CH₂OH)COOCH₃

A = —(CH₂)₄—
Carbon-carbon bond between 3- and 4-positions in the carbostyril skeleton: Double bond
Properties: Colorless powdery crystals (recrystallized from ethyl acetate/diethyl ether)
Melting point: 97–99° C.
Example 101

R¹ = —CH₂—(cyclohexyl)—, R² = —(CH₂)₂—O—(tetrahydropyran-2-yl)

A = —(CH₂)₄—
Carbon-carbon bond between 3- and 4-positions in the carbostyril skeleton: Double bond
Properties: Colorless granular crystals (recrystallized from ethyl acetate/diethyl ether)
Melting point: 135–136° C.
Example 102

R¹ = —CH₂—(cyclohexyl)—CH₂OH, R² = —C₂H₅

A = —(CH₂)₄—
Carbon-carbon bond between 3- and 4-positions in the carbostyril skeleton: Double bond
Properties: Colorless powdery crystals (recrystallized from ethanol/diethyl ether)
Melting point: 162–163° C.
Example 103

R¹ = —CH₂—(cyclohexyl)—CH₂OCOCH₃

R² = —C₂H₅, A = —(CH₂)₄—
Carbon-carbon bond between 3- and 4-positions in the carbostyril skeleton: Double bond
Properties: Colorless powdery crystals (recrystallized from ethanol/diethyl ether)
Melting point: 141–142° C.
Example 104

R¹ = —CH₂—(cyclohexyl)—CH₂OH

R² = —(CH₂)₂OH, A = —(CH₂)₄—
Carbon-carbon bond between 3- and 4-positions in the carbostyril skeleton: Double bond
Properties: Colorless powdery crystals (recrystallized from diethyl ether)
Melting point: 122–124° C.
Example 105

R¹ = —CH₂—(cyclohexyl)—, R² = —CH₂—CH(OH)CH₂Cl

A = —(CH₂)₄—
Carbon-carbon bond between 3- and 4-positions in the carbostyril skeleton: Double bond
Properties: Colorless powdery crystals (recrystallized from diethyl ether)
Melting point: 126–127° C.
Example 106

R¹ = —CH₂—(cyclohexyl)—, R² = —CH₂—CH(OH)CH₂Cl

A = —(CH₂)₄—

TABLE 9-continued

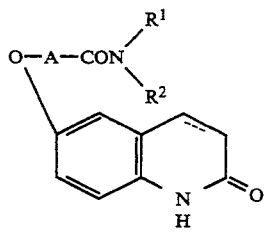

Carbon-carbon bond between 3- and 4-positions
in the carbostyril skeleton: Double bond
Properties: Colorless powdery crystals
(recrystallized from diethyl ether)
Melting point: 75–77° C.
Example 107

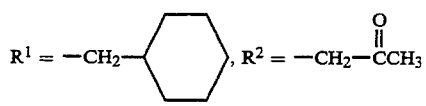

A = —(CH$_2$)$_4$—
Carbon-carbon bond between 3- and 4-positions
in the carbostyril skeleton: Double bond
Properties: Colorless powdery crystals
(recrystallized from diethyl ether)
Melting point: 86–88° C.
Example 108

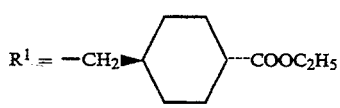

R$^2$ = —CH$_2$—CHCH$_3$ (OH), A = —(CH$_2$)$_4$—

Carbon-carbon bond between 3- and 4-positions
in the carbostyril skeleton: Double bond
Properties: Colorless amorphous substance
(recrystallized from methylene
chloride/diethyl ether)
Melting point: 133.5–135° C.
Example 109

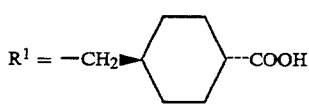

R$^2$ = —CH$_2$—CHCH$_3$ (OH), A = —(CH$_2$)$_4$—

Carbon-carbon bond between 3- and 4-positions
in the carbostyril skeleton: Double bond
Properties: Colorless powdery crystals
(recrystallized from chloroform/
methanol/diethyl ether)
Melting point: 130–132.5° C.
Example 110

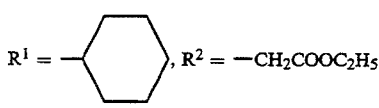

A = —(CH$_2$)$_4$—
Carbon-carbon bond between 3- and 4-positions
in the carbostyril skeleton: Double bond
Properties: Colorless granular crystals (crystallized from chloroform/diethyl ether)
Melting point: 122–124° C.
Example 111

TABLE 9-continued

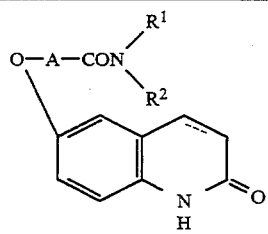

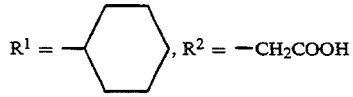

A = —(CH$_2$)$_4$—
Carbon-carbon bond between 3- and 4-positions
in the carbostyril skeleton: Double bond
Properties: Colorless acicular crystals (recrystallized from methanol/water)
Melting point: 88–90° C.
Example 112

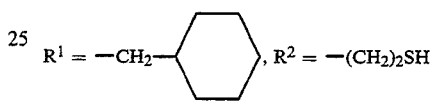

A = —(CH$_2$)$_4$—
Carbon-carbon bond between 3- and 4-positions
in the carbostyril skeleton: Double bond
Properties: Light yellow powdery crystals
(recrystallized from methylene
chloride/diethyl ether)
Melting point: 122.5–125.5° C.
Example 113

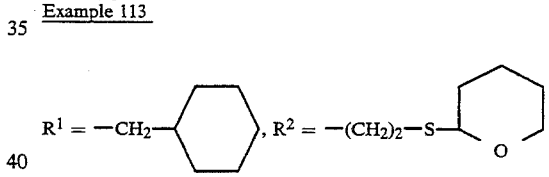

A = —(CH$_2$)$_4$—
Carbon-carbon bond between 3- and 4-positions
in the carbostyril skeleton: Double bond
Properties: Colorless solid (recrystallized from
ethyl acetate/n-hexane)
Melting point: 85–87° C.
Example 114

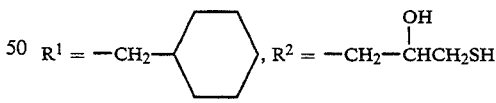

A = —(CH$_2$)$_4$—
Carbon-carbon bond between 3- and 4-positions
in the carbostyril skeleton: Double bond
Properties: Colorless powdery crystals
(recrystallized from diethyl ether)
Melting point: Above 150° C. (decomposed)
Example 115

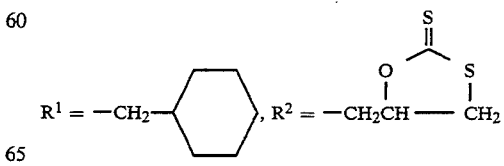

A = —(CH$_2$)$_4$—
Carbon-carbon bond between 3- and 4-positions
in the carbostyril skeleton: Double bond TABLE 9-continued

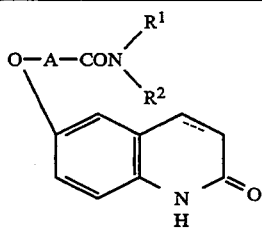

Properties: Yellow granular cyrstals (recrystallized from chloroform/diethyl ether)
Melting point: Above 84° C. (decomposed)
Example 116

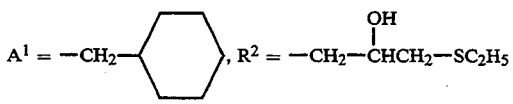

A = —(CH$_2$)$_4$—
Carbon-carbon bond between 3- and 4-positions in the carbostyril skeleton: Double bond
Properties: Colorless powdery crystals (recrystallized from diethyl ether)
Melting point: 128–129° C.
Example 117

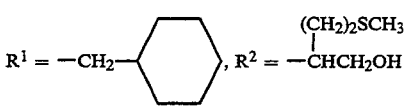

A = —(CH$_2$)$_4$—
Carbon-carbon bond between 3- and 4-positions in the carbostyril skeleton: Double bond
Properties: Colorless prism-like crystals (recrystallized from methylene chloride/ethyl acetate/diethyl ether)
Melting point: 106.5–108° C.
Example 118

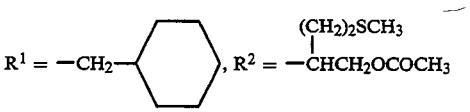

A = —(CH$_2$)$_4$—
Carbon-carbon bond between 3- and 4-positions in the carbostyril skeleton: Double bond
Properties: Colorless prism-like crystals (recrystallized from methylene chloride/ diethyl ether/n-hexane)
Melting point: 113.5–114.5° C.
Example 119

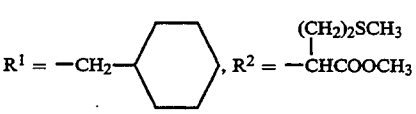

A = —(CH$_2$)$_4$—
Carbon-carbon bond between 3- and 4-positions in the carbostyril skeleton: Double bond
Properties: Colorless granular crystals (recrystallized from chloroform/ethyl acetate/ n-hexane)
Melting point: 110–113° C.
Example 120

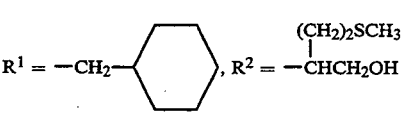

TABLE 9-continued

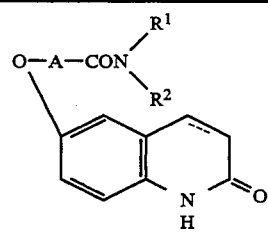

A = —(CH$_2$)$_3$—
Carbon-carbon bond between 3- and 4-postions in the carbostyril skeleton: Double bond
Properties: Colorless powdery crystals (recrystallized from diethyl ether)
Melting point: 124–125° C.
Example 121

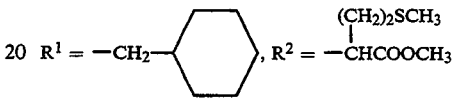

A = —(CH$_2$)$_3$—
Carbon-carbon bond between 3- and 4-positions in the carbostyril skeleton: Double bond
Properties: Colorless powdery crystals (recrystallized from diethyl ether)
Melting point: 126–128° C.

Some of the compounds shown in the above Table 9 were determined by means of $^1$NMR (CDCl$_3$, δ ppm). The data obtained are as follows:

Example 24

1.00–2.01 (23H, m)
2.20 (2H, t, J=10 Hz)
2.33–2.57 (4H, m)
2.67–2.90 (2H, m)
3.07–3.28 (2H, m)
3.36 (3H, s)
3.28–3.52 (2H, m)
3.57 (1H,m), 4.02 (2H, s)
4.67 (2H, s)
6.73 (1H, d, J=9 Hz)
6.98 (1H, d, J=2 Hz)
7.15 (1H, dd, J=9 and 2 Hz)
7.38 (1H, d, J=9 Hz)
7.74 (1H, d, J=9 Hz)

Example 41

1.00–2.00 (27H, m)
2.11 (3H, s)
2.20–2.70 (4H, m)
2.92–3.60 (6H, m)
4.03 (2H, m)
5.55–5.65 (1H, m)
6.73 (1H, d, J=9 Hz)
6.98 (1H, d, J=3 Hz)
7.15 (1H, dd, J=3 and 8 Hz)
7.39 (1H, d, J=8 Hz)
7.76 (1H, d, J=9 Hz)
12.58 (1H, b)

Example 52

0.79–2.22 (27H, m)
2.22–2.68 (4H, m)
2.68–2.88 (1H, m)
3.05–3.65 (8H, m)

4.02 (2H, s)
6.73 (1H, d, J=9 Hz)
6.98 (1H, d, J=2 Hz)
7.16 (1H, d, J=9 Hz)
7.37 (1H, dd, J=2 and 9 Hz)
7.77 (1H, d, J=9 Hz)
12.18 (1H, s)

Example 54

0.80–2.10 (15H, m)
2.40 (2H, s)
3.05–3.30 (4H, m)
3.45–3.65 (2H, m)
4.04 (2H, s)
6.72 (1H, d, J=9 Hz)
6.98 (1H, d, J=2.5 Hz)
7.14 (1H, dd, J=2.5 and 9 Hz)
7.27–7.41 (3H, m)
7.75 - (1H, d, J=9 Hz)
8.42 (2H, d, J=6 Hz)
12.60 (1H, b)

Example 66

0.76–1.40 (5H, m)
1.48–1.92 (10H, m)
2.06 (3H, s)
2.30–2.70 (14H, m)
3.16 (2H, dd, J=7 Hz and 10 Hz)
3.43 (2H, m), 4.02 (2H, s)
4.18 (2H, t, J=7 Hz)
6.71 (1H, d, J=9.5 Hz)
6.98 (1H, d, J=2.5 Hz)
7.14 (1H, dd, J=2.5 Hz and 9 Hz)
7.36 (1H, d, J=9 Hz)
7.74 (1H, d, J=9.5 Hz)

Example 72

0.75–2.18 (9H, m)
2.24 (3H, s)
2.30–2.90 (6H, m)
3.10–3.40 (2H, m)
3.40–3.60 (2H, m)
3.70–3.90 (2H, m)
3.90–4.10 (2H, m)
6.69 (1H, d, J=9.5 Hz)
6.97 (1H, s)
7.02–7.20 (1H, m)
7.30–7.36 (1H, m)
7.73 (1H, d, J=9.5 Hz)
11.69 (1H, b)

Example 73

0.75–2.22 (9H, m)
2.05 (3H, s)
2.24–2.60 (5H, m)
2.60–2.80 (1H, m)
2.80–3.06 (1H, m)
3.06–3.40 (2H, m)
3.40–3.80 (4H, m)
4.02 (2H, s)
4.01–4.30 (2H, m)
6.72 (1H, d, J=9.5 Hz)
6.98 (1H, s)
7.13 (1H, d, J=9 Hz)
7.39 (1H, d, J=9 Hz)
7.75 (1H, d, J=9.5 Hz)

Example 74

0.80–2.10 (15H, m)
2.24 (3H, s)
2.33–2.57 (2H, m)
2.57–2.80 (2H, m)
3.10–3.95 (10H, m)
4.01 (2H, s), 4.56 (1H, s)
6.71 (1H, s, J=9.5 Hz)
6.98 (1H, d, J=2.6 Hz)
7.14 (1H, dd, J=2.6 Hz and 9 Hz)
7.33 (1H, d, J=9 Hz)
7.24 (1H, d, J=9.5 Hz)

Example 114

1.72–2.20 (15H, m)
2.20–2.53 (2H, m)
2.53–3.83 (8H, m)
3.94 (2H, s)
6.64 (1H, d, J=10 Hz)
6.90 (1H, d, J=2 Hz)
7.06 (1H, dd, J=2 Hz and 9 Hz)
7.32 (1H, d, J=9 Hz)
7.67 (1H, d, J=10 Hz)
12.66 (1H, s)

Example 115

0.82–1.95 (16H, m)
2.44 (2H, s), 3.20 (2H, m)
3.51 (1H, dd, J=8 Hz and 14 Hz)
3.67 (1H, dd, J=13 Hz and 4 Hz)
3.90–4.21 (4H, m)
4.85 (1H, m)
6.72 (1H, d, J=10 Hz)
6.99 (1H, d, J=2 Hz)
7.14 (1H, dd, J=9 Hz and 2 Hz)
7.37 (2H, d, J=9 Hz)
7.75 (1H, d, J=10 Hz)
12.31 (1H, s)

Example 122

In 100 ml of pyridine is dissolved 4.3 g of 6-{4-[N-(2,3-dihydroxypropyl)-N-cyclohexylmethylaminocarbonyl]butoxy}carbostyril. Thereto is added 4.3 g of acetic anhydride. The mixture is stirred for 8 hours at 50° C. with heating. Pyridine and chloroform are removed by evaporation under reduced pressure. The residue is made acidic with 5% hydrochloric acid and extracted with chloroform. The extract is washed with water and dried with anhydrous magnesium sulfate. The solvent is removed by evaporation. The residue is purified by means of a silica gel column chromatography (eluant; chloroform:methanol=50:1) to obtain 2.0 g of 6-{4[N-(2,3-diacetyloxypropyl)-N-cyclohexylmethylaminocarbonyl]butoxy}carbostyril.

Properties: Colorless powdery substance
Melting point: 98°–100° C.

Using appropriate starting materials and by procedure similar to that employed in Example 122, there are obtained compounds of Examples 3, 42, 66, 69, 73, 76, 78, 80, 82, 85, 87, 89, 91, 96 and 103.

Example 123

In 4 ml of methanol is dissolved 0.21 g of 6-{4-[N-(2,3-isopropylidenedioxypropyl)-N-(4-transhydroxymethyl-1-cyclohexylmethyl)aminocarbonyl]butoxy}carbostyril. Thereto is added 4 ml of 5% hydrochloric acid. The mixture is stirred for 2 hours at room temperature. To the reaction mixture is added 40 ml of chloroform. The mixture is made alkaline with an aqueous sodium hydrogen carbonate solution with ice cooling. The resulting mixture is extracted with chloroform. The extract is dried with anhydrous magnesium sulfate. The solvent is removed by evaporation. The residue is purified by means of a silica gel column chromatography (eluant; chloroform:methanol=8:1) to obtain 0.15 g of 6-{4-[N-(2,3-dihydroxypropyl)-N-(4-trans-hydroxymethyl-1-cyclohexylmethyl)aminocarbonyl}butoxy]-carbostyril.

Properties: colorless powdery substance
Melting point: 156°–159° C.

Example 124

In 10 ml of anhydrous ethanol are dissolved 1.19 g of 6-{4-[N-(3-chloro-2-hydroxypropyl)-N-cyclooctylemthylaminocarbonyl]butoxy}carbostyril and 10 ml of diethylamine. Thereto is added 0.7 g of potassium carbonate. The mixture is refluxed for 2 hours with heating and then extracted with chloroform. The extract is washed with water and dried with anhydrous magnesium sulfate. The solvent is removed by evaporation. The residue is purified by means of a silica gel column chromatography (eluant; chloroform:methanol=8:1) and recrystallized from diethyl ether to obtain 0.40 g of 6-{4-[N-(3-diethylamino-2-hydroxypropyl)-N-cyclooctylmethylaminocarbonyl]butoxy}carbostyril.

Properties: Colorless powdery substance
Melting point: 61°–63° C.

Using appropriates starting materials and by procedure similar to that employed in Example 124, there are obtained compounds of Examples 1–21, 23–30, 32–36, 38, 40, 43–49, 52, 56–63, 66–68, 71, 73, 76, 78, 80, 82, 85, 87, 89, 91 and 96.

Example 125

In 20 ml of ethanol is dissolved 2.25 g of 6-{4-[N-(3-chloro-2-hydroxypropyl)-N-cyclohexylmethylaminocarbonyl]butoxy}carbostyril. Thereto is added 0.88 g of potasium O-ethyl dithiocarbonate. The mixture is stirred for 2 hours at room temperature. Ethanol is removed by evaporation under reduced pressure. The residue is extracted with chloroform. The extract is washed with water and dried with anhydrous magnesium sulfate. The solvent is removed by evaporation. The residue is purified by means of a silica gel column chromatography (eluant; chloroform:methanol=20:1) and recrystallized from a mixture of chloroform and diethyl ether (1:3) to obtain 1.0 g of 6-{4-[N-(1,3-oxythiolane-2-thion-4-ylmethyl)-N-cyclohexylmethylaminocarbonyl]butoxy}carbostyril.

Properties: Yellow granular crystals
Melting point: 84° C. or above (decomposed)

Example 126

In 6 ml of ethylenediamine is dissolved 0.2 g of 6-{4-[N-(1,3-oxathiolane-2-thion-4-ylmethyl)-N-cyclohexylmethylaminocarbonyl}butoxy}carbostyril. The solution is stirred for 8 hours at room temperature, then it is made acidic with 5% hydrochloric acid. Chloroform extraction is effected and the extract is washed with water and dried with anhydrous magnesium sulfate. The solvent is removed by evaporation. The residue is purified by means of a silica gel column chromatography (eluant; chloroform:methanol=8:1) and recrystallized from diethyl ether to obtain 0.05 g of 6-{4-[N-(3-mercapto-2-hydroxypropyl)-N-cyclohexylmethylaminocarbonyl]butoxy}carbostyril.

Properties: Colorless powdery substance
Melting point: 105° C. or above (decomposed)

Example 127

In 30 ml of methanol is dissolved 12.10 g of 6-{4-[N-(4-methoxymethoxy-1-piperidinyl)ethyl-N-cyclooctylmethylaminocarbonyl]butoxy}carbostyril. Thereto is added 240 ml of 5% hydrochloric acid. The mixture is stirred for 8 hours at room temperature. To the mixture is added with a 10% aqueous potassium hydroxide solution under ice cooling to make the mixture alkaline. The resulting mixture is extracted with methylene chloride. The extract is washed with water and dried with anhydrous magnesium sulfate. The solvent is removed by evaporation. The residue is purified by means of a silica gel column chromatography (eluant; chloroform:methanol=8:1) and recyrstallized from ethanol to obtain 6.50 g of 6-{4-[N-(4-hydroxy-1-piperidinyl)ethyl-N-cyclooctylmethylaminocarbonyl]butoxy}carbostyril.

Properties: Colorless powdery substance
Melting point: 108°–110° C.

Using appropriate starting materials and by procedure similar to that employed in Example 127, there are obtained compounds of Examples 8, 21, 22, 67 and 68.

Example 128

In 80 ml of ethanol is dissolved 1.6 g of 6-{4-[N-(3-methylthio-1-methoxycarbonylpropyl)-N-cyclohexylmethylaminocarbonyl]butoxy}carbostyril. Thereto is added 3.2 g of sodium boron hydride. The mixture is stirred for 2 hours at 50°–60° C. The reaction mixture is neutralized with diluted hydrochloric acid and concentrated. The residue is extracted with a mixture of chloroform and methanol (10:1). The extract is purified by means of a silica gel column chromatography (eluant; chloroform:methanol=20:1). The resulting residue is recrystallized from a mixed solvent of dichloromethane-ethyl acetate-diethyl ether to obtain 0.78 g of 6-{4-[N-(3-methylthio-1-hydroxy-methylpropyl)-N-cyclohexylmethylaminocarbonyl]butoxy}carbostyril.

Properties: Colorless prism-like crystals
Melting point: 106.5°–108° C.

Using appropriate starting materials and by a procedure similar to that employed in Example 128, there are obtained compounds of Examples 13, 23, 25, 27–30, 32–36, 38, 40, 44–48, 58–61, 71, 72, 75, 95, 97, 100, 102, 104 and 120.

Example 129

To 50 ml of dimethylformamide are added 1.73 g of 6-hydroxycarbostyril, 1.8 g of $K_2CO_3$ and 0.5 g of KI. To this mixture being stirred at 60°–70° C. is dropwise added 4.2 g of N-[2-(1-pyrrolidinyl)ethyl]-N-(5-chloropentanoyl)-cyclohexylmethylamine. Then, the mixture is stirred for 4 hours at the same temperature. The solvent is removed by evaporation. The residue is dissolved in 200 ml of chloroform and the solution is washed with diluted hydrochloric acid, a 1% aqueous sodium hydroxide solution and water in this order, and dried with anhydrous magnesium sulfate. The desiccant is removed by filtration and the filtrate is concentrated. The residue is purified by means of a silica gel column chromatography (eluent; chloroform:methanol=20:1) and recrystallized from diethyl ether to obtain 0.5 g of 6-[4-{N-[2-(1-pyrrolidinyl)ethyl]-N-cyclohexylmethylaminocarbonyl}butoxy]carbostyril.

Properties: Colorless powdery substance
Melting point: 105°–106° C.

Using appropriate starting materials and by a procedure similar to that employed in Example 129, there are obtained compounds of Examples 2–121.

Example 130

In 3 ml of acetic acid is dissolved 0.2 g of 6-{4-[N-(2-hydroxypropyl)-N-cyclohexylmethylaminocarbonyl]-butoxy}carbostyril. Thereto is dropwise added 0.3 ml of an aqueous solution containing 0.07 g of chromic acid at room temperature. The mixture is stirred for 1 hour, and 0.3 ml of isopropyl alcohol is added. Acetic acid is removed by evaporation under reduced pressure. The residue is made alkaline with sodium bicarbonate and then extracted with chloroform. The extract is washed with water and dried with anhydrous magnesium sulfate. The solvent is removed by evaporation. The residue is purified by means of a silica gel column chromatography (eluent; chloroform:methanol=20:1) and recrystallized from diethyl ether to obtain 0.07 g of 6-[4-(N-acetylmethyl-N-cyclohexylmethylaminocarbonyl)-butoxy]carbostyril.
Properties: Colorless powdery substance
Melting point: 86°–88° C.

Pharmacological Test I

The platelet aggregation inhibitory activities of test compounds were determined according to the method by Born et al. [J. Physiol., London, 162, 67 (1962)] and by using Platelet Aggregation Tracer manufactured by Niko Bioscience Kabushiki Kaisha.

A blood sampled from a rabbit was mixed with 3.8% sodium citrate at proportions of 9 volumes (the former) and 1 volume (the latter). This sample was subjected to centrifugation at 1,100 rpm for 10 minutes to obtain a platelet rich plasma (PRP). The remaining sample was subjected to further centrifugation at 3,000 rpm for 15 minutes to obtain a platelet poor plasma (PPP).

The number of platelets in the PRP obtained above was counted by coulter Counter manufactured by Coulter Electronics Inc. Then, the PRP was diluted with the PPP so that the number of platelets in the PRP after dilution became 400,000 platelets/μl, whereby a PRP solution was prepared.

There were placed in a cell for aggregation determination, 2 μl of a solution containing a test compound at a given concentration and 200 μl of the PRP solution prepared above. The cell was heated at 37° C. for 1 minute. Then, to the cell contents was added 20 μl of adenosine diphosphate (ADP, manufactured by Sigma Co.) or 20 μl of a collagen suspension (Collagen Reagent Horm, manufactured by Hormon-Chemie Co.) to induce aggregation of platelets. Then, the platelet aggregation was determined for change in transmittance, and a platelet aggregation curve was drawn. Incidentally, the concentrations of the ADP and collagen were controlled so as to be 7.5 μM and 20 μg/ml, respectively, in terms of final concentration.

The mixture aggregation rate (MAR) of platelets was calculated from the platelet aggregation curve, using the following formula.

$$MAR = (b-a)/(c-a) \times 100$$

In the formula, a represents a transmittance of the PRP obtained in a similar test; b represents a transmittance of the PRP containing the test compound and the aggregation inducer, at the time of maximum change, obtained in the above test; and c represents a transmittance of the PPP obtained in a similar test.

In the above, MAR was calculated also for a control containing no test compound. Using this MAR as a base, the platelet aggregation inhibitions rate (%) of each test compound at various concentrations were calculated from the following formula.

Inhibition rate (%) = [1 − (MAR of test compound-containing PRP)/(MAR of test compound-free PRP)] × 100

From the platelet aggregation inhibitions of each test compound at various concentrations, there was obtained the concentration ($IC_{50}$) of each test compound giving a 50% platelet aggregation inhibition.

The following compounds were used as test compounds, and the results of the above test for these compounds are shown in Table 10.

Test Compounds

1: 6-[4-{N-cyclohexylmethyl-N-[2-(2β-hydroxymethyl-1-pyrrolidinyl)ethyl]aminocarbonyl}butoxy]carbostyril 2: 6-[4-{N-cyclohexylmethyl-N-[2-(2β-acetyloxymethyl-1-pyrrolidinyl)ethyl]aminocarbonyl}butoxy]carbostyril 3: 6-[4-{N-cyclooctylemthyl-N-2-(2β-hydroxymethyl-1-pyrrolidinyl)ethyl]aminocarbonyl}butoxy]carbostyril 4: 6-[4-{N-cyclooctylmethyl-N-[2-(2-hydroxymethyl-1-piperidinyl)ethyl]aminocarbonyl}butoxy]carbostyril 5: 6-{4-[N-cyclooctylmethyl-N-(2-pyrrolidinylethyl)aminocarbonyl]butoxy}carbostyril 6: 6-[4-{N-cyclooctylmethyl-N-[2-(3-hydroxy-1-pyrrolidinyl)ethyl]aminocarbonyl}butoxy]carbostyril oxalate 7: 6-{4-[N-cyclooctylmethyl-N-(2-morpholinoethyl)aminocarbonyl]butoxy}carbostyril 8: 6-[4-{N-cyclooctylmethyl-N-[2-(4-hydroxy-1-piperidinyl)ethyl]aminocarbonyl}butoxy]carbostyril 9: 6-[4-{N-cyclooctylmethyl-N-[2-(2,6-dimethyl-1-piperidinyl)ethyl]aminocarbonyl}butoxy]carbostyril 10: 6-[4-{N-cyclooctylmethyl-N-[2-(2B-dimethylaminomethyl-1-pyrrolidinyl)ethyl]aminocarbonyl}butoxy]carbostyril difumarate.

11: 6-[4-{N-cyclohexyl-N-[2-(4-methoxy-1-piperidinyl)ethyl]aminocarbonyl}butoxy]carbonstyril 12: 6-[4-{N-cyclohexylmethyl-N-[2-(1-imidazolyl)ethyl]aminocarbonyl}butoxy]carbostyril 13: 6-[4-{N-cyclohexylmethyl-N-[2-(1,2,4-triazol-1-yl)ethyl]aminocarbonyl}butoxy]carbostyril 14: 6-[4-{N-cyclohexylmethyl-N-[2-(1-ethyl-4α-hydroxy-2-pyrrolidinyl)ethyl]aminocarbonyl}butoxy]carbostyril 15: 6-[4-{N-cyclohexylmethyl-N-[2-(2β-methoxymethyl-1-pyrrolidinyl)ethyl]aminocarbonyl}butoxy]carbostyril 16: 6-[4-[N-cyclooctylmethyl-N-(2-diethylaminoethyl)aminocarbonyl]butoxy}carbostyril 17: 6-{4-[N-cyclooctylmethyl-N-(3-diethylaminopropyl)aminocarbonyl]butoxy}carbostyril oxalate 18: 6-{4-[N-cyclooctylmethyl-N-(4-diethylaminobutyl)aminocarbonyl]butoxy}carbostyril oxalate 19: 6-[4-(N-cyclooctylmethyl-N-diethylamidomethyl)aminocarbonyl]butoxy}carbostyril 20: 6-{4-[N-cyclooctylmethyl-N-(2-diethylaminoethyl)aminocarbonyl]butoxy}3,4-dihydrocarbostyril oxalate 21: 6-{4-[N-cyclooctylmethyl-N-(3-diethylamino-2(S)-propyl)aminocarbonyl]butoxy}carbostyril 22: 6-{4-[N-cyclooctylmethyl-N-(1-hdyroxy-3-diethylamino-2(R)-propyl)aminocarbonylbutoxy}carbostyril 23: 6-{4-[N-cyclooctylmethyl-N-(4-methylthio-1-diethylamino-2(R)-butyl)aminocarbonyl]butoxy}carbostyril 24: 6-{4-[N-cyclooctylmethyl-N-(2-acetylaminoethyl)aminocarbonyl]butoxy}carbostyril 25: 6-[4-[N-cyclooctylmethyl-N-{2-[N-ethyl-N-(2-hydroxyethyl)amino]ethyl}aminocarbonyl]butoy]-carbostyril 26: 6-[4-{N-cyclooctylmethyl-N-{2-(N-ethyl-N-allylaminoethyl}aminocarbonyl}butoxy]carbostyril 27: 6-{4-[N-cyclooctylmethyl-N-(3,4(β(-dimethyl-5(β)thiomoirpholinomethyl)aminocarbonyl]butoxy}carbostyril 28: 6-[4-{N-cyclohexylmethyl-N-[2-(2β-diethylamido-1-pyrrolidinyl)ethyl]aminocarbonyl}butoxy]carbostyril 29: 6-{4-[N-cyclooctylmethyl-N-(1-methyl-3-piperidinylmethyl)aminocarbonyl]butoxy}carbostyril 30: 6-[4-{N-cyclohexylmethyl-N-[2-(4-pyridylthio)ethyl]aminocarbonyl}butoxy]carbostyril 31: 6-[4-{N-cyclooctylmethyl-N-[(3-pyridyl)methyl]aminocarbonyl}butoxy]carbostyril 32: 6-[4-[N-cyclohexylmethyl-N-{2-[4-(2-hydroxyethyl)-1-piperazinyl]ethyl}aminocarbonyl]butoxy]carbostyril 33: 6-[4-{N-cyclooctylmethyl-N-[2-{N-ethyl-N-[2-(3,4-dimethoxyphenyl)ethyl]amino}ethyl]aminocarbonyl}butoxy]carbostyril oxalate 34: 6-{4-[N-cycloheptyl-N-(2,3-diacetyloxypropyl)aminocarbonyl]butoxy}carbostyril 35: 6-{4-[N-cycloheptyl-N-(2,3-isopropylidenedioxypropyl)aminocarbonyl]butoxy}carbostyril 36: 6-{4-[N-(2-tetrahydropyranylmethyl)-N-(2,3-diacetyloxypropyl)aminocarbonyl]butoxy}carbostyril 37: 6-{4-N-cyclohexylmethyl-N-(2,4-diacetyloxybutyl)aminocarbonyl]butoxy}carbostyril 38: 6-{4-[N-(4α-acetyloxymethyl-1β-cyclohexylmethyl-N-(2,3-diacetyloxypropyl)aminocarbonyl]butoxy}carbostyril 39: 6-{4-[N-(4α-hydroxymethyl-1β-cyclohexylmethyl-N-(2,3-isopropylidenedioxypropyl)aminocarbonyl]butoxy}carbostyril 40: 6-{4-[N-cyclohexylmethyl-N-(2-hydroxy-3-methoxypropyl)aminocarbonyl]butoxy}carbostyril 41: 6-{4-[N-cyclohexylmethyl-N-(2-hydroxy-1-methoxycarbonylethyl)aminocarbonyl]butoxy}carbostyril 42: 6-{4-[N-ethyl-N-(4α-acetyloxymethyl-1β-cyclohexylmethyl)aminocarbonyl]butoxy}carbostyril 43: 6-[4-(N-cyclohexylmethyl-N-acetylmethylaminocarbonyl)butoxy]carbostyril 44: 6-{4-[N-cyclohexylmethyl-N-(2-mercaptoethyl)aminocarbonyl]butoxy}carbostyril 45: 6-{4-[N-cyclohexylmethyl-N-[2-(2-tetrahydropyranylthio)ethyl]aminocarbonyl}butoxy]carbostyril 46: 6-{4-[N-cyclohexylmethyl-N-(4-methylthio-1-hydroxy-2-butyl)aminocarbonyl]butoxy}carbostyril 47: 6-{4-[N-cyclohexylmethyl-N-(4-methylthio-1-acetyloxy-2-butyl)aminocarbonyl]butoxy}carbostyril

TABLE 10

| Test compound No. | IC$_{50}$ (μM) ADP | IC$_{50}$ (μM) Collagen |
|---|---|---|
| 1 | 3.4 | 1.1 |
| 2 | 3.0 | 1.9 |
| 3 | 2.6 | 1.1 |
| 4 | 2.7 | 1.6 |
| 5 | 3.1 | 1.0 |
| 6 | 3.5 | 1.3 |
| 7 | 1.5 | 0.65 |
| 8 | 1.7 | 0.50 |
| 9 | 4.5 | 1.6 |
| 10 | 5.4 | 2.5 |
| 11 | 1.7 | 0.7 |
| 12 | 6.0 | 3.2 |
| 13 | 3.9 | 1.8 |
| 14 | 5.6 | 2.8 |
| 15 | 3.9 | 1.9 |
| 16 | 3.0 | 1.1 |
| 17 | 5.0 | 2.8 |
| 18 | 6.0 | 4.8 |
| 19 | 1.5 | 0.71 |
| 20 | 21.2 | 7.0 |
| 21 | 5.4 | 3.2 |
| 22 | 1.2 | 0.80 |
| 23 | 7.6 | 4.8 |
| 24 | 2.2 | 1.3 |
| 25 | 2.1 | 1.4 |
| 26 | 3.6 | 1.3 |
| 27 | 1.9 | 0.60 |
| 28 | 2.8 | 1.2 |
| 29 | 8.3 | 3.7 |
| 30 | 3.3 | 1.3 |
| 31 | 2.1 | 1.3 |
| 32 | 6.6 | 2.4 |
| 33 | 3.0 | 2.0 |
| 34 | 0.84 | 0.48 |
| 35 | 1.8 | 0.63 |
| 36 | 2.6 | 1.9 |
| 37 | 0.65 | 0.80 |
| 38 | 0.13 | 0.071 |
| 39 | 2.0 | 0.71 |
| 40 | 2.0 | 1.3 |
| 41 | 0.37 | 0.38 |
| 42 | 1.9 | 1.6 |
| 43 | 1.8 | 0.92 |
| 44 | 5.0 | 3.6 |
| 45 | 2.2 | 2.2 |
| 46 | 1.1 | 0.53 |
| 47 | 0.63 | 0.49 |

Pharmacological Test II

Increase in heart rate as well as hypotensive activity of test compounds were measured as follows by using mongrel dogs (body weight=10–20 kg). That is, mongrel dogs were put under anesthesia by intravenous administration of pentobarbital sodium, then fixed at the back position, and subjected to testing under artificial breathing condition. Blood pressure was measured by using a blood pressure transducer (P23XL, manufactured by Gould Statham Instruments, Inc.) via a cannula inserted into the femoral artery of the mongrel dog. Heart rate was measured via a tachometer, based on the pulse wave of the blood pressure. These signals were recorded on a thermal-pen type recorder (Recti-Horiz 8K, manufactured by Nihon Denki San-ei).

The test compounds mentioned in the Pharmacological Test I were also used as test compounds in this Test-II. Each of them was dissolved in a mixed solution of N,N'-dimenthylformamide and a physiological saline solution, and each resulting solution was administered to the test dogs through the cannulas inserted into their femoral arteries, in an amount of 30 μg (test compound)/kg of body weight. The heart rate of each dog after the administration of test compound was measured as mentioned above, whereby the maximum increase in heart rate was obtained.

The test results obtained are shown in Table 11.

TABLE 11

| Test compound No. | Maximum increase in heart rate (beats/min) (Administration amount = 30 μg/kg) |
|---|---|
| 1 | 7 |
| 3 | 12 |
| 4 | 6 |
| 5 | 5 |
| 6 | 5 |
| 8 | 5 |
| 9 | 0 |
| 12 | 12 |
| 14 | 4 |
| 16 | 7 |
| 18 | 5 |
| 20 | 4 |
| 21 | 7 |
| 23 | 4 |
| 29 | 2 |
| 32 | 8 |
| 33 | 12 |
| 44 | 11 |

Preparation of Tablets 1,000 tablets for oral administration, each containing 5 mg of 6-[4-{N-cyclohexylmethyl-N-[2-(1-pyrrolidinyl)ethyl]aminocarbonyl}butoxy]carbostyril, as prepared according to the following formulation.

| Ingredients | Amount (g) |
|---|---|
| 6-[4-{N-cyclohexylemthyl-N-[2-(1-pyrrolidinyl)ethyl1aminocarbonyl}-butoxy]carbostyril | 5 |
| Lactose (Japanese Pharmacopoeia grade) | 50 |
| Corn starch (Japanese Pharmacopoeia grade) | 25 |
| Crystalline celluloe (Japanese Pharmacoipoeia grade) | 25 |
| Methyl cellulose (Japanese Pharmacopoeia grade) | 1.5 |
| Magnesium stearate (Japanese Pharmacopoeia grade) | 1 |

That is, 6-[4-{N-cyclohexylmethyl-N-[2-(1-pyrrolidinyl)ethyl]aminocarbonyl}butoxy]carbostyril, lactose, corn starch and crystalline cellulose are mixed thoroughly. The mixture is subjected to granulation with a 5% aqueous methyl cellulose solution. The resulting granules are passed through a 200-mesh sieve and then dried carefully. The dried granules are passed through a 200-mesh sieve, mixed with magnesium stearate and press molded into tablets.

Preparation of Capsules 1,000 two-piece type hard gelatin capsules for oral use, each containing 10 mg of 6-[4-{N-cyclohexylmethyl-N-[2-(1-pyrrolidinyl)ethyl]aminocarbonyl}butoxy]-carbostyril, are prepared according to the following formulation.

| Ingredient | Amount (g) |
|---|---|
| 6-[4-{N-cyclohexylmethyl-N-]2-(1-pyrrolidinyl)ethyl]aminocarbonyl}-butoxy]carbostyril | 10 |

| Ingredient | Amount (g) |
|---|---|
| Lactose (Japanese Pharmacopoeia grade) | 80 |
| Starch (Japanese Pharmacopoeia grade) | 30 |
| Talc (Japanese Pharmacopoeia grade) | 5 |
| Magnesium stearate (Japanese Pharmacopoeia grade) | 1 |

That is, each of the above components is ground finely and they are thoroughly stirred so as to give them into a uniform mixture. The mixture is then filled into gelatin capsules for oral administration, each having the desired dimensions.

Preparation of Injection

A sterilized aqueous solution suitable for parenteral administration is prepared according to the following formulation.

| Ingredients | Amount (g) |
|---|---|
| 6-[4-{N-cyclohexylmethyl-N-]2-(1-pyrrolidinyl)ethyl]aminocarbonyl}butoxy]-carbostyril | 1 |
| Polyethylene glycol (Japanese Pharmacopoeia grade) (molecular weight: 4,000) | 0.3 |
| Sodium chloride (Japanese Pharmacopoeia grade) | 0.9 |
| Polyoxyethylene sorbitan monooleate (Japanese Pharmacopoeia grade) | 0.4 |
| Sodium metabiphosphite | 0.1 |
| Methylparaben (Japanese Pharmacopoeia grade) | 0.18 |
| Propylparaben (Japanese Pharmacopoeia grade) | 0.02 |
| Distilled water for injection | 100 ml |

That is, the above parabens, sodium methbiphosphite and sodium chloride are dissolved in distilled water of an amount about half of the above shown amount, at 80° C. with stirring. The resulting solution is cooled to 40° C. Therein are dissolved 6-[4-{N-cyclohexylmethyl-N-[2-(1-pyrrolidinyl)ethyl]aminocarbonyl}butoxy]carbostyril, polyethylene glycol and polyoxyethylene sorbitan monooleate in this order. Then, to the resulting solution is added distilled water so to make them in a final volume. The thus prepared solution is sterilized and filtered by using a filter paper to prepare an injection.

We claim:

1. A carbostyril compound or salt thereof, of the formula

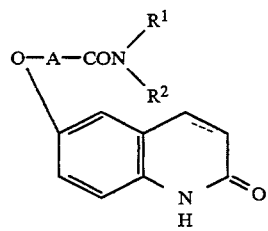

wherein A is $C_1$–$C_6$ alkylene; is $C_3$–$C_8$ cycloalkyl-$C_1$–$C_6$ alkyl, which may have, as a substituent, a $C_1$–$C_6$ alkoxycarbonyl group, a carboxy group, a $C_2$–$C_6$ alkanoyloxy-$C_1$–$C_6$ alkyl group, an amino-$C_1$–$C_6$ alkyl group, a $C_1$–$C_6$ alkylamino-$C_1$–$C_6$ alkyl group or a hydroxy-$C_1$–$C_6$ alkyl group, or $R^1$ is $C_3$–$C_8$ cycloalkyl, tetrahydropyranyl-$C_1$–$C_6$ alkyl, $C_1$–$C_3$ alkylene-dioxy- $C_1$-$C_6$ alkyl, phenyl-$C_1$-$C_6$ alkyl having, as a substituent on the phenyl ring, 1 to 3 groups selected from $C_1$-$C_6$ alkyl groups or a hydroxyl group, or $R^1$ is piperidinyl-$C_1$-$C_6$ alkyl having a $C_1$-$C_6$ alkyl group as a substituent; $R^2$ is morpholino-$C_1$-$C_6$ alkyl or thiomorpholino-$C_1$-$C_6$ alkyl either of which may have, as a substituent thereon, 1 to 3 groups selected from hydroxy-$C_1$-$C_6$ alkyl groups, $C_2$-$C_6$ alkanoyloxy-$C_1$-$C_6$ alkyl groups, a hydroxyl group, $C_1$-$C_6$ alkyl groups, amino-$C_1$-$C_6$ alkyl groups, $C_1$-$C_6$ alkylamino-$C_1$-$C_6$ alkyl groups, $C_1$-$C_6$ alkoxy groups, $C_1$-$C_6$ alkoxy-$C_1$-$C_6$ alkoxy groups, $C_1$-$C_6$ alkoxy-$C_1$-$C_6$ alkyl groups, a thio group or $C_1$-$C_6$ alkylamido groups; the carbon-carbon bond between the 3- and 4-positions in the carbostyril skeleton being a single bond or a double bond.

2. The carbostyril compound or salt thereof of claim 1, wherein $R^1$ is $C_3$-$C_8$ cycloalkyl-$C_1$-$C_6$ alkyl, which may have, as a substituent, a $C_1$-$C_6$ alkoxycarbonyl group, a carboxy group, a $C_2$-$C_6$ alkanoyloxy-$C_1$-$C_6$ alkyl group, an amino-$C_1$-$C_6$ alkyl group, a $C_1$-$C_6$ alkoxyamino-$C_1$-$C_6$ alkyl group or a hydroxy-$C_1$-$C_6$ alkyl group, or $R^1$ is $C_3$-$C_8$ cycloalkyl.

3. The carbostyril compound or salt thereof of claim 1, wherein $R^1$ is tetrahydropyranyl-$C_1$-$C_6$ alkyl, $C_1$-$C_3$ alkylenedioxy-$C_1$-$C_6$ alkyl, phenyl-$C_1$-$C_6$ alkyl having, as a substituent on the phenyl ring, 1 to 3 groups selected from $C_1$-$C_6$ alkyl groups or a hydroxyl group, or $R^1$ is piperidinyl-$C_1$-$C_6$ alkyl having a $C_1$-$C_6$ alkyl group as a substituent.

4. The carbostyril compound or salt thereof of claim 1, wherein the bond between the 3-position and 4-position of the carbostyril skeleton is a single bond.

5. The carbostyril compound or salt thereof of claim 1, wherein the bond between the 3-position and 4-position of the carbostyril skeleton is a double bond.

6. A pharmaceutical composition for inhibiting platelet aggregation comprising, as an active ingredient, a carbostyril compound or salt thereof of claim 1 and a pharmaceutically acceptable carrier.

7. A carbostyril compound or salt thereof, of the formula

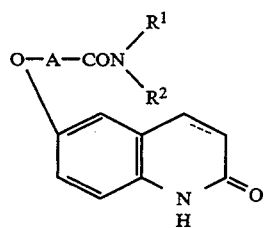

wherein A is $C_1$-$C_6$ alkylene; $R^1$ is $C_3$-$C_8$ cycloalkyl-$C_1$-$C_6$ alkyl, which may have, as a substituent, a $C_1$-$C_6$ alkoxycarbonyl group, a carboxy group, a $C_2$-$C_6$ alkanoyloxy-$C_1$-$C_6$ alkyl group, an amino-$C_1$-$C_6$ alkyl group, a $C_1$-$C_6$ alkylamino-$C_1$-$C_6$ alkyl group or a hydroxy-$C_1$-$C_6$ alkyl group, or $R^1$ is $C_3$-$C_8$ cycloalkyl, tetrahydropyranyl-$C_1$-$C_6$ alkyl, $C_1$-$C_3$ alkylenedioxy-$C_1$-$C_6$ alkyl, phenyl-$C_1$-$C_6$ alkyl having, as a substituent on the phenyl ring, 1 to 3 groups selected from $C_1$-$C_6$ alkyl groups or a hydroxyl group, or $R^1$ is piperidinyl-$C_1$-$C_6$ alkyl having a $C_1$-$C_6$ alkyl group as a substituent; $R^2$ is tetrahydropyranylthio-$C_1$-$C_6$ alkyl, pyridylthio-$C_1$-$C_6$ alkyl, $C_1$-$C_3$ alkylenedioxy-$C_1$-$C_6$ alkyl, or $C_1$-$C_6$ alkyl which may have, as a substituent, 1 to 2 groups selected from an amino group, a hydroxyl group, a $C_1$-$C_6$ alkylthio group, a $C_2$-$C_6$ alkanoyloxy group, a tetrahydropyranyloxy group, a halogen atom, a $C_1$-$C_6$ alkanoyl group, a mercapto group, a $C_1$-$C_6$ alkoxycarbonyl group, a carboxy group, a $C_1$-$C_6$ alkoxy group, an amido group or a $C_1$-$C_6$ alkylamido group, wherein the amino group, as a substituent for the $C_1$-$C_6$ alkyl group, may have, as a substituent, a $C_1$-$C_6$ alkanoyl group, a phenyl-$C_1$-$C_6$ alkyl group, which may have a $C_1$-$C_6$ alkoxy group as a substituent on the phenyl ring, a $C_2$-$C_6$ alkenyl group, a hydroxy-$C_1$-$C_6$ alkyl group or a $C_1$-$C_6$ alkyl group and wherein when $R^2$ is a $C_1$-$C_6$ alkyl group which may have 1 to 2 hydroxyl groups as a substituent, a $C_1$-$C_6$ alkyl group having a $C_1$-$C_6$ alkanoyloxy group as a substituent, or a $C_1$-$C_6$ alkyl group having a $C_1$-$C_6$ alkoxy group as a substituent, then $R^1$ must not be a $C_3$-$C_8$ cycloalkyl-$C_1$-$C_6$ alkyl group, a $C_3$-$C_8$ cycloalkyl group or a tetrahydropyranyl $C_1$-$C_6$ alkyl group; the carbon-carbon bond between the 3- and 4-positions in the carbostyril skeleton being a single bond or a double bond.

8. The carbostyril compound or a salt thereof of claim 7, wherein $R^1$ is $C_3$-$C_8$ cycloalkyl $C_1$-$C_6$ alkyl, which may have, as a substituent, a $C_1$-$C_6$ alkoxycarbonyl group, a carboxy group, a $C_2$-$C_6$ alkanoyloxy-$C_1$-$C_6$ alkyl group, an amino-$C_1$-$C_6$ alkyl group, a $C_1$-$C_6$ alkylamino-$C_1$-$C_6$ alkyl group or a hydroxy-$C_1$-$C_6$ alkyl group, or $R^1$ is $C_3$-$C_8$ cycloalkyl.

9. The carbostyril compound or a salt thereof of claim 7, wherein $R^1$ is tetrahydropyranyl-$C_1$-$C_6$ alkyl, $C_1$-$C_3$ alkylenedioxy-$C_1$-$C_6$ alkyl, phenyl-$C_1$-$C_6$ alkyl having, as a substituent on the phenyl ring, 1 to 3 groups selected from $C_1$-$C_6$ alkyl groups or a hydroxyl group, or $R^1$ is piperidinyl-$C_1$-$C_6$ alkyl having a $C_1$-$C_6$ alkyl group as a substituent.

10. The carbostyril compound or a salt thereof of claim 8, wherein $R^2$ is $C_1$-$C_6$ alkyl which may have, as a substituent, 1 to 2 groups selected from an amino group, a hydroxyl group, a $C_1$-$C_6$ alkylthio group, a $C_2$-$C_6$ alkanoyloxy group, a tetrahydropyranyloxy group, a halogen atom, a $C_1$-$C_6$ alkanoyl group, a mercapto group, a $C_1$-$C_6$ alkoxycarbonyl group, a carboxy group, a $C_1$-$C_6$ alkoxy group, an amido group or a $C_1$-$C_6$ alkylamido group, the amino group being unsubstituted or substituted by a $C_1$-$C_6$ alkanoyl group, a phenyl-$C_1$-$C_6$ alkyl group, which may have a $C_1$-$C_6$ alkoxy group as a substituent on the phenyl ring, a $C_2$-$C_6$ alkenyl group, a hydroxy-$C_1$-$C_6$ alkyl group or a $C_1$-$C_6$ alkyl group.

11. The carbostyril compound or a salt thereof of claim 8, wherein $R^2$ is tetrahydropyranylthio-$C_1$-$C_6$ alkyl, pyridylthio-$C_1$-$C_6$ alkyl or $C_1$-$C_3$ alkylenedioxy-$C_1$-$C_6$ alkyl.

12. The carbostyril compound or a salt thereof of claim 9, wherein $R^2$ is $C_1$-$C_6$ alkyl which may have, as a substituent, 1 to 2 groups selected from an amino group, a hydroxyl group, a $C_1$-$C_6$ alkylthio group, a $C_2$-$C_6$ alkanoyloxy group, a tetrahydropyranyloxy group, a halogen atom, a $C_1$-$C_6$ alkanoyl group, a mercapto group, a $C_1$-$C_6$ alkoxycarbonyl group, a carboxy group, a $C_1$-$C_6$ alkoxy group, an amido group or a $C_1$-$C_6$ alkylamido group, the amino group being unsubstituted or substituted by a $C_1$-$C_6$ alkanoyl group, a phenyl-$C_1$-$C_6$ alkyl group, which may have a $C_1$-$C_6$ alkoxy group as a substituent on the phenyl ring, a $C_2$-$C_6$ alkenyl group, a hydroxy-$C_1$-$C_6$ alkyl group or a $C_1$-$C_6$ alkyl group.

13. The carbostyril compound or a salt thereof of claim 9, wherein $R^2$ is tetrahydropyranylthio-$C_1$-$C_6$ alkyl, pyridylthio-$C_1$-$C_6$ alkyl or $C_1$-$C_3$ alkylenedioxy-$C_1$-$C_6$ alkyl.

14. The carbostyril compound or a salt thereof of claim 10, wherein $R^2$ is $C_1$-$C_6$ alkyl which may have, as a substituent, 1 to 2 groups selected from an amino group, or a hydroxyl group, the amino group being unsubstituted or substituted by a $C_1$-$C_6$ alkanoyl group, a phenyl-$C_1$-$C_6$ alkyl group, which may have a $C_1$-$C_6$ alkoxy group as a substituent on the phenyl ring, a $C_2$-$C_6$ alkenyl group, a hydroxy-$C_1$-$C_6$ alkyl group or a $C_1$-$C_6$ alkyl group.

15. The carbostyril compound or a salt thereof of claim 12, wherein $R^2$ is $C_1$-$C_6$ alkyl which may have, as a substituent, 1 to 2 groups selected from an amino group, or a hydroxyl group, the amino group being unsubstituted or substituted by a $C_1$-$C_6$ alkanoyl group, a phenyl-$C_1$-$C_6$ alkyl group, which may have a $C_1$-$C_6$ alkoxy group as a substituent on the phenyl ring, a $C_2$-$C_6$ alkenyl group, a hydroxy-$C_1$-$C_6$ alkyl group or a $C_1$-$C_6$ alkyl group.

16. The carbostyril compound or salt thereof of claim 14, wherein the bond between the 3-position and 4-position of the carbostyril skeleton is a single bond.

17. The carbostyril compound or salt thereof of claim 15, wherein the bond between the 3-position and 4-position of the carbostyril skeleton is a double bond.

18. The carbostyril compound or a salt thereof of claim 7, wherein $R^1$ is unsubstituted $C_3$-$C_8$ cycloalkyl $C_1$-$C_6$ alkyl; $R^2$ is $C_1$-$C_6$ alkyl which may have, as a substituent, 1 to 2 groups selected from an amino group or a hydroxyl group, the amino group being unsubstituted or substituted by a $C_1$-$C_6$ alkanoyl group, a phenyl-$C_1$-$C_6$ alkyl group, which may have a $C_1$-$C_6$ alkoxy group as a substituent on the phenyl ring, a $C_2$-$C_6$ alkenyl group, a hydroxy-$C_1$-$C_6$ alkyl group or a $C_1$-$C_6$ alkyl group; and the bond between the 3-position and 4-position of the carbostyril skeleton being a double bond.

19. A pharmaceutical composition for inhibiting platelet aggregation comprising, as an active ingredient, a carbostyril compound or salt thereof of claim 7 and a pharmaceutically acceptable carrier.

20. 6-[4-{N-cyclooctylmethyl-N-[2-(1-pyrrolidinyl)ethyl]aminocarbonyl}butoxy]carbostyril.

21. 6-[4-{N-cyclohexylmethyl-N-[2-(2$\beta$-hydroxymethyl-1pyrrolidinyl)ethyl]aminocarbonyl}butoxy]-carbostyril.

22. 6-{4-[N-cyclooctylmethyl-N-(2-diethylaminoethyl)aminocarbonyl]butoxy}carbostyril.

23. 6-{4-[N-cyclooctylmethyl-N-(1-hydroxy-3-diethylamino-2(R)-propyl)aminocarbonyl]butoxy}carbostyril.

* * * * *

UNITED STATES PATENT AND TRADEMARK OFFICE
CERTIFICATE OF CORRECTION

PATENT NO. : 5,401,740
DATED : March 28, 1995
INVENTOR(S) : Takao NISHI et al.

It is certified that error appears in the above-indentified patent and that said Letters Patent is hereby corrected as shown below:

Claim 1, column 114, line 62, before "is" (second occurrence) insert -- $R^1$ --.

Signed and Sealed this

Eighteenth Day of July, 1995

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,401,740
DATED : March 28, 1995
INVENTOR(S) : Takao Nishi et al.

It is certified that error appears in the above-indentified patent and that said Letters Patent is hereby corrected as shown below:

On the title page, item [73] Assignee should read --Otsuka Pharmaceutical Co., Ltd.--

Signed and Sealed this

Twenty-second Day of October, 1996

Attest:

BRUCE LEHMAN

*Attesting Officer*     *Commissioner of Patents and Trademarks*